United States Patent
Bhavar et al.

(10) Patent No.: US 11,352,359 B2
(45) Date of Patent: Jun. 7, 2022

(54) PI3K PROTEIN KINASE INHIBITORS

(71) Applicant: Rhizen Pharmaceuticals SA, La Chaux de Fonds (CH)

(72) Inventors: Prashant Kashinath Bhavar, Hyderabad (IN); Swaroop Kumar Venkata Satya Vakkalanka, La Chaux de Fonds (CH); Govindarajulu Babu, Hyderabad (IN)

(73) Assignee: RHIZEN PHARMACEUTICALS AG, Basel (CH)

( * ) Notice: Subject to any disclaimer, the term of this patent is extended or adjusted under 35 U.S.C. 154(b) by 0 days.

(21) Appl. No.: 14/902,536

(22) PCT Filed: Jul. 1, 2014

(86) PCT No.: PCT/IB2014/062775
§ 371 (c)(1),
(2) Date: Dec. 31, 2015

(87) PCT Pub. No.: WO2015/001491
PCT Pub. Date: Jan. 8, 2015

(65) Prior Publication Data
US 2016/0207929 A1 Jul. 21, 2016

(30) Foreign Application Priority Data

Jul. 2, 2013 (IN) .......................... 2937/CHE/2013
Dec. 18, 2013 (IN) .......................... 5935/CHE/2013

(51) Int. Cl.
C07D 487/04 (2006.01)
A61K 31/519 (2006.01)
A61K 45/06 (2006.01)

(52) U.S. Cl.
CPC .......... *C07D 487/04* (2013.01); *A61K 31/519* (2013.01); *A61K 45/06* (2013.01)

(58) Field of Classification Search
CPC ........................... A61K 31/519; C07D 487/04
USPC ........................................ 544/262; 514/262.1
See application file for complete search history.

(56) References Cited

U.S. PATENT DOCUMENTS 7,585,868 B2 * 9/2009 Knight ................ C07D 487/04
514/262.1

FOREIGN PATENT DOCUMENTS

| CN | 101965335 A | | 2/2011 |
|---|---|---|---|
| WO | WO-2009088986 A1 | | 7/2009 |
| WO | WO 2009088990 | * | 7/2009 |
| WO | WO-2010/059593 A1 | | 5/2010 |
| WO | WO-2010059593 A1 | | 5/2010 |

OTHER PUBLICATIONS

Stella (J. Pharmaceutical Sciences, 2010, 99(12), pp. 4755-4765).*
Ameriks et al., Current Topics in Medicinal Chemistry, 9(8):738-753 (May 1, 2009).
Williams et al., Chemistry and Biology, Current Biology, 17(2):123-134, Feb. 26, 2010.
International Search Report issued in PCT/IB2014/062775, dated Sep. 16, 2014.
Ameriks, et al., Small Molecule Inhibitors of Phosphoinositide 3-Kinase (PI3K) .delta. and .gamma., Current Topics in Medicinal Chemistry, Bentham Science Publishers Ltd. Hilversum, 2009. 9:8:783-753.
Williams, et a., Discovery of Dual Inhibitors of the Immune Cell PI3Ks p110, and p110, a Prototype for New Anti-Inflammatory Drugs, Chemistry and Biology, Current Biology, London, GB, 2010, 17:2:123-124.
International Search Report issued in PCT/IB2014/062775 dated Jun. 9, 2014.

* cited by examiner

*Primary Examiner* — Susanna Moore
(74) *Attorney, Agent, or Firm* — Blank Rome LLP

(57) ABSTRACT

The present disclosure provides novel compounds useful as PI3K protein kinase modulators, in particular as PI3K delta (δ) and/or gamma (γ) protein kinase modulators. The present disclosure also provides methods for preparing PI3K protein kinase modulators, pharmaceutical compositions containing them, and methods of treatment, prevention and/or amelioration of PI3K kinase mediated diseases or disorders with them.

15 Claims, No Drawings

PI3K PROTEIN KINASE INHIBITORS

The present application is the U.S. national phase of PCT/IB2014/062775, filed Jul. 1, 2014, which claims the benefit of Indian Patent Application Nos. 2937/CHE/2013, filed Jul. 2, 2013, an 5935/CHE/2013, filed Dec. 18, 2013, each of which are incorporated by reference in its entirety.

FIELD OF THE INVENTION

The present invention provides novel compounds, useful as PI3K protein kinase modulators and in particular as PI3K delta (δ) and/or gamma (γ) protein kinase modulators, methods of preparing them, pharmaceutical compositions containing them and methods of treatment, prevention and/or amelioration of PI3K kinase mediated diseases or disorders with them.

BACKGROUND OF THE INVENTION

Phosphatidylinositol (hereinafter abbreviated as "PI") is one of a number of phospholipids found in cell membranes. In recent years it has become clear that PI plays an important role in intracellular signal transduction. Cell signaling via 3'-phosphorylated phosphoinositides has been implicated in a variety of cellular processes, e.g., malignant transformation, growth factor signaling, inflammation, and immunity (Rameh et al. (1999) *J. Biol Chem,* 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al. (1992) *Trends Cell Biol* 2:358-60).

The phosphoinositide 3-kinases (PI3Ks) are a family of enzymes that regulate diverse biological functions in every cell type by generating phosphoinositide second-messenger molecules. As the activity of these phosphoinositide second messengers is determined by their phosphorylation state, the kinases and phosphatises that act to modify these lipids are central to the correct execution of intracellular signaling events. Phosphoinositide 3-kinases (PI3K) phosphorylate lipids at the 3-hydroxyl residue of an inositol ring (Whitman et al. (1988) *Nature,* 332:664) to generate phosphorylated phospholipids (PIP3s) which act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIPS and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al. (2002) *Nature Rev. Cancer* 2:489; Phillips et al. (1998) *Cancer* 83:41).

The members of the class I family of PI3Ks are dimers of a regulatory and a catalytic subunit. The class I family consists of four isoforms, determined by the 110 kDa catalytic subunits α, β, γ and δ. Engelman J A, *Nat Rev Genet* 2006; 7:606-19; Carnero A, *Curr Cancer Drug Tar-* gets 2008; 8:187-98; Vanhaesebroeck B, *Trends Biochem Sci* 2005; 30:194-204. Class I can be subdivided into two subclasses: Ia, formed by the combination of p110 α, β, and δ and a regulatory subunit (p85, p55 or p50) and Ib, formed by p110 γ and p101 regulatory subunits.

The four class I PI3K isoforms differ significantly in their tissue distribution. PI3K α and PI3Kβ are ubiquitous and activated downstream of receptor tyrosine kinases (RTK) whereas PI3K δ and PI3K γ are primarily limited to hematopoietic and endothelial cells, and are activated downstream of RTKs, and G protein coupled receptors (GPCR), respectively. Mouse genetic studies have revealed that PI3K α and PI3β are essential for normal development, whereas loss of PI3K δ and/or PI3K γ yields viable offspring with selective immune deficits The expression pattern and functions of PI3K δ and PI3K γ have generated much interest in developing PI3Kδ/γ inhibitors as agents for many diseases, including rheumatoid arthritis, allergies, asthma, chronic obstructive pulmonary disease and multiple sclerosis (Hirsch et al., Pharmacol. Ther. 118, 192-205 2008; Marone et al., Biochim. Biophys. Acta. 1784, 159-185. 2008; Rommel et al. Nat. Rev. Immunol. 7, 191-201, 2007; Ruckle et al., Nat. Rev. Drug Discov. 5, 903-918.2006). Studies using both pharmacologic and genetic methods have shown these two isoforms often demonstrate synergistic interactions with each other (Konrad et al., J. Biol. Chem. 283, 33296-33303. 2008; Laffargue et al., Immunity 16, 441-451.2002). In mast cells, for example, PI3Kδ is essential for degranulation in response to IgE cross-linking of Fc-receptors (Ali et al., J. Immunol. 180, 2538-2544. 2008), but PI3Kγ plays an important role in amplifying the response (Laffargue et al., Immunity 16, 441-451 2002). Similar effects have been seen in other cellular functions, including lymphocyte homing and the neutrophil respiratory burst where PI3Kγ plays a critical role and PI3Kδ amplifies each process. The nonredundant but related roles of PI3Kδ and PI3Kγ have made it difficult to determine which of the two isoforms (alone or in combination) is best targeted in a particular inflammatory disorder. Studies using mice that lack PI3Kδ and/or PI3Kγ or express kinase-dead variants of PI3Kδ and PI3Kγ have been valuable tools in understanding their roles. For example, PI3Kδ knockout mice demonstrated diminished neutrophil chemotaxis, diminished antibody production (both T cell dependent and independent) (Jou et al., Mol. Cell. Biol. 22, 8580-8591. 2002), and lower numbers of mature B cells (Clayton et al., J. Exp. Med. 196, 753-763. 2002; Jou et al., 2002), and a decrease in their proliferation in response to anti-IgM (Jou et al., 2002). This phenotype was replicated in the PI3Kδ kinase-dead variant and with PI3Kδ selective inhibitors along with decreased numbers of and proliferation of mast cells, and an attenuated allergic response. The PI3Kγ knockout contained higher numbers of, but less responsive, neutrophils, lower numbers of and less responsive macrophages and dendritic cells displayed decreased mast cell degranulation (Laffargue et al., 2002), a higher ratio of CD4+ to CD8+ T cells), increased thymocyte apoptosis, diminished induction of CXCR3 on activated T cells and decreased cardiac contractility. This latter effect on cardiac tissue was a concern for chronic dosing of patients with PI3Kγ inhibitors. However, this concern was largely mitigated when the PI3Kγ kinase-dead variant (which better mimics inhibition of the kinase rather than loss of the protein) showed similar immune cell phenotypes, but importantly had no cardiac defects. The cardiac effect was later shown to be due to scaffolding effects rather than the catalytic activity of PI3Kγ. The dual PI3Kδ/PI3Kγ knockout was viable but exhibited serious defects in T cell development and thymocyte survival. The PI3Kγ knockout/PI3Kδ kinase-dead combination produced a similar phenotype suggesting that at least within the immune system, the role of PI3Kδ is likely only a catalytic one. Interpretation of studies using knockout and kinase-dead mice can be challenging because these models provide only a steady-state picture of the immune system, lack temporal and dose control, and do not permit a full understanding of how a dynamic immune response will react to reversible inhibition. Selective inhibitors with varying profiles (PI3Kδ, PI3Kγ, and PI3Kδ/γ) are necessary for studies of leukocyte signaling in order to assess the relative contributions of each PI3K to immune cell activation. (see Olusegon et al., Chemistry & Biology 1, 123-134 including the cited references threin)

Dual inhibition of δ/γ is strongly implicated as an intervention strategy in allergic and non-allergic inflammation of the airways and other autoimmune diseases. Scientific evidence for PI3K-δ and γ gamma involvement in various cellular processes underlying asthma and COPD stems from inhibitor studies and gene-targeting approaches. Also, resistance to conventional therapies such as corticosteroids in several COPD patients has been attributed to an up-regulation of the PI3K δ/γ pathway. Disruption of PI3K-δ/γ signalling therefore provides a novel strategy aimed at counteracting the immuno-inflammatory response. Due to the pivotal role played by PI3K-δ and γ in mediating inflammatory cell functionality such as leukocyte migration and activation, and mast cell degranulation, blocking these isoforms may also be an effective strategy for the treatment of rheumatoid arthritis as well. Given the established criticality of these isoforms in immune surveillance, inhibitors specifically targeting the delta and gamma isoforms would be expected to attenuate the progression of immune response encountered in airway inflammation and rheumatoid arthritis. Given the established criticality of these isoforms in immune surveillance, inhibitors specifically targeting the δ and γ isoforms would be expected to attenuate the progression of immune response encountered in airway inflammation and rheumatoid arthritis (William et. al Chemistry & Biology. 17:123-134, 2010 and Thompson, et al. Chemistry & Biology. 17:101-102. 2010)

WO 2014/071109, WO 2014/071105, WO 2014/004470, WO 2011/008302, WO 2010/059593, US 2009/0312319, WO 2009088986A1 and WO 2009088990 disclose 2,3 disubstituted isoquinoline derivatives as Pi3K inhibitors and WO 2013147649, WO 2013116562, WO 2013029116, WO 2012/118978, WO 2012/009452 and WO 2008/127226 disclose 2, 3 disubstituted quinazolin derivatives as Pi3K inhibitors There is considerable evidence indicating that Class Ia PI3K enzymes contribute to tumourigenesis in a wide variety of human cancers, either directly or indirectly (Vivanco and Sawyers, *Nature Reviews Cancer,* 2002, 2, 489-501; Marone et al., *Biochimica et Biophysica Acta* 1784 (2008) 159-185). In particular, the p110 delta isoform has been implicated in biological functions related to immune-inflammatory diseases, including signaling from the B-cell receptor, T cell receptor, FcR signaling of mast cells and monocyte/macrophage, and osteoclast function/RANKL signaling (Deane J and Fruman D A (2004) *Annu Rev. Immunol.* 2004. 22:563-98; Janas et al., *The Journal of Immunology,* 2008, 180: 739-746; Marone R et al., *Biochim. Biophy. Acta* 2007, 1784:159-185). Deletion of the PI3K delta gene or selective introduction of a catalytically inactive mutant of PI3K delta causes a nearly complete ablation of B cell proliferation and signaling, and impairment of signaling through T cells as well.

Reviews and studies regarding PI3K and related protein kinase pathways have been given by Pixu Liu et. al. (*Nature Reviews Drug Discovery,* 2009, 8, 627-644); Nathan T. et. al. (Mol Cancer Ther., 2009; 8 (1) January, 2009); Romina Marone et, al. (Biochimica et Biophysica Acta 1784 (2008) 159-185) and B. Markman et. al. (Annals of oncology Advance access published August 2009). Similarly reviews and studies regarding role of PI3K δ and γ have been given by William et. al Chemistry & Biology. 17:123-134, 2010 and Timothy et. al J Med Chem. web publication 27$^{th}$ august 2012, Berndt et. al. Nature Chemical Biology (2010), 6(2), 117-124, Nature Chemical Biology (2010), 6(4), 306, and Nature Chemical Biology (2010), 6(3), 244, Williams et. al. Chemistry & Biology (Cambridge, Mass., United States) (2010), 17(2), 123-134, Apsel, Beth et. al. Nature Chemical Biology (2008), 4(11), 691-699 and Knight, Zachary A et al Cell (Cambridge, Mass., United States) (2006), 125(4), 733-747. All of these literature disclosures are incorporated herein as reference in their entirety for all purposes.

There still remains an unmet and dire need for small molecule kinase modulators in order to regulate and/or modulate transduction of kinases, particularly PI3K, for the treatment of diseases and disorders associated with kinase-mediated events.

SUMMARY OF INVENTION

The present invention is directed to compounds, which are useful as PI3K protein kinase modulators and in particular as PI3K δ and/or γ inhibitors.

In one embodiment, the present invention relates to a compound of formula (I):

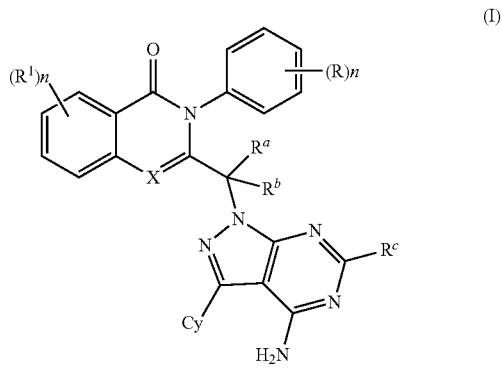

or a tautomer thereof, N-oxide thereof, pharmaceutically acceptable ester thereof, prodrug thereof, or pharmaceutically acceptable salt thereof, wherein each occurrence of $R^1$ is independently H, substituted or unsubstituted alkyl, substituted or unsubstituted alkenyl, substituted or unsubstituted alkynyl or halogen;

X is CH or N;

each occurrence of R is independently H, substituted or unsubstituted alkyl, or halogen;

$R^a$ and $R^b$ are independently selected from H and substituted or unsubstituted alkyl;

$R^c$ is H, substituted or unsubstituted alkyl, —NH$_2$ or halogen;

each occurrence of n is independently selected from 0, 1, 2, 3 and 4; and

Cy is selected from

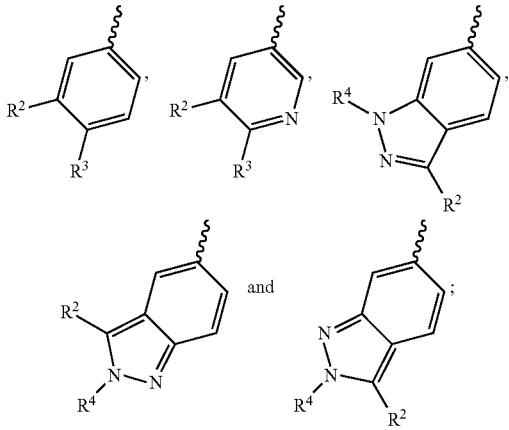

wherein

R² and R³ are independently selected from H, halogen, hydroxyl, substituted or unsubstituted alkyl, substituted or unsubstituted alkoxy (e.g., alkyl substituted with fluoro, such as —OCHF₂), CN, —NH—SO₂—R', —NO₂, —NH₂, —NH—C(O)—R', —C(O)—NH—R', —SO₂—R' and SO₂NR'R';

each occurrence of R' is independently selected from H, hydroxy, halogen, carboxyl, cyano, nitro, oxo(=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclcyalkyl, substituted or unsubstituted aryl, substituted or unsubstituted arylalkyl, substituted or unsubstituted heteroaryl, and substituted or unsubstituted heteroarylalkyl;

R⁴ is H or substituted or unsubstituted alkyl;

with the proviso that the compound is not selected from

1(2H)-Isoquinolinone, 3-[[4-amino-3-(3-hydroxyphenyl)-1H-pyrazolo[3,4-d]pyrimidin-1-yl]methyl]-8-methyl-2-phenyl;

1(2H)-Isoquinolinone, 3-[[4-amino-3-(3-hydroxyphenyl)-1H-pyrazolo[3,4-d]pyrimidin-1-yl]methyl]-8-fluoro-2-(2-fluorophenyl);

Benzamide, 3-[4-[[1,2-dihydro-8-methyl-2-(2-methylphenyl)-1-oxo-3-isoquinolinyl]methyl]-1H-pyrazolo[3,4-d]pyrimidin-3-yl];

3-[4-amino-1-[[1,2-dihydro-8-methyl-2-(2-methylphenyl)-1-oxo-3-isoquinolinyl]methyl]-1H-pyrazolo[3,4-d]pyrimidin-3-yl]-N-methyl-Benzamide;

1(2H)-Isoquinolinone, 3-[[4-amino-3-[4-(aminomethyl)phenyl]-1H-pyrazolo[3,4-d]pyrimidin-1-yl]methyl]-8-methyl-2-(2-methylphenyl);

1(2H)-Isoquinolinone, 3-[[4-amino-3-(3-hydroxyphenyl)-1H-pyrazolo[3,4-d]pyrimidin-1-yl]methyl]-2-(2-chlorophenyl)-8-methyl;

1(2H)-Isoquinolinone, 3-[[4-amino-3-(3-hydroxyphenyl)-1H-pyrazolo[3,4-d]pyrimidin-1-yl]methyl]-2-(2-ethylphenyl)-8-methyl;

1(2H)-Isoquinolinone, 3-[[4-amino-3-(3-hydroxyphenyl)-1H-pyrazolo[3,4-d]pyrimidin-1-yl]methyl]-8-methyl-2-[2-(1-methylethyl)phenyl];

1(2H)-Isoquinolinone, 3-[[4-amino-3-(3-hydroxyphenyl)-1H-pyrazolo[3,4-d]pyrimidin-1-yl]methyl]-8-fluoro-2-(2-methylphenyl);

1(2H)-Isoquinolinone, 3-[[4-amino-3-(4-fluoro-3-hydroxyphenyl)-1H-pyrazolo[3,4-d]pyrimidin-1-yl]methyl]-8-fluoro-2-(2-methylphenyl);

1(2H)-Isoquinolinone, 3-[[4-amino-3-(4-fluoro-3-hydroxyphenyl)-1H-pyrazolo[3,4-d]pyrimidin-1-yl]methyl]-2-(2-methylphenyl);

1(2H)-Isoquinolinone, 3-[[4-amino-3-(4-chloro-3-hydroxyphenyl)-1H-pyrazolo[3,4-d]pyrimidin-1-yl]methyl]-2-(2-methylphenyl);

1(2H)-Isoquinolinone, 3-[[4-amino-3-(3-hydroxyphenyl)-1H-pyrazolo[3,4-d]pyrimidin-1-yl]methyl]-2-(2-methylphenyl);

1(2H)-Isoquinolinone, 3-[[4-amino-3-(4-chlorophenyl)-1H-pyrazolo[3,4-d]pyrimidin-1-yl]methyl]-8-methyl-2-(2-methylphenyl);

1(2H)-Isoquinolinone, 3-[[4-amino-3-(3,4-dimethoxyphenyl)-1H-pyrazolo[3,4-d]pyrimidin-1-yl]methyl]-2-(2-fluorophenyl)-8-methyl;

1(2H)-Isoquinolinone, 3-[[4-amino-3-(4-hydroxyphenyl)-1H-pyrazolo[3,4-d]pyrimidin-1-yl]methyl]-2-(2-fluorophenyl)-8-methyl;

1(2H)-Isoquinolinone, 3-[[4-amino-3-(4-methoxyphenyl)-1H-pyrazolo[3,4-d]pyrimidin-1-yl]methyl]-8-methyl-2-(2-methylphenyl);

1(2H)-Isoquinolinone, 3-[[4-amino-3-(3,4-dimethoxyphenyl)-1H-pyrazolo[3,4-d]pyrimidin-1-yl]methyl]-8-methyl-2-(2-methylphenyl);

1(2H)-Isoquinolinone, 3-[[4-amino-3-(3-fluorophenyl)-1H-pyrazolo[3,4-d]pyrimidin-1-yl]methyl]-8-methyl-2-(2-methylphenyl);

1(2H)-Isoquinolinone, 3-[[4-amino-3-(3-fluorophenyl)-1H-pyrazolo[3,4-d]pyrimidin-1-yl]methyl]-2-(2-fluorophenyl)-8-methyl;

1(2H)-Isoquinolinone, 3-[[4-amino-3-(3-chlorophenyl)-1H-pyrazolo[3,4-d]pyrimidin-1-yl]methyl]-8-methyl-2-(2-methylphenyl);

1(2H)-Isoquinolinone, 3-[[4-amino-3-(3-chlorophenyl)-1H-pyrazolo[3,4-d]pyrimidin-1-yl]methyl]-2-(2-fluorophenyl)-8-methyl;

1(2H)-Isoquinolinone, 3-[[4-amino-3-(4-hydroxyphenyl)-1H-pyrazolo[3,4-d]pyrimidin-1-yl]methyl]-8-methyl-2-(2-methylphenyl);

1(2H)-Isoquinolinone, 3-[[4-amino-3-(3-fluoro-4-hydroxyphenyl)-1H-pyrazolo[3,4-d]pyrimidin-1-yl]methyl]-8-methyl-2-(2-methylphenyl);

1(2H)-Isoquinolinone, 3-[[4-amino-3-(3-fluoro-4-hydroxyphenyl)-1H-pyrazolo[3,4-d]pyrimidin-1-yl]methyl]-2-(2-fluorophenyl)-8-methyl;

1(2H)-Isoquinolinone, 3-[[4-amino-3-(4-fluorophenyl)-1H-pyrazolo[3,4-d]pyrimidin-1-yl]methyl]-8-methyl-2-(2-methylphenyl);

1(2H)-Isoquinolinone, 3-[[4-amino-3-(3-chloro-4-hydroxyphenyl)-1H-pyrazolo[3,4-d]pyrimidin-1-yl]methyl]-2-(2-fluorophenyl)-8-methyl;

1(2H)-Isoquinolinone, 3-[[4-amino-3-(3-chloro-4-hydroxyphenyl)-1H-pyrazolo[3,4-d]pyrimidin-1-yl]methyl]-8-methyl-2-(2-methylphenyl);

1(2H)-Isoquinolinone, 3-[[4-amino-3-(4-chloro-3-hydroxyphenyl)-1H-pyrazolo[3,4-d]pyrimidin-1-yl]methyl]-2-(2-fluorophenyl)-8-methyl;

1(2H)-Isoquinolinone, 3-[[4-amino-3-(4-chloro-3-hydroxyphenyl)-1H-pyrazolo[3,4-d]pyrimidin-1-yl]methyl]-8-methyl-2-(2-methylphenyl);

1(2H)-Isoquinolinone, 3-[[4-amino-3-(4-chloro-3-methoxyphenyl)-1H-pyrazolo[3,4-d]pyrimidin-1-yl]methyl]-2-(2-fluorophenyl)-8-methyl;

1(2H)-Isoquinolinone, 3-[[4-amino-3-(4-chloro-3-methoxyphenyl)-1H-pyrazolo[3,4-d]pyrimidin-1-yl]methyl]-8-methyl-2-(2-methylphenyl);

1(2H)-Isoquinolinone, 3-[[4-amino-3-(4-fluoro-3-hydroxyphenyl)-1H-pyrazolo[3,4-d]pyrimidin-1-yl]methyl]-8-methyl-2-(2-methylphenyl);

1(2H)-Isoquinolinone, 3-[[4-amino-3-(3-hydroxyphenyl)-1H-pyrazolo[3,4-d]pyrimidin-1-yl]methyl]-2-(2-fluorophenyl)-8-methyl;

1(2H)-Isoquinolinone, 3-[[4-amino-3-(4-fluoro-3-hydroxyphenyl)-1H-pyrazolo[3,4-d]pyrimidin-1-yl]methyl]-2-(2-fluorophenyl)-8-methyl;

1(2H)-Isoquinolinone, 3-[[4-amino-3-(3-methoxyphenyl)-1H-pyrazolo[3,4-d]pyrimidin-1-yl]methyl]-8-methyl-2-(2-methylphenyl);

1(2H)-Isoquinolinone, 3-[[4-amino-3-(3-hydroxyphenyl)-1H-pyrazolo[3,4-d]pyrimidin-1-yl]methyl]-8-methyl-2-(2-methylphenyl);

Benzenesulfonamide, 3-[4-amino-1-[[3,4-dihydro-5-methyl-3-(2-methylphenyl)-4-oxo-2-quinazolinyl]methyl]-1H-pyrazolo[3,4-d]pyrimidin-3-yl];

Benzonitrile, 3-[4-amino-1-[[3,4-dihydro-5-methyl-3-(2-methylphenyl)-4-oxo-2-quinazolinyl]methyl]-1H-pyrazolo[3,4-d]pyrimidin-3-yl];

4(3H)-Quinazolinone, 2-[[4-amino-3-(3-fluoro-4-methoxyphenyl)-1H-pyrazolo[3,4-d]pyrimidin-1-yl]methyl]-5-methyl-3-(2-methylphenyl);

4(3H)-Quinazolinone, 2-[[4-amino-3-(4-fluoro-3-hydroxyphenyl)-1H-pyrazolo[3,4-d]pyrimidin-1-yl]methyl]-5-methyl-3-(2-methylphenyl);

4(3H)-Quinazolinone, 2-[[4-amino-3-(4-chloro-3-hydroxyphenyl)-1H-pyrazolo[3,4-d]pyrimidin-1-yl]methyl]-5-methyl-3-(2-methylphenyl);

4(3H)-Quinazolinone, 2-[[4-amino-3-(4-methoxyphenyl)-1H-pyrazolo[3,4-d]pyrimidin-1-yl]methyl]-5-methyl-3-(2-methylphenyl);

4(3H)-Quinazolinone, 2-[[4-amino-3-(3-fluoro-4-hydroxyphenyl)-1H-pyrazolo[3,4-d]pyrimidin-1-yl]methyl]-5-methyl-3-(2-methylphenyl);

4(3H)-Quinazolinone, 2-[[4-amino-3-[4-(phenylmethoxy)phenyl]-1H-pyrazolo[3,4-d]pyrimidin-1-yl]methyl]-5-methyl-3-(2-methylphenyl);

4(3H)-Quinazolinone, 2-[[4-amino-3-(4-phenoxyphenyl)-1H-pyrazolo[3,4-d]pyrimidin-1-yl]methyl]-5-methyl-3-(2-methylphenyl);

4(3H)-Quinazolinone, 2-[[4-amino-3-(3,4-dimethoxyphenyl)-1H-pyrazolo[3,4-d]pyrimidin-1-yl]methyl]-5-methyl-3-(2-methylphenyl);

4(3H)-Quinazolinone, 2-[[4-amino-3-(3-hydroxyphenyl)-1H-pyrazolo[3,4-d]pyrimidin-1-yl]methyl]-3-(2-chlorophenyl)-5-methyl; and 4(3H)-Quinazolinone, 2-[[4-amino-3-(3-hydroxyphenyl)-1H-pyrazolo[3,4-d]pyrimidin-1-yl]methyl]-5-methyl-3-(2-methylphenyl).

In another embodiment, the present invention relates to a compound of formula (I):

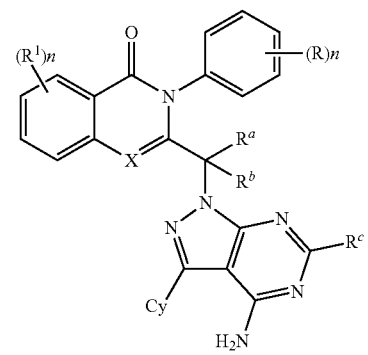

or a tautomer thereof, N-oxide thereof, pharmaceutically acceptable ester thereof, prodrug thereof, or pharmaceutically acceptable salt thereof, wherein each occurrence of $R^1$ is independently H, substituted or unsubstituted alkyl, substituted or unsubstituted alkenyl, substituted or unsubstituted alkynyl or halogen;

X is CH or N;

each occurrence of R is independently H, substituted or unsubstituted alkyl, or halogen;

$R^a$ and $R^b$ are independently selected from H and substituted or unsubstituted alkyl;

$R^c$ is H, substituted or unsubstituted alkyl, —$NH_2$ or halogen;

each occurrence of n is independently selected from 0, 1, 2, 3 and 4; and

Cy is selected from

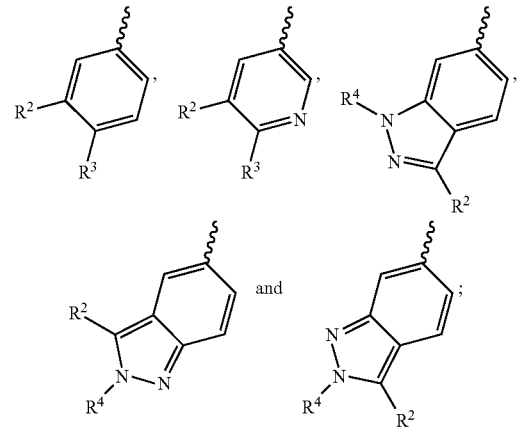

wherein $R^2$ and $R^3$ are independently selected from H, halogen, hydroxyl, substituted or unsubstituted alkyl, substituted or unsubstituted alkoxy (e.g., alkyl substituted with fluoro, such as —$OCHF_2$), CN, —NH—$SO_2$—R', —$NO_2$, —$NH_2$, —NH—C(O)—R', —C(O)—NH—R', —$SO_2$—R' and —$SO_2$NR'R';

each occurrence of R' is independently selected from H, hydroxy, halogen, carboxyl, cyano, nitro, oxo(=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclcyalkyl, substituted or unsubstituted aryl, substituted or unsubstituted arylalkyl, substituted or unsubstituted heteroaryl, and substituted or unsubstituted heteroarylalkyl;

$R^4$ is H or substituted or unsubstituted alkyl;

with the provisos that (i) when $R^a$ and $R^b$ are H, X is CH, Cy is

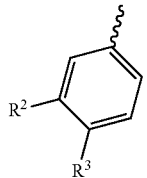

and $R^3$ is H, then $R^2$ is not —OH, F, Cl, —C(=O) NH$_2$, or —OCH$_3$;

(ii) when $R^a$ and $R^b$ are H, X is CH, Cy is

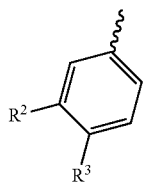

and $R^2$ is H, then $R^3$ is not CH$_2$—NH$_2$, Cl, OH or —OCH$_3$;

(iii) when $R^a$ and $R^b$ are H, X is CH or N, Cy is

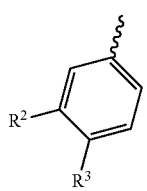

and $R^2$ is OH, —O—CH$_3$ or F, then $R^3$ is not F, Cl, OH or —O—CH$_3$ (iv) when $R^a$ and $R^b$ are H, X is N, Cy is

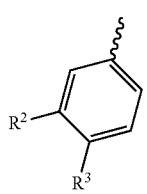

and $R^3$ is H, then $R^2$ is not —OH or —SO$_2$NH$_2$; and (v) when $R^a$ and $R^b$ are H, X is N, Cy is

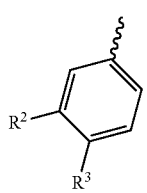

and $R^2$ is H, then $R^3$ is —OCH$_3$, —O—CH$_2$-Ph, or —O-Ph.

Yet another embodiment is a compound having the formula (I-A) or (I-B):

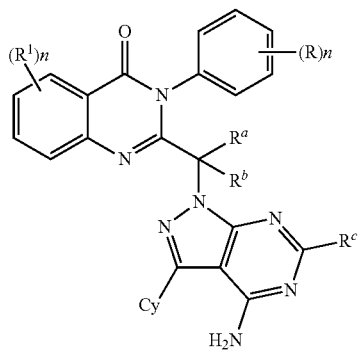
(I-A)

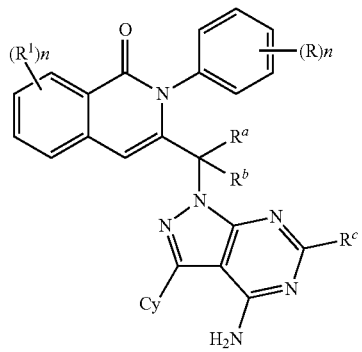
(I-B)

or a tautomer thereof, N-oxide thereof, pharmaceutically acceptable ester thereof, prodrug thereof, or pharmaceutically acceptable salt thereof, wherein $R^1$, R, n, $R^a$, $R^b$, $R^c$ and Cy are as defined above in relation to the compound of formula (I).

Yet another embodiment is a compound having the formula (I-A1), (I-A2), (I-A3), (I-A4), (I-A5), (I-B1), (I-B2), (I-B3), (I-B4) or (I-B5):

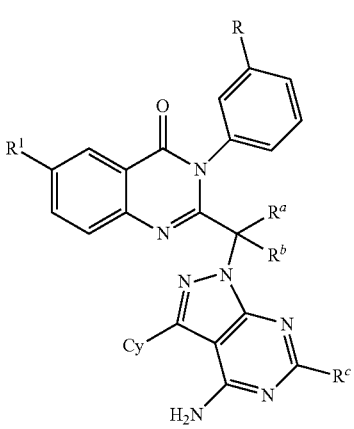
(I-A1)

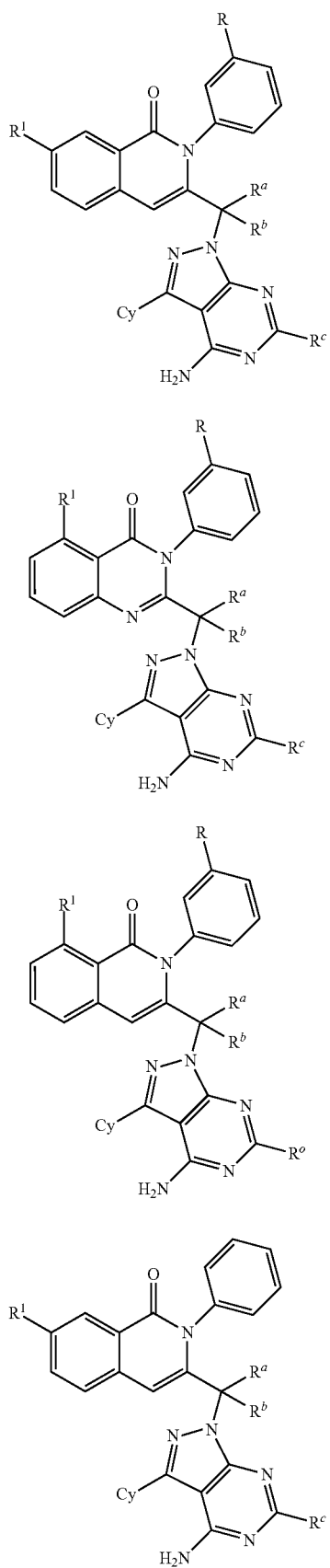
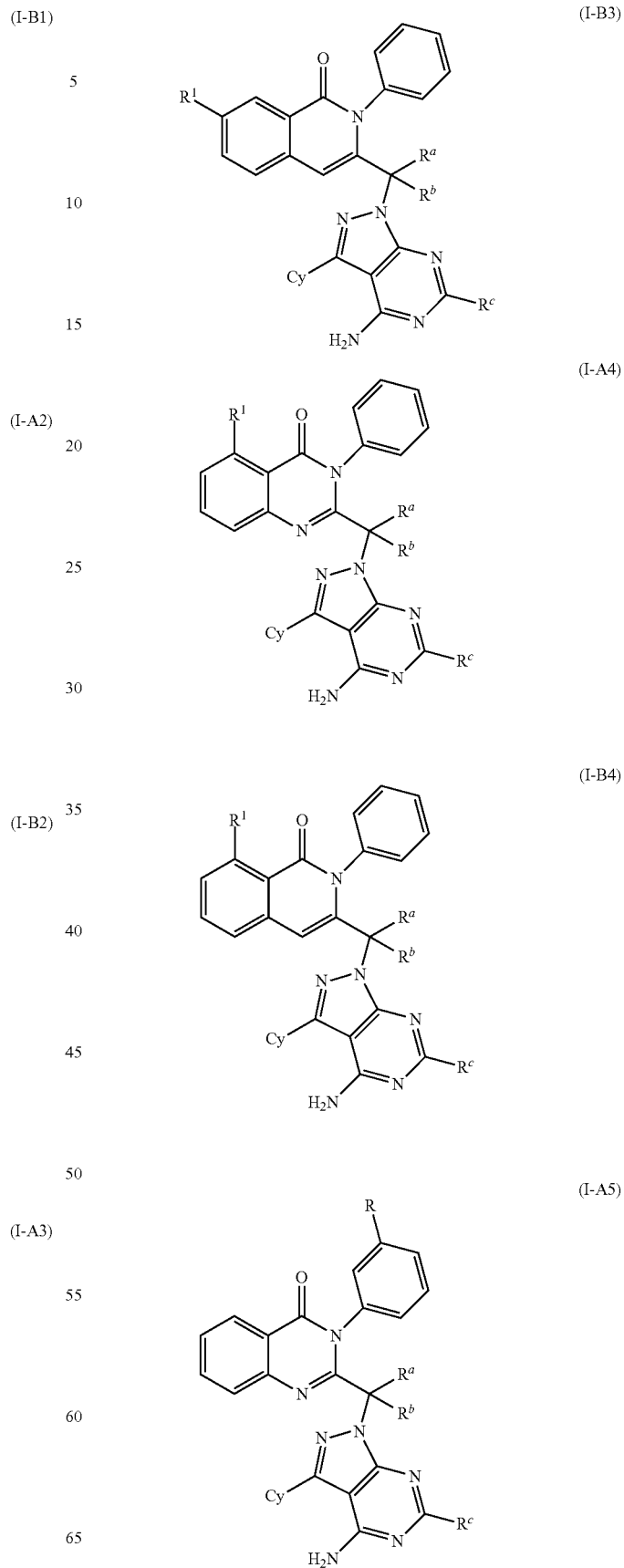

-continued (I-B5)

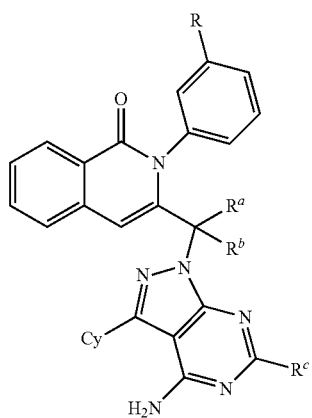

or a tautomer thereof, N-oxide thereof, pharmaceutically acceptable ester thereof, prodrug thereof, or pharmaceutically acceptable salt thereof, wherein $R^1$, R, $R^a$, $R^b$, $R^c$ and Cy are as defined above in relation to the compound of formula (I).

Yet another embodiment is a compound having the formula (II):

(II)

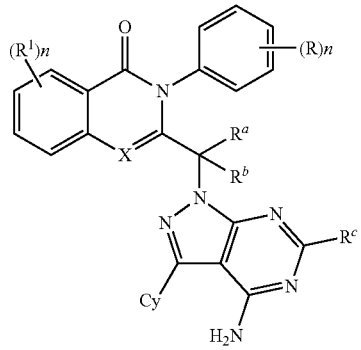

or a tautomer thereof, N-oxide thereof, pharmaceutically acceptable ester thereof, prodrug thereof, or pharmaceutically acceptable salt thereof, wherein $R^1$, X, R, n, $R^c$ and Cy are as defined above in relation to the compound of formula (I); and $R^a$ and $R^b$ are independently selected from H and substituted or unsubstituted alkyl, provided that when Cy is

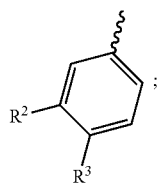

at least one of $R^a$ and $R^b$ is not hydrogen.

Yet another embodiment is a compound having the formula (II-1), (II-2), (II-3), (II-4) or (II-5):

(II-1)

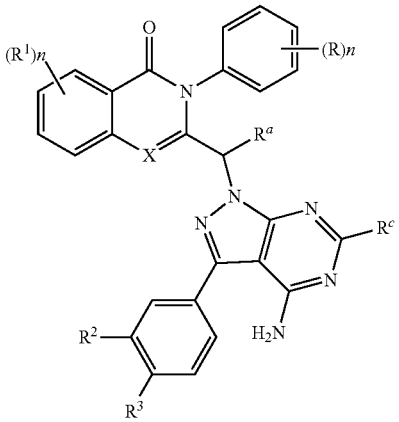

(II-2)

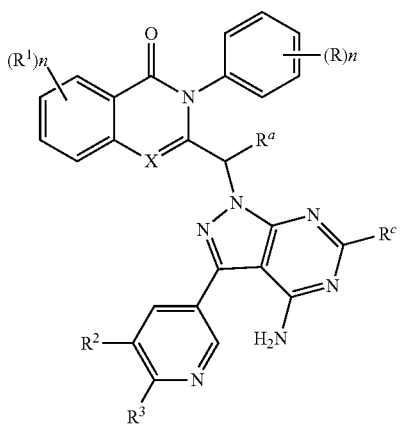

(II-3)

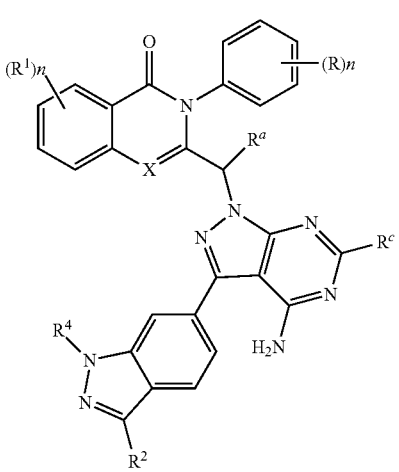

-continued

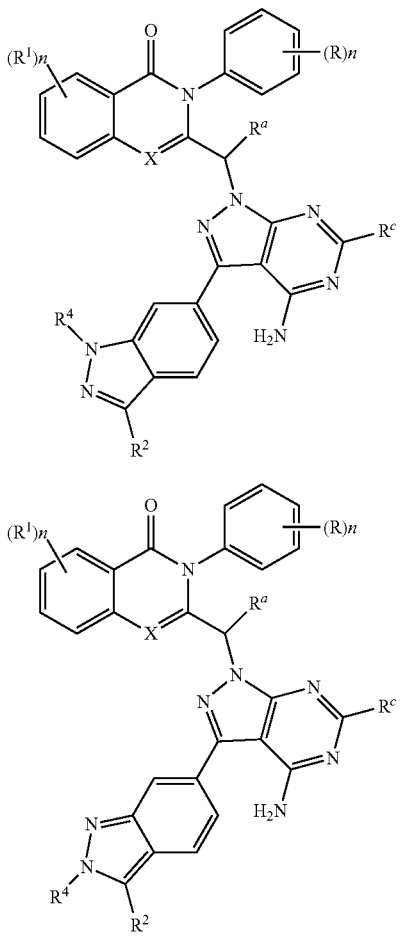

(II-4)

(II-5)

or a tautomer thereof, N-oxide thereof, pharmaceutically acceptable ester thereof, prodrug thereof, or pharmaceutically acceptable salt thereof, wherein $R^a$ is substituted or unsubstituted alkyl; and $R^1$, X, R, n, $R^c$, $R^2$, $R^3$ and $R^4$ are as defined above in relation to the compound formula (I).

Yet another embodiment is a compound having the formula (III):

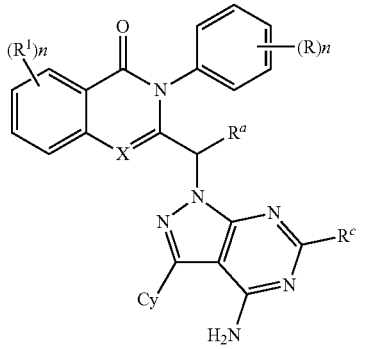

(III)

or a tautomer thereof, N-oxide thereof, pharmaceutically acceptable ester thereof, prodrug thereof, or pharmaceutically acceptable salt thereof, wherein $R^a$ is substituted or unsubstituted alkyl; and $R^1$, R, X, n, $R^a$ and Cy are as defined above in relation to the compound of formula (I)

Yet another embodiment is a compound having the formula (III-A) and (III-B):

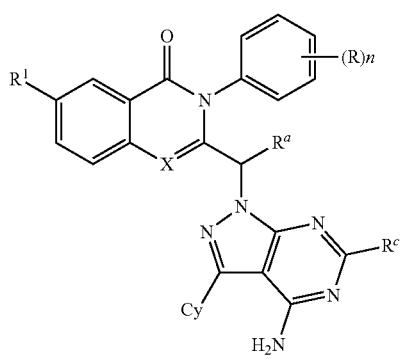

(III-A)

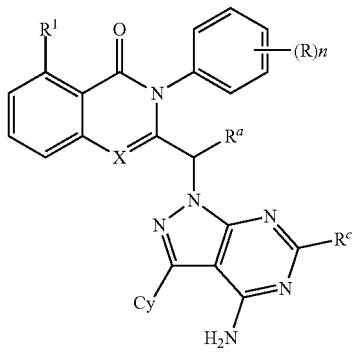

(III-B)

or a tautomer thereof, N-oxide thereof, pharmaceutically acceptable ester thereof, prodrug thereof, or pharmaceutically acceptable salt thereof, wherein $R^a$ is substituted or unsubstituted alkyl;

Cy is selected from

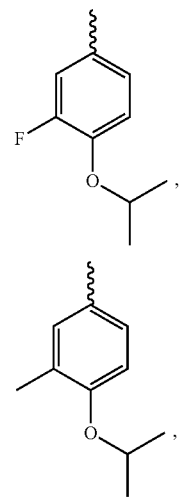

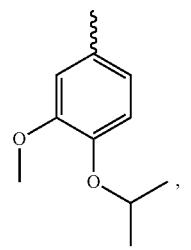
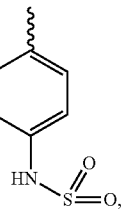
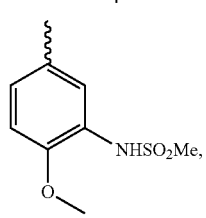
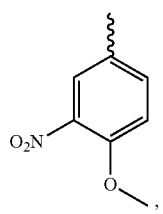
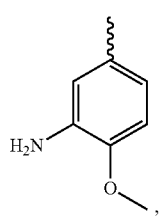
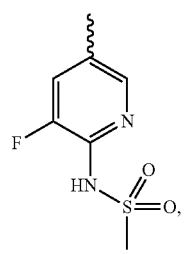
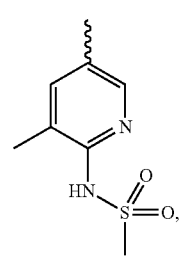
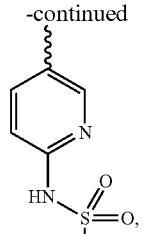
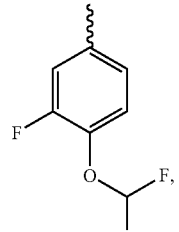
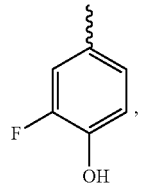
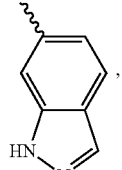
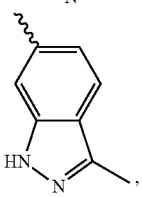
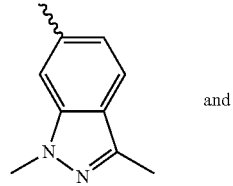
and
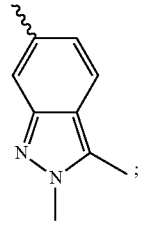
and
$R^1$, R, $R^e$, X and Cy are as defined above in relation to the compound of formula (I)
A preferred embodiment is a compound having the formula (I), (I-A), (I-A1), (I-A2), (I-A3), (I-A4), (I-A5), (I-B), (I-B1), (I-B2), (I-B3), (I-B4), (I-B5), (II), (II-1), (II-2), (II-3), (II-4), (II-5), (III), (III-A) or (III-B), wherein Cy is selected from

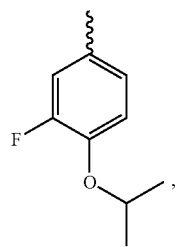
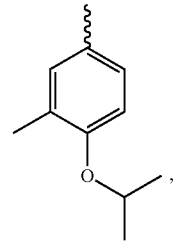
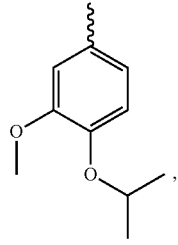
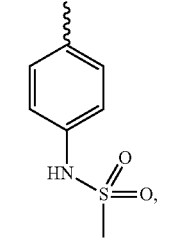
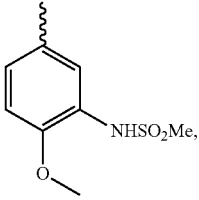
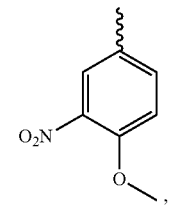
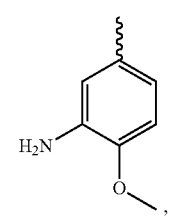
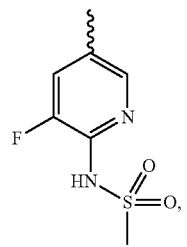
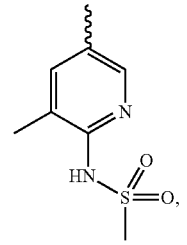
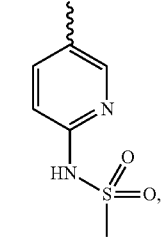
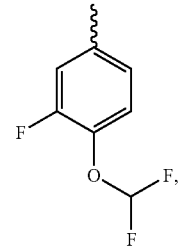
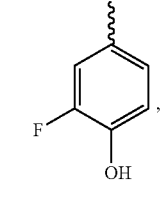
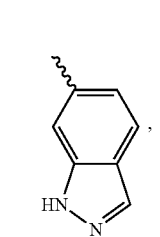
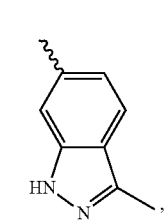

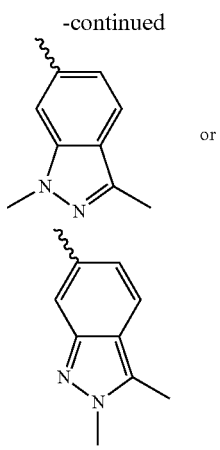

Another preferred embodiment is a compound having the formula (I), (I-A), (I-A1), (I-A2), (I-A3), (I-A4), (I-A5), (I-B), (I-B1), (I-B2), (I-B3), (I-B4), (I-B5), (II), (II-1), (I-2), (II-3), (II-4), (II-5), (III), (III-A) and (III-B), wherein $R^c$ is H, F or $NH_2$.

Another preferred embodiment is a compound having the formula (I), (I-A), (I-A1), (I-A2), (I-A3), (I-A4), (I-A5), (I-B), (I-B1), (I-B2), (I-B3), (I-B4), (I-B5), (II-1), (II-2), (II-3), (II-4), (II-5), (III), (III-A) and (III-B) wherein $R^a$ is H and $R^b$ is H, methyl or ethyl.

Another preferred embodiment is a compound having the formula (I), (I-A), (I-A1), (I-A2), (I-A3), (I-A4), (I-A5), (I-B), (I-B1), (I-B2), (I-B3), (I-B4), (I-B5), (II), (II-1), (II-2), (II-3), (II-4), (II-5), (III), (III-A) and (III-B) wherein $R^a$ is H and $R^b$ is methyl.

Another preferred embodiment is a compound having the formula (I), (I-A), (I-A1), (I-A2), (I-A5), (I-B), (I-B1), (I-B2), (I-B5), (II), (II-1), (II-2), (II-3), (II-4), (II-5), (III), (III-A) and (III-B), wherein R is H or halogen, preferably F.

Another preferred embodiment is a compound having the formula (I), (I-A), (I-A1), (I-A2), (I-A3), (I-A4), (I-B), (I-B1), (I-B2), (I-B3), (I-B5), (II), (II-1), (II-2), (II-3), (II-4), (II-5), (III), (III-A) and (III-B), wherein $R^1$ is H or halogen, preferably F.

Another preferred embodiment is a compound having the formula (I), (I-A), (I-B), (II), (II-1), (II-2), (II-3), (II-4), (II-5), (III), (III-A) and (III-B) wherein n is 0 or 1.

Yet another embodiment is a compound having the formula (I), (II), (II-1), (II-2), (II-3), (II-4), (II-5), (III), (III-A) and (III-B) wherein X is CH.

Yet another embodiment is a compound having the formula (I), (II), (II-1), (II-2), (II-3), (II-4), (II-5), (III), (III-A) and (III-B) wherein X is N.

Compounds of the present invention include those recited below (and in Table 1), and pharmaceutically acceptable salts thereof. The present invention should not be construed to be limited to these specific compounds.

1. 3-(1-(4-amino-3-(3-fluoro-4-isopropoxyphenyl)-1H-pyrazolo[3,4-d]pyrimidin-1-yl)ethyl)-8-chloro-2-phenylisoquinolin-1(2H)-one;
2. 3-(1-(4-amino-3-(3-fluoro-4-isopropoxyphenyl)-1H-pyrazolo[3,4-d]pyrimidin-1-yl)ethyl)-8-fluoro-2-phenylisoquinolin-1(2H)-one;
3. 2-(1-(4-amino-3-(3-fluoro-4-isopropoxyphenyl)-1H-pyrazolo[3,4-d]pyrimidin-1-yl)ethyl)-5-fluoro-3-phenylquinazolin-4(3H)-one;
4. 2-(1-(4-amino-3-(3-fluoro-4-isopropoxyphenyl)-1H-pyrazolo[3,4-d]pyrimidin-1-yl)ethyl)-6-fluoro-3-phenylquinazolin-4(3H)-one;
5. 3-(1-(4-amino-3-(3-fluoro-4-isopropoxyphenyl)-1H-pyrazolo[3,4-d]pyrimidin-1-yl)ethyl)-2-phenylisoquinolin-1(2H)-one;
5a. (+)-3-(1-(4-amino-3-(3-fluoro-4-isopropoxyphenyl)-1H-pyrazolo[3,4-d]pyrimidin-1-yl)ethyl)-2-phenylisoquinolin-1(2H)-one;
5b. (−)-3-(1-(4-amino-3-(3-fluoro-4-isopropoxyphenyl)-1H-pyrazolo[3,4-d]pyrimidin-1-yl)ethyl)-2-phenylisoquinolin-1(2H)-one;
6. 2-(1-(4-amino-3-(3-fluoro-4-isopropoxyphenyl)-1H-pyrazolo[3,4-d]pyrimidin-1-yl)ethyl)-3-phenylquinazolin-4(3H)-one;
6a. (+)-2-(1-(4-amino-3-(3-fluoro-4-isopropoxyphenyl)-1H-pyrazolo[3,4-d]pyrimidin-1-yl)ethyl)-3-phenylquinazolin-4(3H)-one;
6b. (−)-2-(1-(4-amino-3-(3-fluoro-4-isopropoxyphenyl)-1H-pyrazolo[3,4-d]pyrimidin-1-yl)ethyl)-3-phenylquinazolin-4(3H)-one;
7. 3-(1-(4-amino-3-(3-fluoro-4-hydroxyphenyl)-1H-pyrazolo[3,4-d]pyrimidin-1-yl)ethyl)-2-phenylisoquinolin-1(2H)-one;
7a. (+)-3-(1-(4-amino-3-(3-fluoro-4-hydroxyphenyl)-1H-pyrazolo[3,4-d]pyrimidin-1-yl)ethyl)-2-phenylisoquinolin-1(2H)-one;
7b. (−)-3-(1-(4-amino-3-(3-fluoro-4-hydroxyphenyl)-1H-pyrazolo[3,4-d]pyrimidin-1-yl)ethyl)-2-phenylisoquinolin-1(2H)-one;
8. 2-(1-(4-amino-3-(3-fluoro-4-hydroxyphenyl)-1H-pyrazolo[3,4-d]pyrimidin-1-yl)ethyl)-3-phenylquinazolin-4(3H)-one;
9. N-(5-(4-amino-1-(1-(1-oxo-2-phenyl-1,2-dihydroisoquinolin-3-yl)ethyl)-1H-pyrazolo[3,4-d]pyrimidin-3-yl)-2-methoxyphenyl)methanesulfonamide
9a. (+)—N-(5-(4-amino-1-(1-(1-oxo-2-phenyl-1,2-dihydroisoquinolin-3-yl)ethyl)-1H-pyrazolo[3,4-d]pyrimidin-3-yl)-2-methoxyphenyl)methanesulfonamide;
9b. (−)—N-(5-(4-amino-1-(1-(1-oxo-2-phenyl-1,2-dihydroisoquinolin-3-yl)ethyl)-1H-pyrazolo[3,4-d]pyrimidin-3-yl)-2-methoxyphenyl)methanesulfonamide;
10. 2-(1-(4-amino-3-(4-methoxy-3-nitrophenyl)-1H-pyrazolo[3,4-d]pyrimidin-1-yl)ethyl)-3-phenylquinazolin-4(3H)-one;
11. 3-(1-(4-amino-3-(3-amino-4-methoxyphenyl)-1H-pyrazolo[3,4-d]pyrimidin-1-yl)ethyl)-2-phenylisoquinolin-1(2H)-one;
12. N-(5-(4-amino-1-(1-(4-oxo-3-phenyl-3,4-dihydroquinazolin-2-yl)ethyl)-1H-pyrazolo[3,4-d]pyrimidin-3-yl)-2-methoxyphenyl)methanesulfonamide;
13. 2-(1-(4-amino-3-(3-fluoro-4-hydroxyphenyl)-1H-pyrazolo[3,4-d]pyrimidin-1-yl)ethyl)-6-fluoro-3-phenylquinazolin-4(3H)-one;
14. 3-(1-(4-amino-3-(3-fluoro-4-hydroxyphenyl)-1H-pyrazolo[3,4-d]pyrimidin-1-yl)ethyl)-8-chloro-2-phenylisoquinolin-1(2H)-one;
14a. (+)-3-(1-(4-amino-3-(3-fluoro-4-hydroxyphenyl)-1H-pyrazolo[3,4-d]pyrimidin-1-yl)ethyl)-8-chloro-2-phenylisoquinolin-1(2H)-one;
14b. (−)-3-(1-(4-amino-3-(3-fluoro-4-hydroxyphenyl)-1H-pyrazolo[3,4-d]pyrimidin-1-yl)ethyl)-8-chloro-2-phenylisoquinolin-1(2H)-one;
15. 3-(1-(4-amino-3-(3-fluoro-4-hydroxyphenyl)-1H-pyrazolo[3,4-d]pyrimidin-1-yl)ethyl)-8-fluoro-2-phenylisoquinolin-1(2H)-one;
15a. (+)-3-(1-(4-amino-3-(3-fluoro-4-hydroxyphenyl)-1H-pyrazolo[3,4-d]pyrimidin-1-yl)ethyl)-8-fluoro-2-phenylisoquinolin-1(2H)-one;
15b. (−)-3-(1-(4-amino-3-(3-fluoro-4-hydroxyphenyl)-1H-pyrazolo[3,4-d]pyrimidin-1-yl)ethyl)-8-fluoro-2-phenylisoquinolin-1(2H)-one;
16. 2-(1-(4-amino-3-(3-fluoro-4-hydroxyphenyl)-1H-pyrazolo[3,4-d]pyrimidin-1-yl)ethyl)-5-fluoro-3-phenylquinazolin-4(3H)-one;
16a. (+)-2-(1-(4-amino-3-(3-fluoro-4-hydroxyphenyl)-1H-pyrazolo[3,4-d]pyrimidin-1-yl)ethyl)-5-fluoro-3-phenylquinazolin-4(3H)-one;

16b. (−)-2-(1-(4-amino-3-(3-fluoro-4-hydroxyphenyl)-1H-pyrazolo[3,4-d]pyrimidin-1-yl)ethyl)-5-fluoro-3-phenylquinazolin-4(3H)-one;

17. 3-(1-(4-amino-3-(4-(difluoromethoxy)-3-fluorophenyl)-1H-pyrazolo[3,4-d]pyrimidin-1-yl)ethyl)-8-chloro-2-phenylisoquinolin-1(2H)-one;

17a. (+)-3-(1-(4-amino-3-(4-(difluoromethoxy)-3-fluorophenyl)-1H-pyrazolo[3,4-d]pyrimidin-1-yl)ethyl)-8-chloro-2-phenylisoquinolin-1(2H)-one;

17b. (−)-3-(1-(4-amino-3-(4-(difluoromethoxy)-3-fluorophenyl)-1H-pyrazolo[3,4-d]pyrimidin-1-yl)ethyl)-8-chloro-2-phenylisoquinolin-1(2H)-one;

18. 3-(1-(4-amino-3-(4-methoxy-3-nitrophenyl)-1H-pyrazolo[3,4-d]pyrimidin-1-yl)ethyl)-8-chloro-2-phenylisoquinolin-1(2H)-one;

19. 3-(1-(4-amino-3-(3-amino-4-methoxyphenyl)-1H-pyrazolo[3,4-d]pyrimidin-1-yl)ethyl)-8-chloro-2-phenylisoquinolin-1(2H)-one;

20. N-(5-(4-amino-1-(1-(8-chloro-1-oxo-2-phenyl-1,2-dihydroisoquinolin-3-yl)ethyl)-1H-pyrazolo[3,4-d]pyrimidin-3-yl)-2-methoxyphenyl)methanesulfonamide;

20a. (+)—N-(5-(4-amino-1-(1-(8-chloro-1-oxo-2-phenyl-1,2-dihydroisoquinolin-3-yl)ethyl)-1H-pyrazolo[3,4-d]pyrimidin-3-yl)-2-methoxyphenyl)methanesulfonamide;

20b. (−)—N-(5-(4-amino-1-(1-(8-chloro-1-oxo-2-phenyl-1,2-dihydroisoquinolin-3-yl)ethyl)-1H-pyrazolo[3,4-d]pyrimidin-3-yl)-2-methoxyphenyl)methanesulfonamide;

21. 3-(1-(4-amino-3-(3-methyl-1H-indazol-6-yl)-1H-pyrazolo[3,4-d]pyrimidin-1-yl)ethyl)-8-chloro-2-phenylisoquinolin-1(2H)-one;

21a. (+)-3-(1-(4-amino-3-(3-methyl-1H-indazol-6-yl)-1H-pyrazolo[3,4-d]pyrimidin-1-yl)ethyl)-8-chloro-2-phenylisoquinolin-1(2H)-one;

21b. (−)-3-(1-(4-amino-3-(3-methyl-1H-indazol-6-yl)-1H-pyrazolo[3,4-d]pyrimidin-1-yl)ethyl)-8-chloro-2-phenylisoquinolin-1(2H)-one;

22. 2-{1-[4-Amino-3-(3-fluoro-4-isopropoxy-phenyl)-pyrazolo[3,4-d]pyrimidin-1-yl]-propyl}-3-phenyl-3H-quinazolin-4-one;

and pharmaceutically acceptable salts thereof.

TABLE 1

| Ex | Structure |
|---|---|
| 1 | 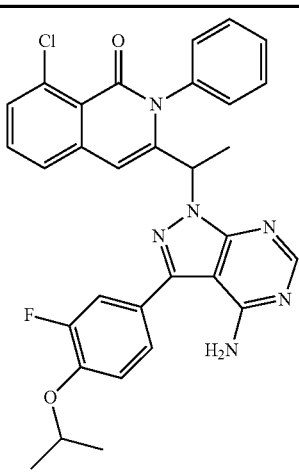 |
| 2 | 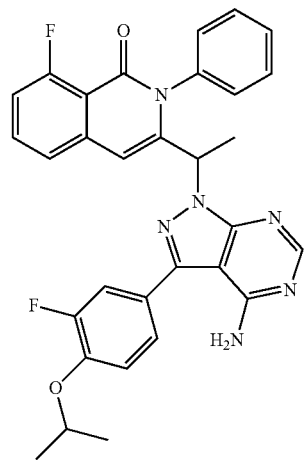 [SMILES: CC(C)Oc1ccc(-c2nn(C(C)c3cc4cccc(F)c4c(=O)n3-c3ccccc3)c3ncnc(N)c23)cc1F] |
| 3 | 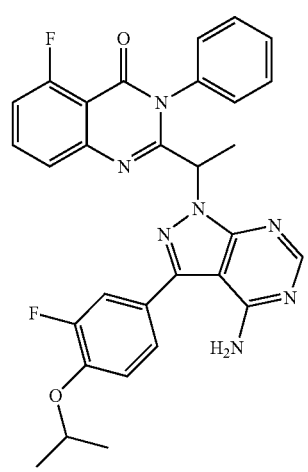 [SMILES: CC(C)Oc1ccc(-c2nn(C(C)c3nc4cccc(F)c4c(=O)n3-c3ccccc3)c3ncnc(N)c23)cc1F] |
| 4 | 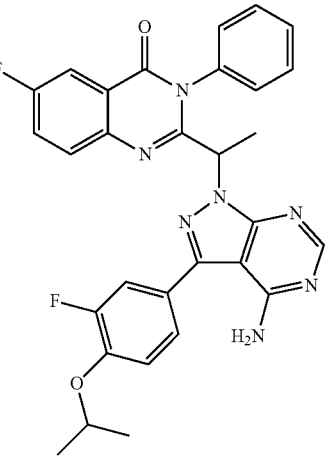 |

TABLE 1-continued
| Ex | Structure |
|---|---|
| 5 | 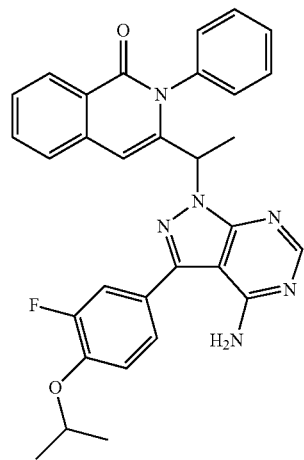 [SMILES: CC(C)Oc1ccc(-c2nn(C(C)c3cc4ccccc4c(=O)n3-c3ccccc3)c3ncnc(N)c23)cc1F] |
| 5a | 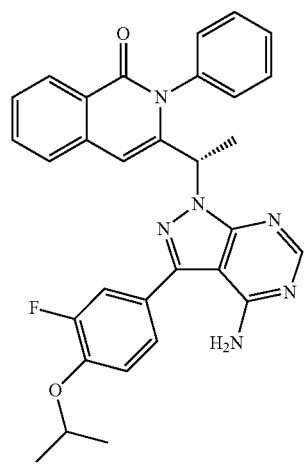 [SMILES: CC(C)Oc1ccc(-c2nn([C@@H](C)c3cc4ccccc4c(=O)n3-c3ccccc3)c3ncnc(N)c23)cc1F] |
| 5b | 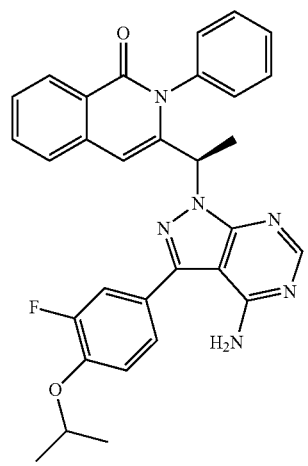 [SMILES: CC(C)Oc1ccc(-c2nn([C@H](C)c3cc4ccccc4c(=O)n3-c3ccccc3)c3ncnc(N)c23)cc1F] |
TABLE 1-continued
| Ex | Structure |
|---|---|
| 6 | 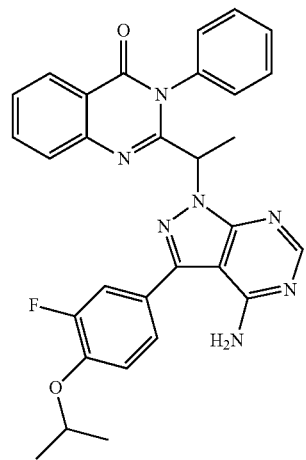 [SMILES: CC(C)Oc1ccc(-c2nn(C(C)c3nc4ccccc4c(=O)n3-c3ccccc3)c3ncnc(N)c23)cc1F] |
| 6a | 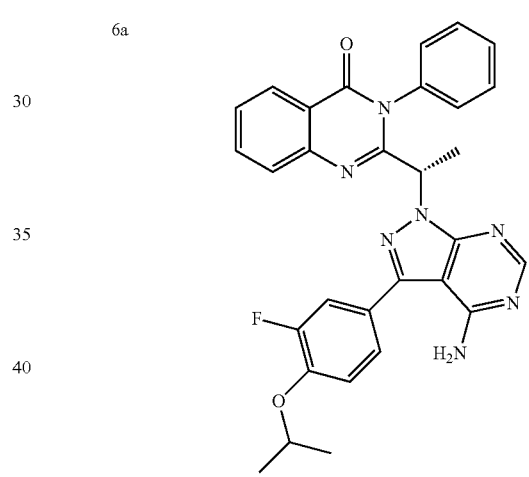 |
| 6b | 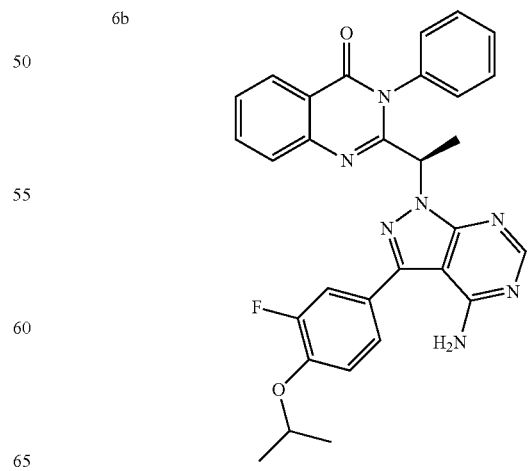 |

TABLE 1-continued

| Ex | Structure |
|---|---|
| 7 | (structure) |
| 7a | (structure) |
| 7b | (structure) |
| 8 | (structure) |
| 9 | (structure) |
| 9a | (structure) |
| 9b | (structure) |

TABLE 1-continued

| Ex | Structure |
|---|---|
| 10 | 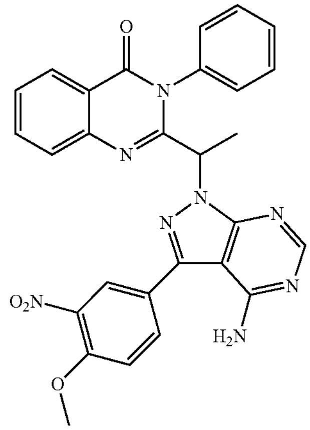 [SMILES: COc1ccc(-c2nn(C(C)c3nc4ccccc4c(=O)n3-c3ccccc3)c3ncnc(N)c23)cc1[N+](=O)[O-]] |
| 11 | 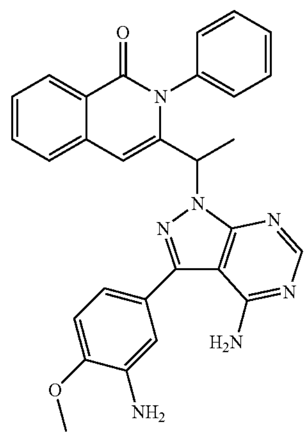 [SMILES: COc1ccc(-c2nn(C(C)c3cc4ccccc4c(=O)n3-c3ccccc3)c3ncnc(N)c23)cc1N] |
| 12 | 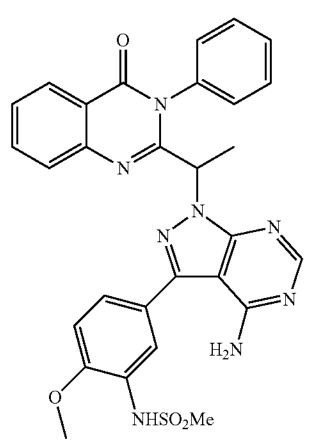 |
| 13 | 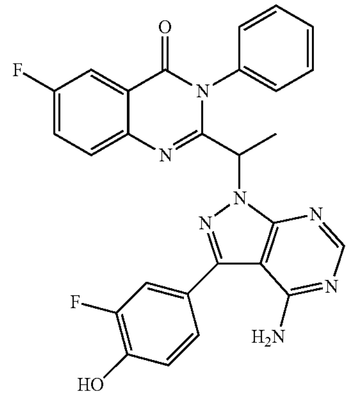 [SMILES: CC(c1nc2ccc(F)cc2c(=O)n1-c1ccccc1)n1nc(-c2ccc(O)c(F)c2)c2c(N)ncnc21] |
| 14 | 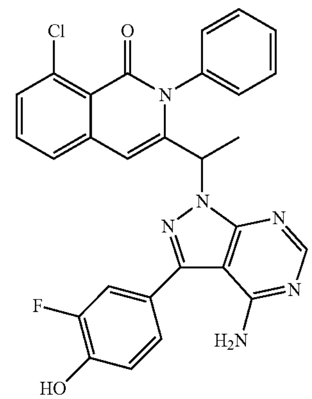 [SMILES: CC(c1cc2cccc(Cl)c2c(=O)n1-c1ccccc1)n1nc(-c2ccc(O)c(F)c2)c2c(N)ncnc21] |
| 14a | 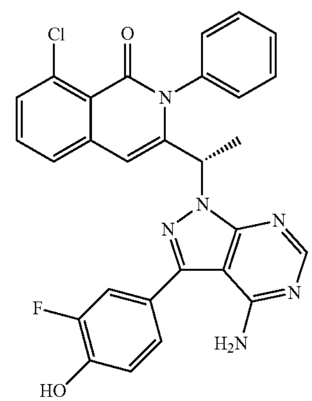 [SMILES: C[C@@H](c1cc2cccc(Cl)c2c(=O)n1-c1ccccc1)n1nc(-c2ccc(O)c(F)c2)c2c(N)ncnc21] |
| 14b | 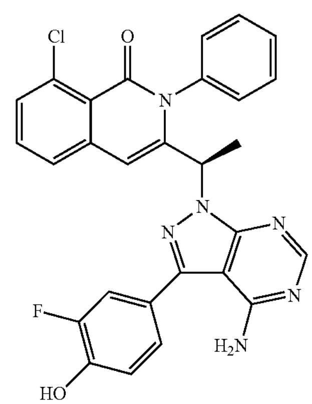 [SMILES: C[C@H](c1cc2cccc(Cl)c2c(=O)n1-c1ccccc1)n1nc(-c2ccc(O)c(F)c2)c2c(N)ncnc21] |

TABLE 1-continued

| Ex | Structure |
|---|---|
| 15 | 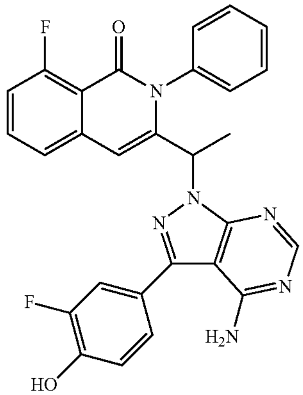 [SMILES: CC(c1cc2cccc(F)c2c(=O)n1-c1ccccc1)n1nc(-c2ccc(O)c(F)c2)c2c(N)ncnc21] |
| 15a | 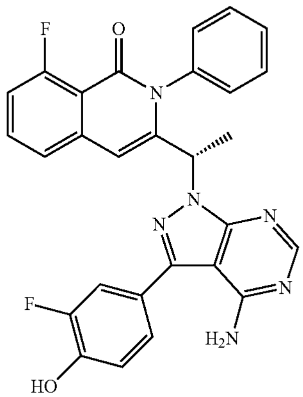 [SMILES: C[C@@H](c1cc2cccc(F)c2c(=O)n1-c1ccccc1)n1nc(-c2ccc(O)c(F)c2)c2c(N)ncnc21] |
| 15b | 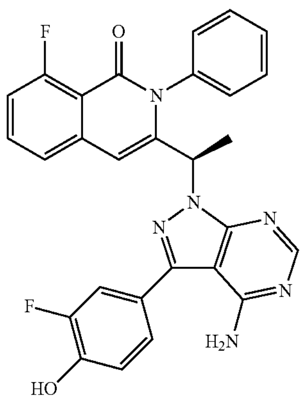 [SMILES: C[C@H](c1cc2cccc(F)c2c(=O)n1-c1ccccc1)n1nc(-c2ccc(O)c(F)c2)c2c(N)ncnc21] |
| 16 | 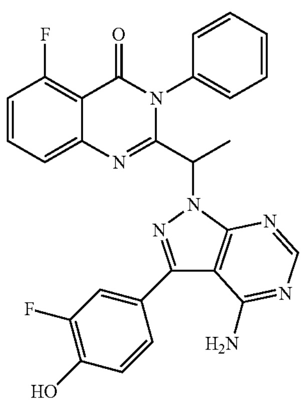 [SMILES: CC(c1nc2cccc(F)c2c(=O)n1-c1ccccc1)n1nc(-c2ccc(O)c(F)c2)c2c(N)ncnc21] |
| 16a | |
| 16b | |
| 17 | |

TABLE 1-continued
| Ex | Structure |
|---|---|
| 17a | 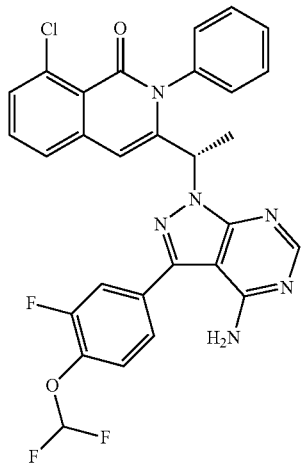 [SMILES: C[C@@H](c1cc2cccc(Cl)c2c(=O)n1-c1ccccc1)n1nc(-c2ccc(OC(F)F)c(F)c2)c2c(N)ncnc21] |
| 17b | 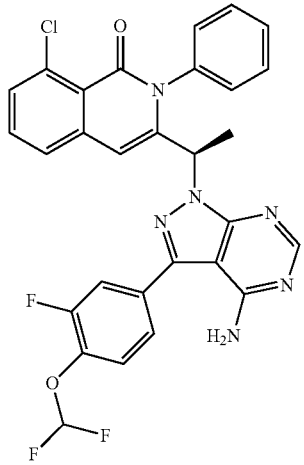 [SMILES: C[C@H](c1cc2cccc(Cl)c2c(=O)n1-c1ccccc1)n1nc(-c2ccc(OC(F)F)c(F)c2)c2c(N)ncnc21] |
| 18 | 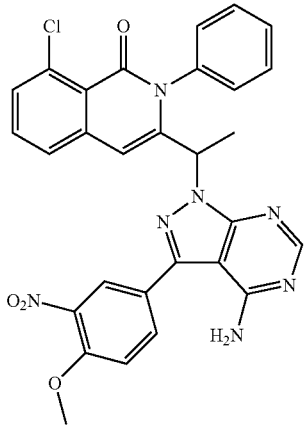 |
TABLE 1-continued
| Ex | Structure |
|---|---|
| 19 | 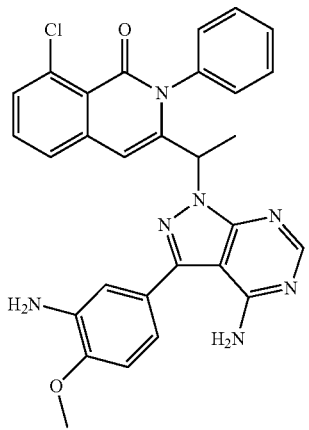 [SMILES: COc1ccc(-c2nn(C(C)c3cc4cccc(Cl)c4c(=O)n3-c3ccccc3)c3ncnc(N)c23)cc1[N+](=O)[O-]] |
| 20 | 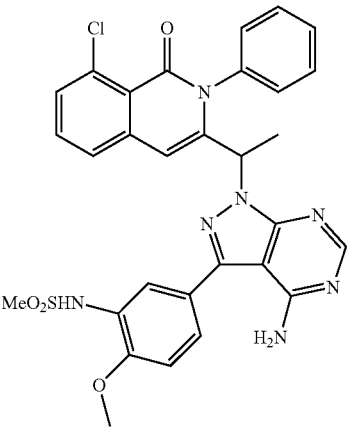 |
| 20a |  |

TABLE 1-continued

| Ex | Structure |
|---|---|
| 20b | (structure) |
| 21 | (structure) |
| 21a | (structure) |

TABLE 1-continued

| Ex | Structure |
|---|---|
| 21b | (structure) |
| 22 | (structure) |

Illustrative compounds of the present invention also include those recited below (and in Table 2), and pharmaceutically acceptable salts thereof. Again, the present invention should not be construed to be limited to these specific compounds.

i. 2-{1-[4-Amino-3-(3-fluoro-4-isopropoxy-phenyl)-pyrazolo[3,4-d]pyrimidin-1-yl]-ethyl}-6-fluoro-3-(3-fluorophenyl)-3H-quinazolin-4-one;

ii. 2-{1-[4-Amino-3-(3-fluoro-4-isopropoxy-phenyl)-pyrazolo[3,4-d]pyrimidin-1-yl]ethyl}-5-fluoro-3-(3-fluorophenyl)-3H-quinazolin-4-one;

iii. 2-{1-[4-Amino-3-(3-fluoro-4-isopropoxy-phenyl)-pyrazolo[3,4-d]pyrimidin-1-yl]-ethyl}-3-(3-fluoro-phenyl)-3H-quinazolin-4-one;

iv. 2-{1-[4-Amino-3-(3-fluoro-4-hydroxy-phenyl)-pyrazolo[3,4-d]pyrimidin-1-yl]-ethyl}-6-fluoro-3-(3-fluoro-phenyl)-3H-quinazolin-4-one;

v. 2-{1-[4-Amino-3-(3-fluoro-4-hydroxy-phenyl)-pyrazolo[3,4-d]pyrimidin-1-yl]-ethyl}-5-fluoro-3-(3-fluoro-phenyl)-3H-quinazolin-4-one;

vi. 2-{1-[4-Amino-3-(3-fluoro-4-hydroxy-phenyl)-pyrazolo[3,4-d]pyrimidin-1-yl]-ethyl}-3-(3-fluoro-phenyl)-3H-quinazolin-4-one;

vii. 3-{1-[4-Amino-3-(3-fluoro-4-isopropoxy-phenyl)-pyrazolo[3,4-d]pyrimidin-1-yl]-ethyl}-7-fluoro-2-(3-fluorophenyl)-2H-isoquinolin-1-one;

viii. 3-{1-[4-Amino-3-(3-fluoro-4-isopropoxy-phenyl)-pyrazolo[3,4-d]pyrimidin-1-yl]-ethyl}-8-fluoro-2-(3-fluoro-phenyl)-2H-isoquinolin-1-one;

ix. 3-{1-[4-Amino-3-(3-fluoro-4-isopropoxy-phenyl)-pyrazolo[3,4-d]pyrimidin-1-yl]-ethyl}-7-fluoro-2-phenyl-2H-isoquinolin-1-one;

x. 3-{1-[4-Amino-3-(3-fluoro-4-isopropoxy-phenyl)-pyrazolo[3,4-d]pyrimidin-1-yl]-ethyl}-2-(3-fluoro-phenyl)-2H-isoquinolin-1-one;

xi. 3-{1-[4-Amino-3-(3-fluoro-4-hydroxy-phenyl)-pyrazolo[3,4-d]pyrimidin-1-yl]-ethyl}-7-fluoro-2-(3-fluoro-phenyl)-2H-isoquinolin-1-one;

xii. 3-{1-[4-Amino-3-(3-fluoro-4-hydroxy-phenyl)-pyrazolo[3,4-d]pyrimidin-1-yl]-ethyl}-8-fluoro-2-(3-fluoro-phenyl)-2H-isoquinolin-1-one;

xiii. 3-{1-[4-Amino-3-(3-fluoro-4-hydroxy-phenyl)-pyrazolo[3,4-d]pyrimidin-1-yl]-ethyl}-7-fluoro-2-phenyl-2H-isoquinolin-1-one;

xiv. 3-{1-[4-Amino-3-(3-fluoro-4-hydroxy-phenyl)-pyrazolo[3,4-d]pyrimidin-1-yl]-ethyl}-2-(3-fluoro-phenyl)-2H-isoquinolin-1-one;

and pharmaceutically acceptable salts thereof.

TABLE 2

| Ex | Structure |
|---|---|
| i | 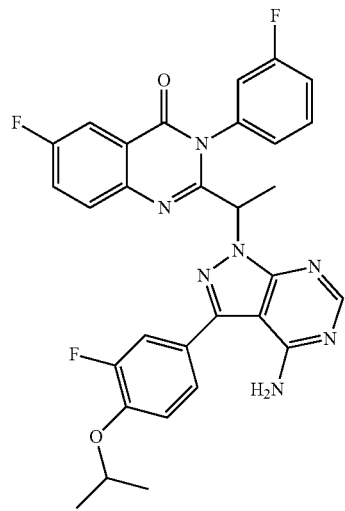 [SMILES: CC(C)Oc1ccc(-c2nn(C(C)c3nc4ccc(F)cc4c(=O)n3-c3cccc(F)c3)c3ncnc(N)c23)cc1F] |
| ii | 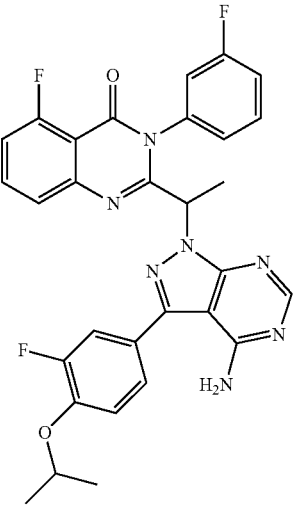 [SMILES: CC(C)Oc1ccc(-c2nn(C(C)c3nc4cccc(F)c4c(=O)n3-c3cccc(F)c3)c3ncnc(N)c23)cc1F] |

TABLE 2-continued

| Ex | Structure |
|---|---|
| iii | 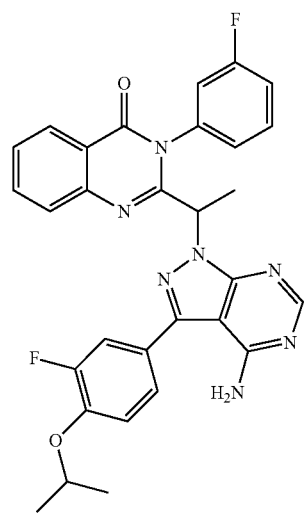 [SMILES: CC(C)Oc1ccc(-c2nn(C(C)c3nc4ccccc4c(=O)n3-c3cccc(F)c3)c3ncnc(N)c23)cc1F] |
| iv | 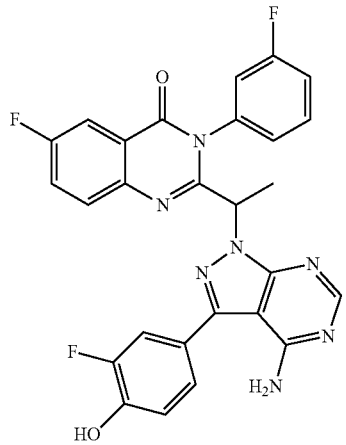 [SMILES: CC(c1nc2ccc(F)cc2c(=O)n1-c1cccc(F)c1)n1nc(-c2ccc(O)c(F)c2)c2c(N)ncnc21] |
| v | 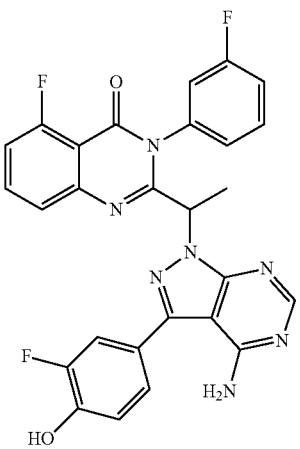 [SMILES: CC(c1nc2cccc(F)c2c(=O)n1-c1cccc(F)c1)n1nc(-c2ccc(O)c(F)c2)c2c(N)ncnc21] |

TABLE 2-continued

| Ex | Structure |
|---|---|
| vi | 2-(1-(4-amino-3-(3-fluoro-4-hydroxyphenyl)-1H-pyrazolo[3,4-d]pyrimidin-1-yl)ethyl)-3-(3-fluorophenyl)quinazolin-4(3H)-one |
| vii | 3-(1-(4-amino-3-(3-fluoro-4-isopropoxyphenyl)-1H-pyrazolo[3,4-d]pyrimidin-1-yl)ethyl)-7-fluoro-2-(3-fluorophenyl)isoquinolin-1(2H)-one |
| viii | 3-(1-(4-amino-3-(3-fluoro-4-isopropoxyphenyl)-1H-pyrazolo[3,4-d]pyrimidin-1-yl)ethyl)-8-fluoro-2-(3-fluorophenyl)isoquinolin-1(2H)-one |
| ix | 3-(1-(4-amino-3-(3-fluoro-4-isopropoxyphenyl)-1H-pyrazolo[3,4-d]pyrimidin-1-yl)ethyl)-7-fluoro-2-phenylisoquinolin-1(2H)-one |
| x | 3-(1-(4-amino-3-(3-fluoro-4-isopropoxyphenyl)-1H-pyrazolo[3,4-d]pyrimidin-1-yl)ethyl)-2-(3-fluorophenyl)isoquinolin-1(2H)-one |
| xi | 3-(1-(4-amino-3-(3-fluoro-4-hydroxyphenyl)-1H-pyrazolo[3,4-d]pyrimidin-1-yl)ethyl)-7-fluoro-2-(3-fluorophenyl)isoquinolin-1(2H)-one |

TABLE 2-continued

| Ex | Structure |
|---|---|
| xii | 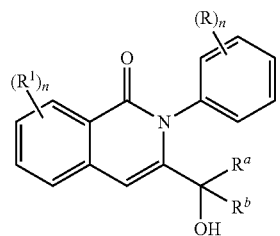 |
| xiii | 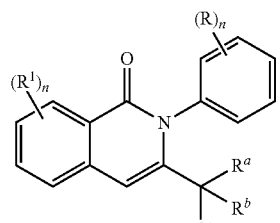 |
| xiv | 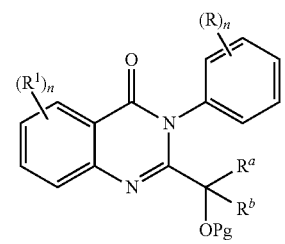 |

Yet another embodiment is a compound having the formula (a1), (a2), (c), (c2) or (d):

(a1)

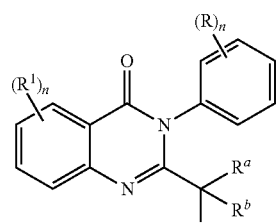

(a2)

(c)

(c2)

(d)

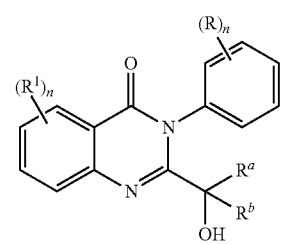

wherein $R^a$ and $R^b$ are independently selected from H and substituted or unsubstituted alkyl, provided that at least one of $R^a$ and $R^b$ is not H;

Pg is protecting group;

Lg is leaving group; and $R^1$, R, and n are as defined above in relation to the compound of formula (I).

In another aspect, the present invention relates to method of preparing a compound of formula (I), (I-A), (I-A1), (I-A2), (I-A3), (I-A4), (I-A5), (I-B), (I-B1), (I-B2), (I-B3), (I-B4), (I-B5), (II), (II-1), (II-2), (II-3), (II-4), (II-5), (III), (III-A) and (III-B), comprising converting a compound of formula (a1), (a2), (c), (c2) or (d) to a compound of formula (I), (I-A), (I-A1), (I-A2), (I-A3), (I-A4), (I-A5), (I-B), (I-B1), (I-B2), (I-B3), (I-B4), (I-B5), (II), (II-1), (II-2), (II-3), (II-4), (II-5), (III), (III-A) and (III-B), for example, as described in schemes 1 to 4 below.

Yet another embodiment of the present invention is a method for inhibiting PI3K (such as PI3K δ and/or γ) in a patient comprising administering to the patient an effective amount of at least one compound of the present invention, for example, a compound of formula (I), (I-A), (I-A1), (I-A2), (I-A4), (I-A5), (I-B), (I-B1), (I-B2), (I-B3), (I-B4), (I-B5), (II), (II-1), (II-2), (II-3), (II-4), (II-5), (III), (III-A) and (III-B), as defined above.

Yet another embodiment of the present invention is a method for treating an inflammatory, autoimmune or proliferative disease via modulation of a protein kinase (such as Pi3K δ and/or γ kinase) comprising administering to a patient in need of such treatment an effective amount of at least one compound of the present invention. In one embodiment, the compound of the present invention inhibits the PI3K δ protein kinase. In another embodiment, the compound of the present invention inhibits both the PI3K δ and γ protein kinases.

Yet another embodiment of the present invention is a method for treating an inflammatory, autoimmune or proliferative disease via modulation of a protein kinase (such as PI3K δ and/or γ kinase) comprising administering to a patient in need of such treatment an effective amount of at least one compound of the present invention, in combination (simultaneously or sequentially) with at least one other anti-inflammatory, immunomodulator or anti-cancer agent. In one embodiment, the compound of the present invention inhibits the PI3K δ protein kinase. In another embodiment, the compound of the present invention inhibits both the PI3K δ and γ protein kinase.

More particularly, the compounds of formula (I), (I-A), (I-A1), (I-A2), (I-A3), (I-A4), (I-A5), (I-B), (I-B1), (I-B2), (I-B3), (I-B4), (I-B5), (II), (II-1), (II-2), (II-3), (II-4), (II-5), (III), (III-A) and (III-B), and pharmaceutically acceptable esters or salts thereof, can be administered for the treatment, prevention and/or amelioration of PI3K and related protein kinase mediated diseases or disorders, in particular the amelioration of diseases or disorders mediated through PI3K δ and/or γ, including, but not limited to, inflammatory diseases or disorders, autoimmune diseases or disorders, cancer, and other proliferative diseases or disorders.

The compounds of the present invention are useful in the treatment of a variety of cancers, including, but not limited to, the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of protein kinases in the regulation of cellular proliferation in general, the protein kinase inhibitors of the present invention may act as reversible cytostatic agents, which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

The compounds of the present invention as modulators of apoptosis are useful in the treatment of cancer (including, but not limited to, those types mentioned above), viral infections (including, but not limited to herpevirus, poxvirus, Epstein-Barr virus, Sindbis virus and adenovirus), prevention of AIDS development in HIV-infected individuals, autoimmune diseases (including, but not limited, to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of present invention can modulate the level of cellular RNA and DNA synthesis. These agents are therefore useful in the treatment of viral infections (including, but not limited to, HIV, human papilloma virus, herpesvirus, poxvirus, Epstein-Barr virus, Sindbis virus and adenovirus).

The compounds of the present invention are useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse. The compounds described herein are also useful in inhibiting tumor angiogenesis and metastasis. One embodiment of the invention is a method of inhibiting tumor angiogenesis or metastasis in a patient in need thereof comprising administering an effective amount of one or more compounds of the present invention.

Another embodiment of the present invention is a method of treating an immune system-related disease (e.g., an autoimmune disease), a disease or disorder involving inflammation (e.g., asthma, chronic obstructive pulmonary disease, rheumatoid arthritis, inflammatory bowel disease, glomerulonephritis, neuroinflammatory diseases, multiple sclerosis, uveitis and disorders of the immune system), cancer or other proliferative disease, a hepatic disease or disorder, a renal disease or disorder. The method comprises administering an effective amount of one or more compounds of the present invention.

Examples of immune disorders include, but are not limited to, psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

In one embodiment, the compounds described herein are used as immunosuppresants to prevent transplant graft rejections, allogeneic or xenogeneic transplantation rejection (organ, bone marrow, stem cells, other cells and tissues), and graft-versus-host disease. In other embodiments, transplant graft rejections result from tissue or organ transplants. In further embodiments, graft-versus-host disease results from bone marrow or stem cell transplantation. One embodiment is a method of preventing or decreasing the risk of transplant graft rejection, allogeneic or xenogeneic transplantation rejection (organ, bone marrow, stem cells, other cells and tissues), or graft-versus-host disease comprising administering an effective amount of one or more compounds of the present invention.

The compounds of the present invention may also be administered in combination (simultaneously or sequentially) with known anti-cancer treatments, such as radiation therapy or with cytostatic or cytotoxic anticancer agents, such as, for example, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate, other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2), other protein kinase modulators, and combinations thereof.

The compounds of the present invention may also be administered in combination (simultaneously or sequentially) with one or more steroidal anti-inflammatory drugs, non-steroidal anti-inflammatory drugs (NSAIDs) or immune selective anti-inflammatory serivatives (ImSAIDs), and combinations thereof.

In a further aspect, the present invention relates to a pharmaceutical composition comprising one or more compounds of the present invention (such as a compound of formula (I), (I-A), (I-A1), (I-A2), (I-A3), (I-A4), (I-A5), (I-B), (I-B1), (I-B2), (I-B3), (I-B4), (I-B5), (II), (II-1), (II-2), (II-3), (II-4), (II-5), (III), (III-A) or (III-B) and a pharmaceutically acceptable carrier. The pharmaceutical composition may further comprise one or more of the active ingredients identified above, such as, e.g., additional steroidal anti-inflammatory drugs, non-steroidal anti-inflammatory drugs (NSAIDs) or immune selective anti-inflammatory derivatives (ImSAIDs), anti-cancer agents, and combinations thereof.

In one embodiment, the pharmaceutical composition comprises a therapeutically effective amount of one or more compounds of formula (I), (I-A), (I-A1), (I-A2), (I-A3), (I-A4), (I-A5), (I-B), (I-B1), (I-B2), (I-B3), (I-B4), (I-B5), (II), (II-1), (II-2), (II-3), (II-4), (II-5), (III), (III-A) or (III-B).

Yet another embodiment is a method of treating leukemia in a patient in need thereof comprising administering a therapeutically effective amount of a compound of the present invention. For example, the compounds of the present invention is effective for treating autoimmune disorders such as asthma, COPD, rhematoid arthritis, psorias, lupus and experimental autoimmune encephalomyelitis (EAE).

Yet another embodiment is a method of treating allergic rhinitis in a patient in need thereof comprising administering a therapeutically effective amount of a compound of the present invention.

Yet another embodiment is a method of treating leukemia in a patient in need thereof comprising administering a therapeutically effective amount of a compound of the present invention. For example, the compounds of the present invention are effective for treating chronic lymphocytic leukemia (CLL), non-Hodgkin lymphoma (NHL), acute myeloid leukemia (AML), multiple myeloma (MM), small lymphocytic lymphoma (SLL), and indolent non-Hodgkin's lymphoma (I-NHL).

DETAILED DESCRIPTION OF THE INVENTION

As used herein the following definitions shall apply unless otherwise indicated. Further many of the groups defined herein can be optionally substituted. The listing of substituents in the definition is exemplary and is not to be construed to limit the substituents defined elsewhere in the specification.

The term "alkyl", unless otherwise specified, refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl). The term "($C_{1-6}$) alkyl" refers to an alkyl group as defined above having up to 6 carbon atoms.

The term "alkenyl", unless otherwise specified, refers to an aliphatic hydrocarbon group containing a carbon-carbon double bond and which may be a straight or branched or branched chain having about 2 to about 10 carbon atoms, e.g., ethenyl, 1-propenyl, 2-propenyl (allyl), iso-propenyl, 2-methyl-1-propenyl, 1-butenyl, and 2-butenyl. The term "($C_{2-6}$)alkenyl" refers to an alkenyl group as defined above having up to 6 carbon atoms.

The term "alkynyl", unless otherwise specified, refers to a straight or branched chain hydrocarbyl radical having at least one carbon-carbon triple bond, and having in the range of 2 to up to 12 carbon atoms (with radicals having in the range of 2 to up to 10 carbon atoms presently being preferred) e.g., ethynyl, propynyl, and butanyl. The term "($C_{2-6}$) alkynyl" refers to an alkynyl group as defined above having up to 6 carbon atoms.

The term "alkoxy" unless otherwise specified, denotes an alkyl, cycloalkyl, or cycloalkylalkyl group as defined herein attached via an oxygen linkage to the rest of the molecule. The term "substituted alkoxy" refers to an alkoxy group where the alkyl constituent is substituted (i.e., —O-(substituted alkyl) wherein the term "substituted alkyl" is the same as defined above for "alkyl". For example "alkoxy" refers to the group —O-alkyl, including from 1 to 8 carbon atoms of a straight, branched, cyclic configuration and combinations thereof attached to the parent structure through oxygen. Examples include methoxy, ethoxy, propoxy, isopropoxy, cyclopropyloxy, and cyclohexyloxy.

The term "cycloalkyl", unless otherwise specified, denotes a non-aromatic mono or multicyclic ring system of about 3 to 12 carbon atoms such as cyclopropyl, cyclobutyl, cyclopentyl, and cyclohexyl. Examples of multicyclic cycloalkyl groups include perhydronaphthyl, adamantyl and norbornyl groups, bridged cyclic groups, and sprirobicyclic groups, e.g., sprio (4,4) non-2-yl. The term "($C_{3-8}$) cycloalkyl" refers to a cycloalkyl group as defined above having 3 to 8 carbon atoms.

The term "cycloalkylalkyl", unless otherwise specified, refers to a cyclic ring-containing radical containing in the range of about 3 up to 8 carbon atoms directly attached to an alkyl group which are then attached to the main structure at any carbon from the alkyl group that results in the creation of a stable structure such as cyclopropylmethyl, cyclobutylethyl, and cyclopentylethyl.

The term "cycloalkenyl", unless otherwise specified, refers to cyclic ring-containing radicals containing in the range of about 3 up to 8 carbon atoms with at least one carbon-carbon double bond such as cyclopropenyl, cyclobutenyl, and cyclopentenyl. The term "cycloalkenylalkyl" refers to a cycloalkenyl group directly attached to an alkyl group which are then attached to the main structure at any carbon from the alkyl group that results in the creation of a stable structure.

The term "aryl", unless otherwise specified, refers to aromatic radicals having in the range of 6 up to 20 carbon atoms such as phenyl, naphthyl, tetrahydronaphthyl, indanyl, and biphenyl.

The term "arylalkyl", unless otherwise specified, refers to an aryl group as defined above directly bonded to an alkyl group as defined above, e.g., —$CH_2C_6H_5$ and —$C_2H_5C_6H_5$.

The term "heterocyclic ring", unless otherwise specified, refers to a non-aromatic 3 to 15 member ring radical which consists of carbon atoms and at least one heteroatom selected from nitrogen, phosphorus, oxygen and sulfur. For purposes of this invention, the heterocyclic ring radical may be a mono-, bi-, tri- or tetracyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized. The heterocyclic ring radical may be attached to the main structure at any heteroatom or carbon atom that results in the creation of a stable structure.

The term "heterocyclyl", unless otherwise specified, refers to a heterocylic ring radical as defined above. The heterocylcyl ring radical may be attached to the main structure at any heteroatom or carbon atom that results in the creation of a stable structure.

The term "heterocyclylalkyl", unless otherwise specified, refers to a heterocylic ring radical as defined above directly bonded to an alkyl group. The heterocyclylalkyl radical may be attached to the main structure at carbon atom in the alkyl group that results in the creation of a stable structure. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

The term "heteroaryl", unless otherwise specified, refers to an optionally substituted 5 to 14 member aromatic ring having one or more heteroatoms selected from N, O, and S as ring atoms. The heteroaryl may be a mono-, bi- or tricyclic ring system. Examples of such "heterocyclic ring" or "heteroaryl" radicals include, but are not limited to, oxazolyl, thiazolyl, imidazolyl, pyrrolyl, furanyl, pyridinyl, pyrimidinyl, pyrazinyl, benzofuranyl, indolyl, benzothiazolyl, benzoxazolyl, carbazolyl, quinolyl, isoquinolyl, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, 4-piperidonyl, pyrrolidinyl, pyridazinyl, oxazolinyl, oxazolidinyl, triazolyl, indanyl, isoxazolyl, isoxazolidinyl, morpholinyl, thiazolinyl, thiazolidinyl, isothiazolyl, quinuclidinyl, isothiazolidinyl, isoindolyl, indolinyl, isoindolinyl, octahydroindolyl, octahydroisoindolyl, decahydroisoquinolyl, benzimidazolyl, thiadiazolyl, benzopyranyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, and isochromanyl. The heteroaryl ring radical may be attached to the main structure at any heteroatom or carbon atom that results in the creation of a stable structure. The term "substituted heteroaryl" also includes ring systems substituted with one or more oxide (—O—) substituents, such as pyridinyl N-oxides.

The term "heteroarylalkyl", unless otherwise specified, refers to a heteroaryl ring radical as defined above directly bonded to an alkyl group. The heteroarylalkyl radical may be attached to the main structure at any carbon atom from alkyl group that results in the creation of a stable structure.

The term "cyclic ring" refers to a cyclic ring containing 3 to 10 carbon atoms.

The term "substituted" unless otherwise specified, refers to substitution with any one or any combination of the following substituents which may be the same or different and are independently selected from hydrogen, hydroxy, halogen, carboxyl, cyano, nitro, oxo (=O), thio(=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted heteroaryl, substituted or unsubstituted heteroarylalkyl, substituted or unsubstituted heterocyclic ring, substituted heterocyclylalkyl ring, substituted or unsubstituted guanidine, —COOR$^x$, —C(O)R$^x$, —C(S)R$^x$, —C(O)NR$^x$R$^y$, —C(O)ONR$^x$R$^y$, —NR$^y$R$^z$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$—OR$^x$C(O)NR$^x$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, and —ONO$_2$, wherein R$^x$, R$^y$ and R$^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted amino, substituted or unsubstituted heteroaryl, substituted or unsubstituted heteroarylalkyl, substituted or unsubstituted heterocyclic ring, or substituted heterocyclylalkyl ring, or any two of $R^x$, $R^y$ and $R^z$ may be joined to form a substituted or unsubstituted saturated or unsaturated 3-10 membered ring, which may optionally include heteroatoms which may be the same or different and are selected from O, $NR^x$ (e.g., $R^x$ can be hydrogen or $C_{1-6}$ alkyl) or S. Substitution or the combinations of substituents envisioned by this invention are preferably those that result in the formation of a stable or chemically feasible compound. The term stable as used herein refers to the compounds or the structure that are not substantially altered when subjected to conditions to allow for their production, detection and preferably their recovery, purification and incorporation into a pharmaceutical composition. The substituents in the aforementioned "substituted" groups cannot be further substituted. For example, when the substituent on "substituted alkyl" is "substituted aryl", the substituent on "substituted aryl" cannot be "substituted alkenyl".

The term "halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

The term "protecting group" or "PG" refers to a substituent that is employed to block or protect a particular functionality. Other functional groups on the compound may remain reactive. For example, an "amino-protecting group" is a substituent attached to an amino group that blocks or protects the amino functionality in the compound. Suitable amino-protecting groups include, but are not limited to, acetyl, trifluoroacetyl, tert-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include, but are not limited to, acetyl and silyl. A "carboxy-protecting group" refers to a substituent of the carboxy group that blocks or protects the carboxy functionality. Suitable carboxy-protecting groups include, but are not limited to, —$CH_2CH_2SO_2Ph$, cyanoethyl, 2-(trimethylsilyl) ethyl, 2-(trimethylsilyl)ethoxymethyl, -2-(p-toluenesulfonyl)ethyl, 2-(p-nitrophenylsulfenyl)ethyl, 2-(diphenylphosphino)-ethyl, and nitroethyl. For a general description of protecting groups and their use, see T. W. Greene, Protective Groups in Organic Synthesis, John Wiley & Sons, New York, 1991.

Certain of the compounds described herein may contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. For the instance the non-limiting example of intermediate mixtures include a mixture of isomers in a ratio of 10:90, 13:87, 17:83, 20:80, or 22:78.

Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

The term "tautomers" refers to compounds, which are characterized by relatively easy interconversion of isomeric forms in equilibrium. These isomers are intended to be covered by this invention. "Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under the reaction conditions, cleave from the starting material, thus promoting reaction at a specified site. Suitable examples of such groups, unless otherwise specified, include halogen atoms and mesyloxy, p-nitrobenzensulphonyloxy and tosyloxy groups.

The term "prodrug" refers to a compound, which is an inactive precursor of a compound that is converted into its active form in the body by normal metabolic processes. Prodrug design is discussed generally in Hardma, et al. (Eds.), Goodman and Gilman's The Pharmacological Basis of Therapeutics, 9th ed., pp. 11-16 (1996). A thorough discussion is provided in Higuchi, et al., Prodrugs as Novel Delivery Systems, Vol. 14, ASCD Symposium Series, and in Roche (ed.), Bioreversible Carriers in Drug Design, American Pharmaceutical Association and Pergamon Press (1987). To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into the circulation, thereby effectively increasing the biological half-life of the originally administered compound.

The term "ester" refers to a compound, which is formed by reaction between an acid and an alcohol with elimination of water. An ester can be represented by the general formula RCOOR' (where R is a drug and R' is a chemical group).

These prodrugs and esters' are intended to be covered within the scope of this invention.

Additionally the instant invention also includes the compounds which differ only in the presence of one or more isotopically enriched atoms for example replacement of hydrogen with deuterium or tritium, or the replacement of a carbon by $^{13}$C- or $^{14}$C-enriched carbon.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

Pharmaceutically acceptable salts forming part of this invention include salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, ornithine, lysine, arginine, and serine; quaternary ammonium salts of the compounds of invention with alkyl halides, alkyl sulphates such as McI and (Me)$_2$SO$_4$; non-natural amino acids such as D-isomers or substituted amino acids; guanidine; and substituted guanidine wherein the substituents are selected from nitro, amino, alkyl, alkenyl, alkynyl, ammonium or substituted ammonium salts and aluminum salts. Salts may include acid addition salts where appropriate which may be sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, and ketoglutarates.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The following abbreviations and terms have the indicated meanings throughout: PI3-K=Phosphoinositide 3-kinase; PI=phosphatidylinositol; AIDS=Acquired Immuno Deficiency Syndrome; HIV=Human Immunodeficiency Virus; MeI=Methyl Iodide; ND: Not determined.

Abbreviations used herein have their conventional meaning within the chemical and biological arts.

The term "cell proliferation" refers to a phenomenon by which the cell number has changed as a result of division. This term also encompasses cell growth by which the cell morphology has changed (e.g., increased in size) consistent with a proliferative signal.

The terms "co-administration," "administered in combination with," and their grammatical equivalents, as used herein, encompass administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment," "treating," or "ameliorating" are used interchangeably. These terms refers to an approach for obtaining beneficial or desired results including but, not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "subject" or "patient" refers to an animal (e.g., a dog, cat, horse, or pig), such as a mammal, for example a human. The methods described herein can be useful in both human therapeutics and veterinary applications. In some embodiments, the patient is a mammal, and in some embodiments, the patient is human.

"Radiation therapy" means exposing a patient, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP), or high-energy radiation, including, without limitation, x-rays, gamma rays, and neutrons.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

The term "selective inhibition" or "selectively inhibit" as applied to a biologically active agent refers to the agent's ability to selectively reduce the target signaling activity as compared to off-target signaling activity, via direct or indirect interaction with the target.

The term "pharmaceutically acceptable carrier" or "pharmaceutically acceptable excipient" includes, but is not limited to, any and all solvents, dispersion media, coatings, antibacterial and antifungal agents, isotonic and absorption delaying agents, one or more suitable diluents, fillers, salts, disintegrants, binders, lubricants, glidants, wetting agents, controlled release matrices, colorants/flavoring, carriers, excipients, buffers, stabilizers, solubilizers, and combinations thereof. Except insofar as any conventional media or agent is incompatible with the active ingredient, its use in the therapeutic compositions of the invention is contemplated. Supplementary active ingredients can also be incorporated into the compositions.

In certain embodiments, one or more of the compounds described herein bind specifically to a PI3 kinase or a protein kinase selected from the group consisting of mTor, DNA-dependent protein kinase (Pubmed protein accession number (PPAN) AAA79184), AbI tyrosine kinase (CAA52387), Bcr-Abl, hemopoietic cell kinase (PPAN CAI19695), Src (PPAN CAA24495), vascular endothelial growth factor receptor 2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fms-related tyrosine kinase 3 (PPAN NP_004110), platelet-derived growth factor receptor alpha (PPAN NP_990080), RET (PPAN CAA73131), and any other related protein kinases, as well as any functional mutants thereof.

In other embodiments, the $IC_{50}$ of a compound described herein for pi 10α, pi 10β, pi 10γ, or pi 10δ is less than about 1 μM, less than about 100 nM, less than about 50 nM, less than about 10 nM, less than 1 nM or less than about 0.5 nM. In some embodiments, the $IC_{50}$ of a compound described herein for mTor is less than about 1 μM, less than about 100 nM, less than about 50 nM, less than about 10 nM, less than 1 nM or less than about 0.5 nM. In some other embodiments, one or more of the compounds described herein exhibit dual binding specificity and are capable of inhibiting a PI3 kinase (e.g., a class I PI3 kinase) as well as a protein kinase (e.g., mTor) with an $IC_{50}$ value less than about 1 μM, less than about 100 nM, less than about 50 nM, less than about 10 nM, less than 1 nM or less than about 0.5 nM.

In additional embodiments, the compounds of the present invention exhibit one or more functional characteristics disclosed herein. For example, one or more of the compounds described herein bind specifically to a PI3 kinase. In some embodiments, the $IC_{50}$ of a compound described herein for pi 10α, pi 10β, pi 10γ, or pi 10δ is less than about 1 μM, less than about 100 nM, less than about 50 nM, less than about 10 nM, less than about 1 nM, less than about 0.5 nM, less than about 100 pM, or less than about 50 pM.

In other embodiments, the compounds of the present invention selectively inhibit one or more members of type I or class I phosphatidylinositol 3-kinases (PI3-kinase) with an $IC_{50}$ value of about 100 nM or less, about 50 nM or less, about 10 nM or less, about 5 nM or less, about 100 pM or less, about 10 pM or less, or about 1 pM or less as measured in an in vitro kinase assay.

In yet another aspect, an inhibitor that selectively inhibits one or more members of type I PI3-kinases, or an inhibitor that selectively inhibits one or more type I PI3-kinase mediated signaling pathways, alternatively can be understood to refer to a compound that exhibits a 50% inhibitory concentration ($IC_{50}$) with respect to a given type I PI3-kinase, that is at least 10-fold lower, at least 20-fold lower, at least 50-fold lower, at least 100-fold lower, at least 1000-fold lower than the inhibitor's $IC_{50}$ with respect to the rest of the other type I PI3-kinases.

As used herein, the term "dual PI3-kinase δ/γ inhibitor" and "dual PI3-kinase δ/γ selective inhibitor" refers to a compound that inhibits the activity of both the PI3-kinase δ and γ isozyme more effectively than other isozymes of the PI3K family. A dual PI3-kinase δ/γ inhibitor is therefore more selective for PI3-kinase δ and γ than conventional PI3K inhibitors such as CAL-130, wortmannin and LY294002, which are nonselective PI3K inhibitors.

Inhibition of PI3-kinase δ and γ may be of therapeutic benefit in treatment of various conditions, e.g., conditions characterized by an inflammatory response including, but not limited to, autoimmune diseases, allergic diseases, and arthritic diseases. Importantly, inhibition of PI3-kinase δ and γ function does not appear to affect biological functions such as viability and fertility.

"Inflammatory response" as used herein is characterized by redness, heat, swelling and pain (i.e., inflammation) and typically involves tissue injury or destruction. An inflammatory response is usually a localized, protective response elicited by injury or destruction of tissues, which serves to destroy, dilute or wall off (sequester) both the injurious agent and the injured tissue. Inflammatory responses are notably associated with the influx of leukocytes and/or leukocyte (e.g., neutrophil) chemotaxis. Inflammatory responses may result from infection with pathogenic organisms and viruses, noninfectious means such as trauma or reperfusion following myocardial infarction or stroke, immune responses to foreign antigens, and autoimmune diseases. Inflammatory responses amenable to treatment with the methods and compounds according to the invention encompass conditions associated with reactions of the specific defense system as well as conditions associated with reactions of the non-specific defense system.

The therapeutic methods of the invention include methods for the amelioration of conditions associated with inflammatory cell activation. "Inflammatory cell activation" refers to the induction by a stimulus (including but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including but not limited to, major histocompatibility antigens or cell adhesion molecules) in inflammatory cells (including but not limited to monocytes, macrophages, T lymphocytes, B lymphocytes, granulocytes (polymorphonuclear leukocytes including neutrophils, basophils, and eosinophils) mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory condition.

"Autoimmune disease" as used herein refers to any group of disorders in which tissue injury is associated with humoral or cell-mediated responses to the body's own constituents.

"Transplant rejection" as used herein refers-to any immune response directed against grafted tissue (including organs or cells (e.g., bone marrow), characterized by a loss of function of the grafted and surrounding tissues, pain, swelling, leukocytosis, and thrombocytopenia).

"Allergic disease" as used herein refers to any symptoms, tissue damage, or loss of tissue function resulting from allergy.

"Arthritic disease" as used herein refers to any disease that is characterized by inflammatory lesions of the joints attributable to a variety of etiologies.

"Dermatitis" as used herein refers to any of a large family of diseases of the skin that are characterized by inflammation of the skin attributable to a variety of etiologies.

As previously described, the term "dual PI3-kinase δ/γ selective inhibitor" generally refers to a compound that inhibits the activity of the PI3-kinase δ and γ isozyme more effectively than other isozymes of the PI3K family. The relative efficacies of compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". $IC_{50}$ determinations can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Accordingly, a dual PI3-kinase δ/γ selective inhibitor alternatively can be understood to refer to a compound that exhibits a 50% inhibitory concentration ($IC_{50}$) with respect to PI3-kinase δ and γ, that is at least 10-fold lower, at least 20-fold lower, or at least 30-fold lower than the $IC_{50}$ value with respect to any or all of the other class I PI3K family members. In an alternative embodiment of the invention, the term dual PI3-kinase δ/γ selective inhibitor can be understood to refer to a compound that exhibits an $IC_{50}$ with respect to PI3-kinase δ and γ that is at least 30-fold lower, at least 50-fold lower, at least 100-fold lower, at least 200-fold lower, or at least 500-fold lower than the $IC_{50}$ with respect to any or all of the other PI3K class I family members. A dual PI3-kinase δ/γ selective inhibitor is typically administered in an amount such that it selectively inhibits both PI3-kinase δ and γ activity, as described above.

In certain embodiments, the compounds of the present invention exhibit PI3-kinase δ and γ inhibition almost equally (~1:1) or at a maximum ratio of 1:5, i.e., the compound the of the present invention exhibit almost equal $IC_{50}$ values for both PI3-kinase δ and γ enzyme, or at most a 3 to 8 fold difference between the two.

The methods of the invention may be applied to cell populations in vivo or ex vivo. "In vivo" means within a living individual, as within an animal or human or in a subject's body. In this context, the methods of the invention may be used therapeutically or prophylactically in an individual. "Ex vivo" or "in vitro" means outside of a living individual. Examples of ex vivo cell populations include in vitro cell cultures and biological samples including but not limited to fluid or tissue samples obtained from individuals. Such samples may be obtained by methods known in the art. Exemplary biological fluid samples include blood, cerebrospinal fluid, urine, and saliva. Exemplary tissue samples include tumors and biopsies thereof. In this context, the invention may be used for a variety of purposes, including therapeutic and experimental purposes. For example, the invention may be used ex vivo or in vitro to determine the optimal schedule and/or dosing of administration of a PI3-kinase δ selective inhibitor for a given indication, cell type, individual, and other parameters. Information gleaned from such use may be used for experimental or diagnostic purposes or in the clinic to set protocols for in vivo treatment. Other ex vivo uses for which the invention may be suited are described below or will become apparent to those skilled in the art.

Pharmaceutical Compositions

The invention provides a pharmaceutical composition comprising one or more compounds of the present invention and one or more pharmaceutically acceptable carriers or excipients. In one embodiment, the pharmaceutical composition includes a therapeutically effective amount of a compound of the present invention. The pharmaceutical composition may include one or more additional active ingredients as described herein.

The pharmaceutical carriers and/or excipients may be selected from diluents, fillers, salts, disintegrants, binders, lubricants, glidants, wetting agents, controlled release matrices, colorants, flavorings, buffers, stabilizers, solubilizers, and combinations thereof.

In one embodiment, the pharmaceutical compositions described herein contain from about 0.1 mg to about 1,000 mg, such as from about 1 mg to about 1,000 mg or from about 20 mg to about 800 mg or 50 mg to about 600 mg or 50 mg to about 600 mg of one or more compounds of the present invention. 100 mg to about 400 mg of one or more compounds of the present invention.

The pharmaceutical compositions of the present invention can be administered alone or in combination with one or more other active agents. Where desired, the subject compounds and other agent(s) may be mixed into a preparation or both components may be formulated into separate preparations to use them in combination separately or at the same time.

The compounds and pharmaceutical compositions of the present invention can be administered by any route that enables delivery of the compounds to the site of action, such as orally, intranasally, topically (e.g., transdermally), intraduodenally, parenterally (including intravenously, intraarterially, intramuscularally, intravascularally, intraperitoneally or by injection or infusion), intradermally, by intramammary, intrathecally, intraocularly, retrobulbarly, intrapulmonary (e.g., aerosolized drugs) or subcutaneously (including depot administration for long term release e.g., embedded-under the-splenic capsule, brain, or in the cornea), sublingually, anally, rectally, vaginally, or by surgical implantation (e.g., embedded under the splenic capsule, brain, or in the cornea).

The compositions can be administered in solid, semi-solid, liquid or gaseous form, or may be in dried powder, such as lyophilized form. The pharmaceutical compositions can be packaged in forms convenient for delivery, including, for example, solid dosage forms such as capsules, sachets, cachets, gelatins, papers, tablets, suppositories, pellets, pills, troches, and lozenges. The type of packaging will generally depend on the desired route of administration. Implantable sustained release formulations are also contemplated, as are transdermal formulations.

Method of Treatment

The amount of the compound to be administered is dependent on the subject (e.g., mammal) being treated, the severity of the disorder or condition, the rate of administration, the disposition of the compound and the discretion of the prescribing physician. However, an effective dosage is in the range of about 0.001 to about 100 mg/kg body weight per day, preferably about 1 to about 35 mg/kg/day, in single or divided doses. For a 70 kg human, this would amount to about 0.05 to 7 g/day, preferably about 0.05 to about 2.5 g/day An effective amount of a compound of the invention may be administered in either single or multiple doses (e.g., twice or three times a day).

The present invention also provides methods of using the compounds or pharmaceutical compositions of the present invention to treat disease conditions, including but not limited to diseases associated with malfunctioning of one or more types of PI3 kinase. A detailed description of conditions and disorders mediated by PI3K δ and/or γ kinase activity is set forth in, e.g., WO 2001/81346, US 2005/043239, WO 2011/055215 and WO 2012/151525, each of which is incorporated herein by reference in its entirety.

The treatment methods provided herein comprise administering to the subject a therapeutically effective amount of a compound of the invention. In one embodiment, the present invention provides a method of treating an inflammation disorder, including autoimmune diseases in a mammal. The method comprises administering to said mammal a therapeutically effective amount of a compound of the present invention, or a pharmaceutically acceptable salt, ester, prodrug, solvate, hydrate or derivative thereof.

It will be appreciated that the treatment methods of the invention are useful in the fields of human medicine and veterinary medicine. Thus, the individual to be treated may be a mammal, preferably human, or other animals. For veterinary purposes, individuals include but are not limited to farm animals including cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

In some embodiments, the method of treating inflammatory or autoimmune diseases comprises administering to a subject (e.g. a mammal) a therapeutically effective amount of one or more compounds of the present invention that selectively inhibit PI3K-δ and/or PI3K-γ as compared to all other type I PI3 kinases. Such selective inhibition of PI3K-δ and/or PI3K-γ may be advantageous for treating any of the diseases or conditions described herein. For example, selective inhibition of PI3K-δ may inhibit inflammatory responses associated with inflammatory diseases, autoimmune disease, or diseases related to an undesirable immune response including but not limited to asthma, emphysema, allergy, dermatitis, rheumatoid arthritis, psoriasis, lupus erythematosus, or graft versus host disease. Selective inhibition of PI3K-δ may further provide for a reduction in the inflammatory or undesirable immune response without a concomittant reduction in the ability to reduce a bacterial, viral, and/or fungal infection. Selective inhibition of both PI3K-δ and PI3K-γ may be advantageous for inhibiting the inflammatory response in the subject to a greater degree than that would be provided for by inhibitors that selectively inhibit PI3K-δ or PI3K-γ alone. In one aspect, one or more of the subject methods are effective in reducing antigen specific antibody production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more. In another aspect, one or more of the subject methods are effective in reducing antigen specific IgG3 and/or IgGM production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more.

In other embodiments, the present invention provides methods of using the compounds or pharmaceutical compositions to treat respiratory diseases including but not limited to diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In another embodiment, the compounds described herein are used for the treatment of asthma. Also, the compounds or pharmaceutical compositions described herein may be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma) or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

The invention also relates to a method of treating diseases related to vasculogenesis or angiogenesis in a mammal that comprises administering to said mammal a therapeutically effective amount of a compound of the present invention, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with compounds of the present invention, or pharmaceutically acceptable salt, ester, prodrug, solvate, hydrate or derivative of said compounds, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarcinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-I) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

In another aspect, the present invention provides methods of disrupting the function of a leukocyte or disrupting a function of an osteoclast. The method includes contacting the leukocyte or the osteoclast with a function disrupting amount of a compound of the invention.

In another aspect of the present invention, methods are provided for treating ophthalmic disease by administering one or more of the subject compounds or pharmaceutical compositions to the eye of a subject.

In some embodiments, the kinase is a lipid kinase or a protein kinase. In some embodiments, the kinase is selected from the group consisting of PI3 kinase including different isorforms such as PI3 kinase α, PI3 kinase β, PI3 kinase γ, PI3 kinase δ; DNA-PK; mTor; AbI, VEGFR, Ephrin receptor B4 (EphB4); TEK receptor tyrosine kinase (HE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Inulsin Receptor (IR) and IGFR.

The invention further provides methods of modulating PI3 kinase activity by contacting a PI3 kinase with an amount of a compound of the invention sufficient to modulate the activity of the PI3 kinase. Modulate can be inhibiting or activating PI3 kinase activity. In some embodiments, the invention provides methods of inhibiting PI3 kinase activity by contacting a PI3 kinase with an amount of a compound of the invention sufficient to inhibit the activity of the PI3 kinase. In some embodiments, the invention provides methods of inhibiting PI3 kinase activity. Such inhibition can take place in solution, in a cell expressing one or more PI3 kinases, in a tissue comprising a cell expressing one or more PI3 kinases, or in an organism expressing one or more PI3 kinases. In some embodiments, the invention provides methods of inhibiting PI3 kinase activity in an animal (including mammal such as humans) by contacting said animal with an amount of a compound of the invention sufficient to inhibit the activity of the PI3 kinase in said animal.

The following general methodology described herein provides the manner and process of making and using the compound of the present invention and are illustrative rather than limiting. Further modification of provided methodology and additionally new methods may also be devised in order to achieve and serve the purpose of the invention. Accordingly, it should be understood that there may be other embodiments which fall within the spirit and scope of the invention as defined by the specification hereto.

Illustrative compounds of the present invention include those specified above in Tables 1 and 2, and pharmaceutically acceptable salts thereof. The present invention should not be construed to be limited to them.

General Methods of Preparation of Compounds of the Invention

The compounds of the present invention may be prepared by using the methods (with or without modifications) as disclosed in International Patent Publication Nos. WO 2008/127226, WO 2009/088986, WO 2011/055215 and WO 2012/151525, each of which is hereby incorporated by reference.

Unless otherwise indicated, the variables (e.g., R, $R^1$, X, $R^a$, $R^b$, $R^c$, n and Cy) when used in the below formulae are to be understood to present those groups described above in relation to the formulas above, such as formula (I). These methods can similarly be applied to other compounds of formula as provided herein above with or without modification.

Scheme 1

This scheme provides a method for the preparation of a compound of formula (I) wherein X is N, R is H, alkyl or halogen, Pg is protecting group and all the other variables such as R, $R^1$, $R^2$, $R^3$, $R^a$, $R^b$, $R^c$, X and n are the same as described above in relation to formula (I)

Scheme-1

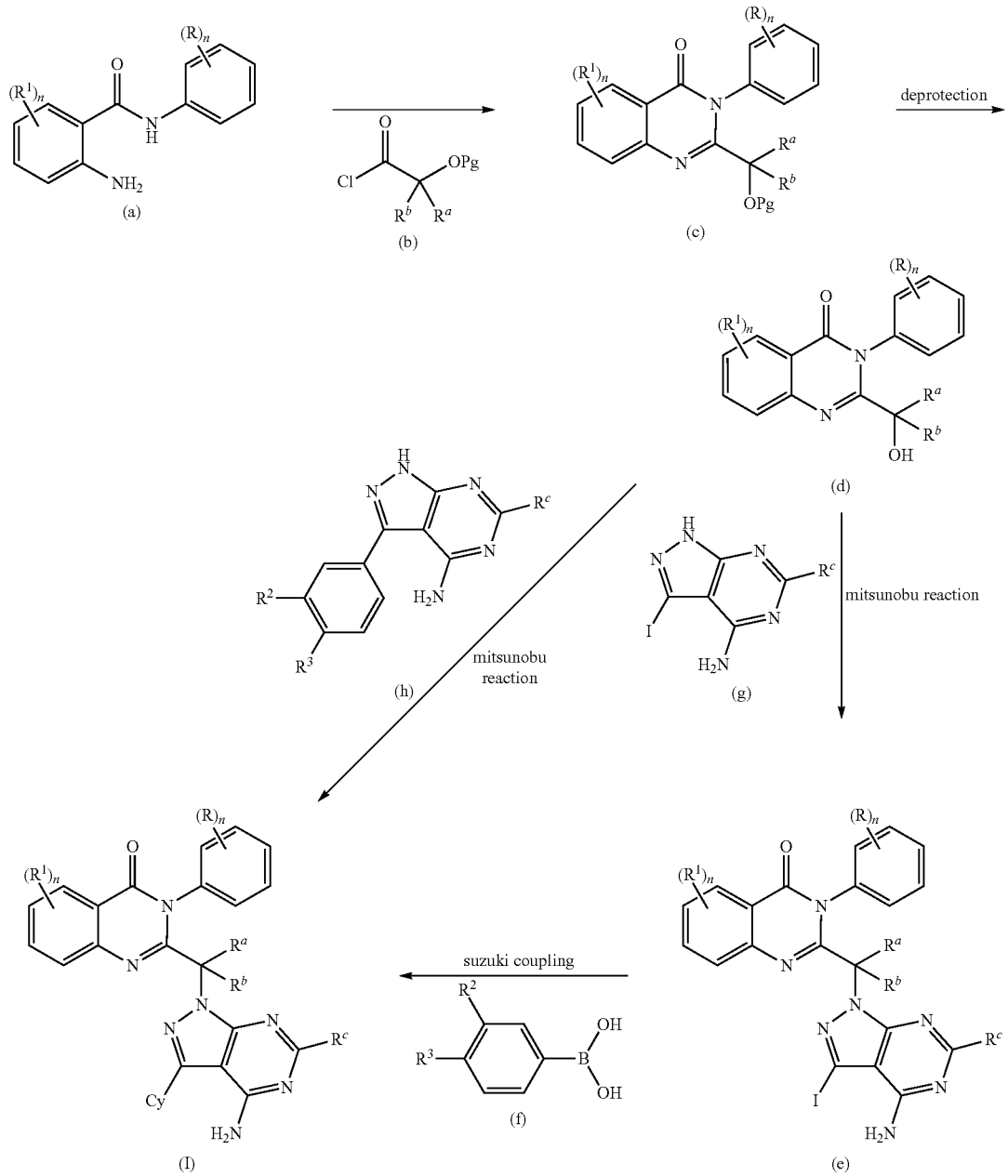

The compound of the formula (a) can be reacted with the compound of formula (b) to form a compound of formula (c), wherein Pg is a suitable protecting group. The compound of formula (c) can be de-protected to yield the compound of formula (d). The compound of formula (d) can be coupled with a compound of formula (g) under Mitsunobu reaction conditions to form a compound of formula (e), for example, in the presence of a dialkyl azodicarboxylate and a triaryl phosphine. The compound of formula (e) can be coupled with a compound of formula (f) under Suzuki reaction conditions, for example, in the presence of a suitable base and a Palladium catalyst such as Pd(dppf)$_2$Cl$_2$.CH$_2$Cl$_2$, to afford the desired compound of formula (I).

Alternatively, the compound of formula (d) can be coupled with a compound of formula (h) to form the desired compound of formula (I) under Mitsunobu reaction conditions, for example, in the presence of a dialkyl azodicarboxylate and a triaryl phosphine.

Scheme 2

This scheme provides a method for the preparation of a compound of formula (I) wherein X is CH, R is H, alkyl or halogen, and all the other variables such as $R^1$, $R^2$, $R^3$, $R^a$, $R^b$, $R^c$ and n are the same as described above in relation to formula (I).

The compound of formula (a1) can be coupled with a compound of formula (g) to form a compound of formula (c1) under Mitsunobu reaction conditions, for example, in the presence of a dialkyl azodicarboxylate and a triaryl phosphine. The compound of formula (c1) can be coupled with a compound of formula (f) to form the desired compound of formula (I) under Suzuki reaction conditions, for example, in the presence of a suitable base and a Palladium catalyst such as Pd(dppf)$_2$Cl$_2$.CH$_2$Cl$_2$.
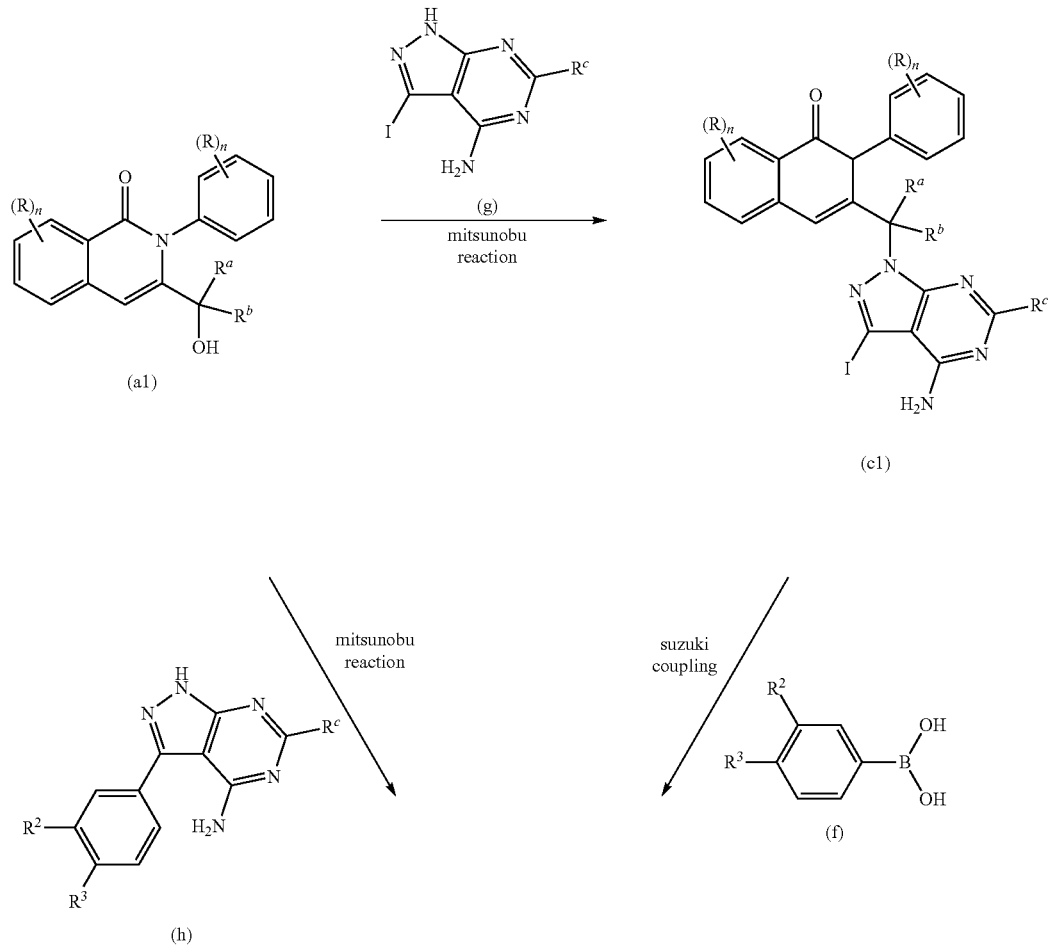
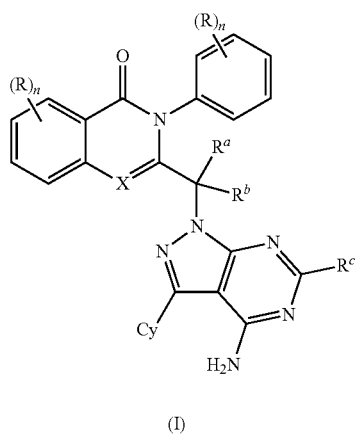

Alternatively, the compound of formula (a1) can be coupled with a compound of formula (h) to form the desired compound of formula (I) under Mitsunobu reaction conditions, for example, in the presence of a dialkyl azodicarboxylate and a triaryl phosphine.

Scheme 3

This scheme provides a method for the preparation of a compound of formula (I) wherein X is N, R is H, alkyl or halogen, G is OH or Cl, Lg is Leaving Group and all the other variables such as $R^1$, $R^2$, $R^3$, $R^a$, $R^b$, $R^c$ and n are the same as described above in relation to formula (I)

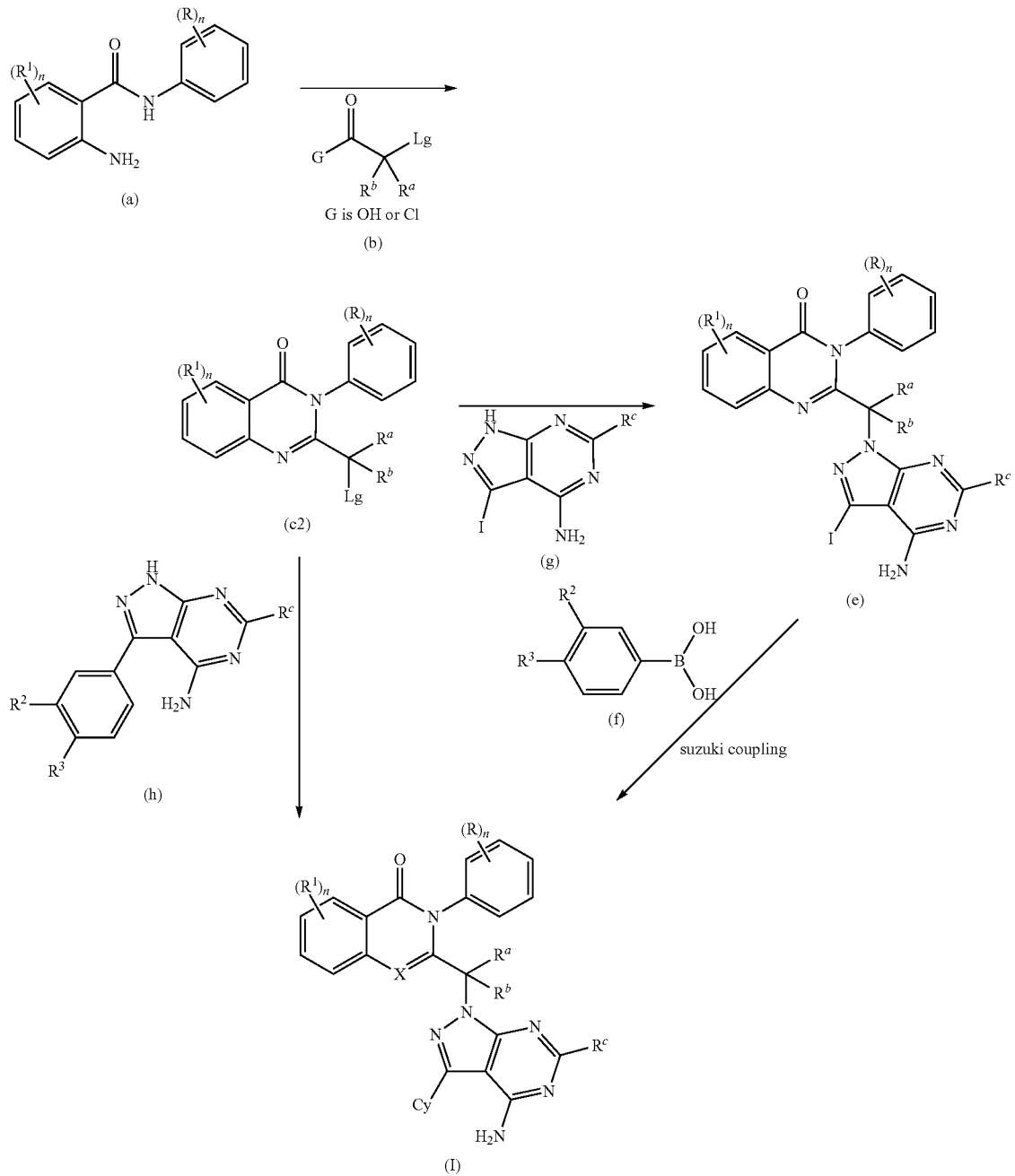

Scheme-3

The compound of the formula (a) can be reacted with the compound of formula (b1) to form a compound of formula (c2), wherein Lg is Leaving group, such as a halogen group. The compound of formula (c2) can be alkylated with a compound of formula (g) in the presence of a suitable base to form the compound of formula (e) which can be coupled with compound of formula (f) under Suzuki reaction conditions, for example, in the presence of a suitable base and a Palladium catalyst such as $Pd(dppf)_2Cl_2 \cdot CH_2Cl_2$, to afford the desired compound of formula (I)

Alternatively, the compound of formula (c2) can be alkylated with a compound of formula (h) in the presence of a suitable base to form the desired compound of formula (I).

Scheme 4

This scheme provides a method for the preparation of a compound of formula (I) wherein X is CH, R is H, alkyl or halogen, and all the other variables such as $R^1$, $R^2$, $R^3$, $R^a$, $R^b$, $R^c$ and n are same as described above in relation to formula (I).

Similar methodologies with certain modifications as known to those skilled in the art can be used to synthesize compounds of the formula (I), (I-A), (I-A1), (I-A2), (I-A3), (I-A4), (I-A5), (I-B), (I-B1), (I-B2), (I-B3), (I-B4), (I-B5), (II), (II-1), (II-2), (II-3), (II-4), (II-5), (III), (III-A) and (III-B), wherein all the variables are to be understood to present those groups described above in relation to these formulas using suitable intermediates and reagents.

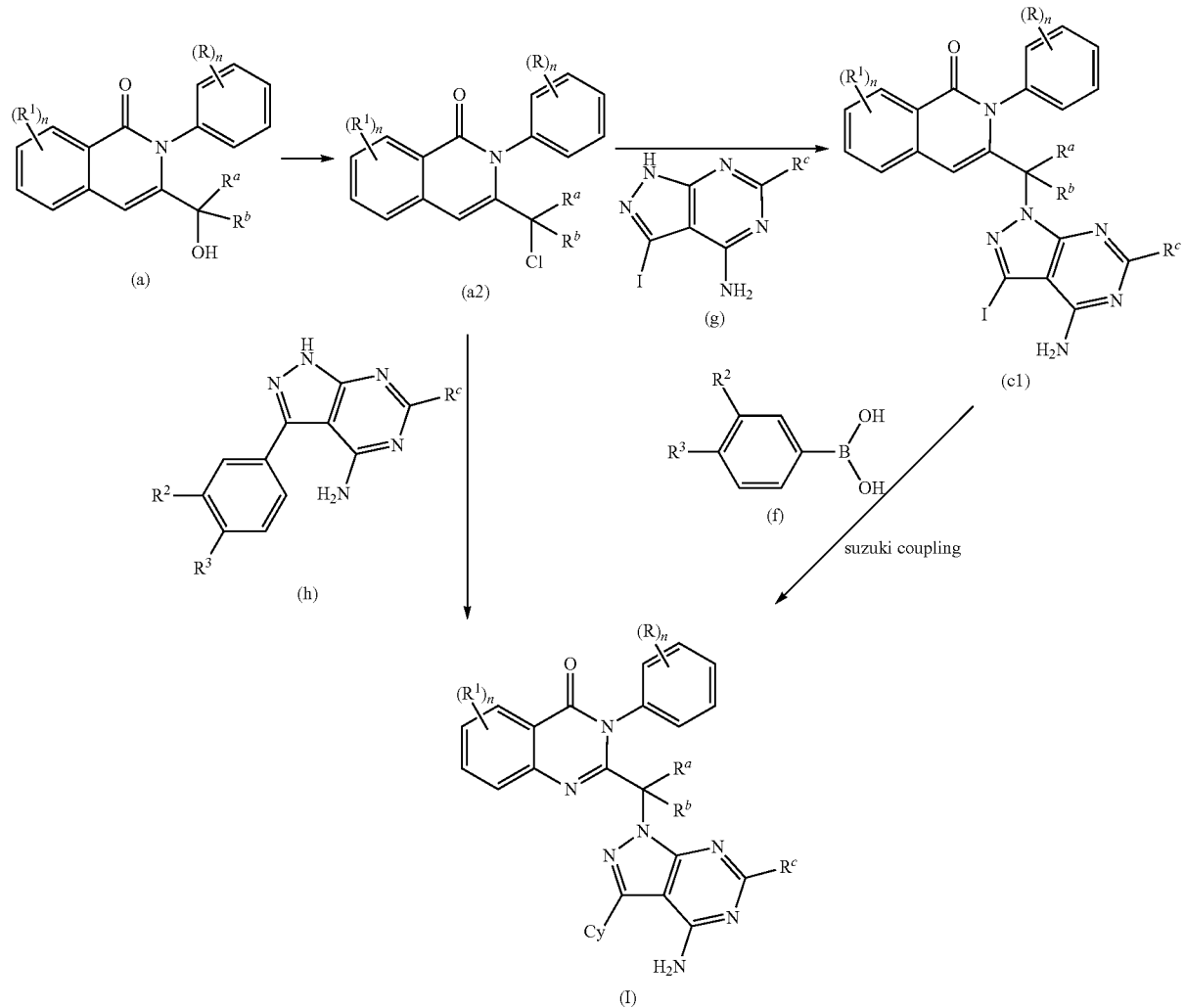

The compound of the formula (a1) can be transformed to a compound of the formula (a2). The compound of formula (a2) can be alkylated with a compound of formula (g) in the presence of a suitable base to form the compound of formula (c1) which can be coupled with a compound of formula (f) under Suzuki reaction conditions, for example, in the presence of a suitable base and a Palladium catalyst such as $Pd(dppf)_2Cl_2 \cdot CH_2Cl_2$, to afford the desired compound of formula (I).

Alternatively, the compound of formula (a2) can be alkylated with a compound of formula (h) in the presence of a suitable base to form the desired compound of formula (I).

EXPERIMENTAL

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

As used herein the Superscript 1 refers to International Patent Application No. PCT/IB2010/002804 (WO 2011/055215) and Superscript 2 refers to International Patent Application No. PCT/US2012/036594 (WO 2012/151525).

Intermediates

TABLE 3

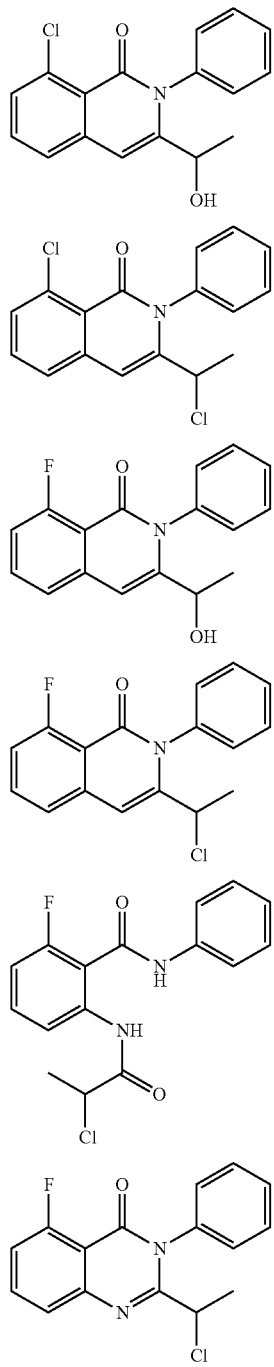

Intermediate 1

Intermediate 2

Intermediate 3

Intermediate 4

Intermediate 5

Intermediate 6

TABLE 3-continued

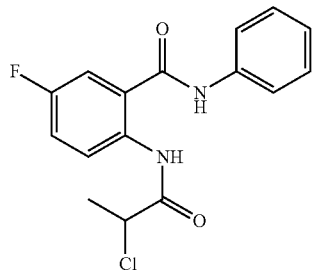 [SMILES: CC(Cl)C(=O)Nc1ccc(F)cc1C(=O)Nc1ccccc1]

Intermediate 7

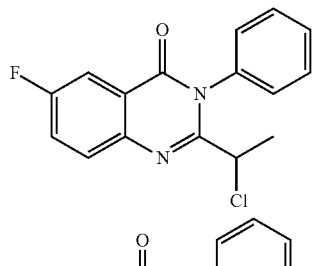

Intermediate 8

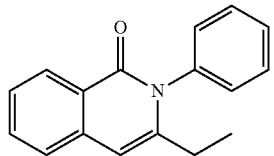

Intermediate 9

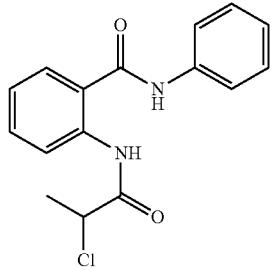 [SMILES: CC(Cl)C(=O)Nc1ccccc1C(=O)Nc1ccccc1]

Intermediate 10

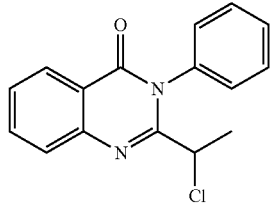 [SMILES: CC(Cl)c1nc2ccccc2c(=O)n1-c1ccccc1]

Intermediate 11

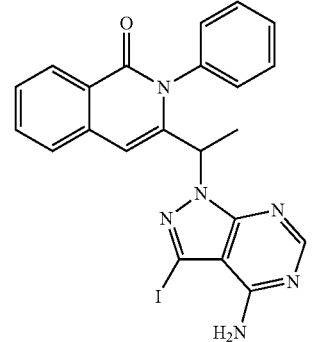 [SMILES: CC(c1cc2ccccc2c(=O)n1-c1ccccc1)n1nc(I)c2c(N)ncnc21]

Intermediate 12

TABLE 3-continued

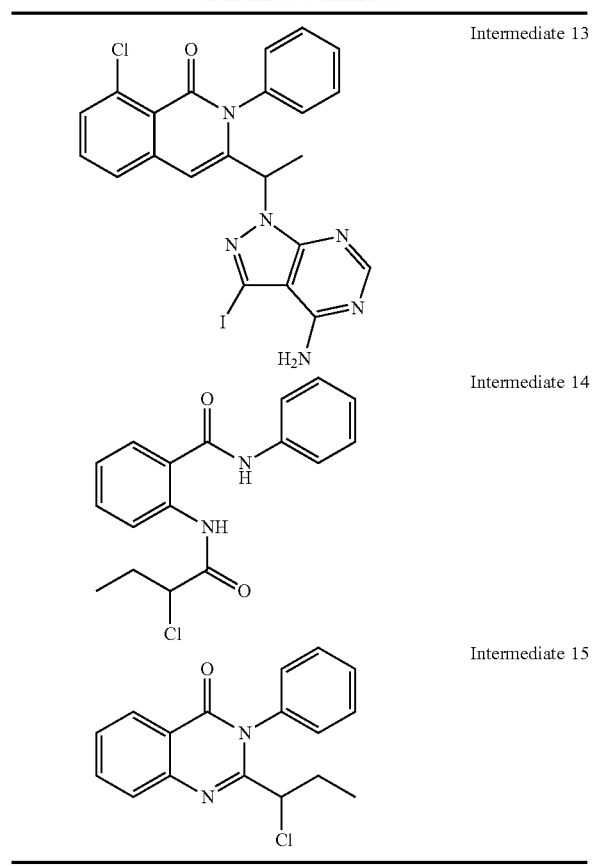

Intermediate 13

Intermediate 14

Intermediate 15

Intermediate 1

8-chloro-3-(1-hydroxyethyl)-2-phenylisoquinolin-1(2H)-one

To 3-(1-aminoethyl)-8-chloro-2-phenylisoquinolin-1(2H)-one (7.0 g, 23.46 mmol), Hcl (7.13 ml) was added and cooled to 0° C. To this mixture solution of sodium nitrite (4.85 g, 70.39 mmol) dissolved in water (135 ml) was added and stirred at RT for 30 min. The reaction mixture was heated to 135° C. for 4 h. The reaction mixture was basified with saturated sodium bicarbonate solution, extracted with ethyl acetate, dried over sodium sulphate and concentrated under reduced pressure. The crude product was column chromatographed with ethyl acetate:petroleum ether to afford the desired compound as brown solid (3.70 g, 53%) which was used as such in next step.

Intermediate 2

8-chloro-3-(1-chloroethyl)-2-phenylisoquinolin-1(2H)-one: To a cooled solution of intermediate 1 (0.500 g, 1.67 mmol) in dichloromethane (10 ml) and triethylamine (0.50 ml, 5.01 mmol), methanesulphonyl chloride (0.30 ml, 3.34 mmol) was added stirred at room temperature for 24 h. The reaction mass was quenched with water, extracted with dichloromethane, dried over sodium sulphate and concentrated. The crude product was column chromatographed with ethyl acetate:petroleum ether to afford the desired compound as brown solid (0.200 g, 37%). Mass: 318.0 (M$^+$).

Intermediate 3

8-fluoro-3-(1-hydroxyethyl)-2-phenylisoquinolin-1(2H)-one: The title compound was obtained as yellow solid (0.940 g, 100%) by using a procedure that is similar to the one described for intermediate 1 from 3-(1-aminoethyl)-8-fluoro-2-phenylisoquinolin-1(2H)-one (0.880 g, 3.11 mmol), 6N HCl (12 ml) sodium nitrite (0.335 g, 4.86 mmol) which was used as such in next step.

Intermediate 4

3-(1-chloroethyl)-8-fluoro-2-phenylisoquinolin-1(2H)-one: The title compound was obtained as yellow solid (0.586 g, 58%) by using a procedure that is similar to the one described for intermediate 2 from intermediate 3 (0.940 g, 3.31 mmol), dichloromethane (20 ml) and triethylamine (1.30 ml, 9.95 mmol), methanesulphonyl chloride (0.51 ml, 6.63 mmol) which was used as such in next step.

Intermediate 5

2-(2-chloropropanamido)-6-fluoro-N-phenylbenzamide: To a solution of 2-amino-6-fluoro-N-phenylbenzamide (1.50 g, 6.51 mmol) in dichloromethane (20 ml) and N-diisopropylethylamine (1.00 g, 7.81 mmol) cooled to 0° C., 2-chloropropionyl chloride (0.75 ml, 7.81 mmol) was added drop wise. After 1 h, the reaction mixture was quenched with water, extracted with dichloromethane. The organic layer was washed with saturated sodium bicarbonate solution, brine solution, dried over sodium sulphate and concentrated. The crude product was column chromatographed with ethyl acetate:petroleum ether to afford the desired compound as off-white solid (1.60 g, 77%). $^1$H-NMR (δ ppm, CDCl$_3$, 400 MHz): 11.86 (s, 1H), 8.45 (d, J=8.4 Hz, 1H), 8.37 (d, J=12.8 Hz, 1H), 7.63 (m, 2H), 7.49-7.38 (m, 3H), 7.23 (t, J=7.5 Hz, 1H), 6.97 (dd, J=11.7, 8.4 Hz, 1H), 4.53 (q, J=7.0 Hz, 1H), 1.81 (d, J=7.0 Hz, 3H).

Intermediate 6

2-(1-chloroethyl)-5-fluoro-3-phenylquinazolin-4(3H)-one: To intermediate 5 (1.60 g, 4.98 mmol), POCl$_3$ (13.3 ml) was added and heated to 125° C. for 12 h. The reaction mixture was quenched into crushed ice, neutralised with saturated sodium bicarbonate solution and extracted with ethyl acetate. The organic layer was dried over sodium sulphate and concentrated. The crude product was column chromatographed with ethyl acetate:petroleum ether to afford the desired compound as brown solid (0.85 g, 57%). Mass: 303.0 (M$^+$).

Intermediate 7

2-(2-chloropropanamido)-6-fluoro-N-phenylbenzamide: The title compound was obtained as brown solid (2.60 g, 80%) by using a procedure that is similar to the one described for intermediate 5 from 2-amino-5-fluoro-N-phenylbenzamide (2.50 g, 10.07 mmol), dichloromethane (20 ml), N-diisopropylethylamine (2.10 g, 12.08 mmol) and 2-chloropropionyl chloride (1.17 ml, 12.08 mmol). $^1$H-NMR (δ ppm, CDCl$_3$, 400 MHz): 11.23 (s, 1H), 8.45 (dd, J=9.2, 5.1 Hz, 1H), 7.96 (s, 1H), 7.66 (m, 2H), 7.43 (m, 2H), 7.35 (dd, J=12.0, 9.1 Hz, 1H), 7.23 (m, 2H), 4.51 (q, J=7.0 Hz, 1H), 1.81 (d, J=7.0 Hz, 3H).

Intermediate 8

2-(1-chloroethyl)-6-fluoro-3-phenylquinazolin-4(3H)-one: The title compound was obtained as yellow solid (0.398 g, 35%) by using a procedure that is similar to the one described for intermediate 6 from intermediate 7 (1.20 g, 3.74 mmol) and POCl$_3$ (10 ml). Mass: 303.1 (M$^+$).

Intermediate 9

3-(1-chloroethyl)-2-phenylisoquinolin-1(2H)-one: The title compound was obtained as yellow solid (1.00 g, 58%) by using a procedure that is similar to the one described for intermediate 1 from 3-(1-aminoethyl)-2-phenylisoquinolin-1(2H)-one (1.60 g, 6.05 mmol), 6N HCl (19.2 ml) sodium nitrite (0.650 g, 9.44 mmol). Mass: 284.2 (M$^+$).

Intermediate 10

2-(2-chloropropanamido)-N-phenylbenzamide: The title compound was obtained as yellow solid (2.10 g, 98%) by using a procedure that is similar to the one described for intermediate 5 from 2-amino-N-phenylbenzamide (1.50 g, 7.06 mmol), dichloromethane (15 ml), N-diisopropylethylamine (1.09 g, 8.48 mmol) and 2-chloropropionyl chloride (1.76 g, 8.48 mmol) which was used as such in next step.

Intermediate 11

2-(1-chloroethyl)-3-phenylquinazolin-4(3H)-one: The title compound was obtained as off-white solid (1.00 g, 53%) by using a procedure that is similar to the one described for intermediate 6 from intermediate 10 (2.00 g, 6.60 mmol) and POCl$_3$ (16 ml). Mass: 284.9 (M$^+$).

Intermediate 12

3-(1-(4-amino-3-iodo-1H-pyrazolo[3,4-d]pyrimidin-1-yl)ethyl)-2-phenylisoquinolin-1(2H)-one: To a solution of 3-iodo-1H-pyrazolo[3,4-d]pyrimidin-4-amine[1] (0.45 g, 1.76 mmol) in DMF (7.5 ml), potassium carbonate (0.48 g, 3.52 mmol) was added and stirred at room temperature for 1 h. The reaction mixture was cooled to 0° C., Intermediate 9 (0.65 g, 2.29 mmol) was added and stirred at room temperature for 12 h. The reaction mixture was quenched with water extracted with ethyl acetate. The organic layer was dried over sodium sulphate and concentrated under reduced pressure. The crude product was purified by column chromatography with ethyl acetate:petroleum ether to afford the title compound as a brown solid (0.046 g, 39%). Mass: 508.9 (M$^+$).

Intermediate 13

3-(1-(4-amino-3-iodo-1H-pyrazolo[3,4-d]pyrimidin-1-yl)ethyl)-8-chloro-2-phenylisoquinolin-1(2H)-one: The title compound was obtained as brown solid (0.500 g, 53%) by using a procedure that is similar to the one described for intermediate 12 from 3-iodo-1H-pyrazolo[3,4-d]pyrimidin-4-amine (0.45 g, 1.72 mmol), potassium carbonate (0.476 g, 3.44 mmol), DMF (7.3 ml) and intermediate 2 (0.713 g, 2.24 mmol) which was used as such in next step.

Intermediate 14

2-(2-chlorobutanamido)-N-phenylbenzamide: To a solution of 2-amino-N-phenylbenzamide (2.0 g, 9.42 mmol) in dichloromethane (40 ml), 2-chlorobutyric acid (1.26 g, 10.36 mmol), triethylamine (14.81 ml, 101 mmol), and 4-Dimethylaminopyridine (0.230 g, 1.88 mmol) were added followed by dicyclohexylcarbodiimide (3.88 g, 18.84 mmol). After 12 h at room temperature, the solid precipitated was filtered and the solution was concentrated. The crude product was column chromatographed with ethyl acetate:petroleum ether to afford the desired compound as off-white solid (2.00 g, 67%). $^1$H-NMR (δ ppm, DMSO-d6, 400 MHz): 11.06 (s, 1H), 10.41 (s, 1H), 8.21 (d, J=8.2 Hz, 1H), 7.83 (d, J=7.8 Hz, 1H), 7.69 (m, 2H), 7.57 (m, 1H), 7.37 (t, J=7.9 Hz, 2H), 7.30 (t, J=7.6 Hz, 1H), 7.14 (t, J=7.4 Hz, 1H), 4.64 (dd, J=7.3, 5.6 Hz, 1H), 2.07-1.86 (m, 2H), 0.98 (d, J=7.3 Hz, 3H).

Intermediate 15

2-(1-chloropropyl)-3-phenylquinazolin-4(3H)-one: To intermediate 14 (1.00 g, 3.15 mmol), POCl$_3$ (15 ml) was added and heated to 125° C. for 48 h. The reaction mixture was quenched into crushed ice, neutralised with saturated sodium bicarbonate solution and extracted with ethyl acetate. The organic layer was dried over sodium sulphate and concentrated. The crude product was column chromatographed with ethyl acetate:petroleum ether to afford the desired compound as yellow solid (0.200 g, 21%). $^1$H-NMR (δ ppm, DMSO-d6, 400 MHz): 8.16 (dd, J=7.9, 1.0 Hz, 1H), 7.92 (dt, J=8.3, 1.5 Hz, 1H), 7.78 d, J=7.7 Hz, 1H), 7.62-7.44 (m, 6H), 4.64 (dd, J=7.6, 6.7 Hz, 1H), 2.38 (m, 1H), 2.09 (m, 1H), 0.91 (d, J=7.3 Hz, 3H).

Example 1

3-(1-(4-amino-3-(3-fluoro-4-isopropoxyphenyl)-1H-pyrazolo[3,4-d]pyrimidin-1-yl)ethyl)-8-chloro-2-phenylisoquinolin-1(2H)-one 3-(1-(4-amino-3-(3-fluoro-4-isopropoxyphenyl)-1H-pyrazolo[3,4-d]pyrimidin-1-yl)ethyl)-8-chloro-2-phenylisoquinolin-1(2H)-one: To a solution of 3-(3-fluoro-4-isopropoxyphenyl)-1H-pyrazolo[3,4-d]pyrimidin-4-amine[1] (0.091 g, 0.314 mmol) in DMF (2 ml), potassium carbonate (0.087 g, 0.628 mmol) was added and stirred at room temperature for 30 min. The reaction mixture was cooled to 0° C., intermediate 2 (0.200 g, 0.628 mmol) was added and stirred at 90° C. for 3 h. The reaction mixture was quenched with water and the precipitate formed was filtered and dried under vacuum. The crude product was purified by column chromatography with ethyl acetate:petroleum ether to afford the title compound as off-white solid (0.030 g, 17%). MP: 164-166° C. Mass: 569.7 (M$^+$).

Example 2

3-(1-(4-amino-3-(3-fluoro-4-isopropoxyphenyl)-1H-pyrazolo[3,4-d]pyrimidin-1-yl)ethyl)-8-fluoro-2-phenylisoquinolin-1(2H)-one 3-(1-(4-amino-3-(3-fluoro-4-isopropoxyphenyl)-1H-pyrazolo[3,4-d]pyrimidin-1-yl)ethyl)-8-fluoro-2-phenylisoquinolin-1(2H)-one: The title compound was obtained as brown solid (0.025 g, 13%) by using a procedure that was similar to the one described for example 1 from 3-(3-fluoro-4-isopropoxyphenyl)-1H-pyrazolo[3,4-d]pyrimidin-4-amine[1] (0.099 g, 0.346 mmol), DMF (2.2 nil), potassium carbonate (0.096 g, 0.693 mmol) and intermediate 4 (0.156 g, 0.519 mmol). MP: 264-266° C. Mass: 553.1 (M$^+$+1).

Example 3

2-(1-(4-amino-3-(3-fluoro-4-isopropoxyphenyl)-1H-pyrazolo[3,4-d]pyrimidin-1-yl)ethyl)-5-fluoro-3-phenylquinazolin-4(3H)-one 2-(1-(4-amino-3-(3-fluoro-4-isopropoxyphenyl)-1H-pyrazolo[3,4-d]pyrimidin-1-yl)ethyl)-5-fluoro-3-phenylquinazolin-4(3H)-one: The title compound was obtained as brown solid (0.050 g, 26%) by using a procedure that was similar to the one described for example 1 from 3-(3-fluoro-4-isopropoxyphenyl)-1H-pyrazolo[3,4-d]pyrimidin-4-amine[1] (0.099 g, 0.346 mmol), DMF (2.2 ml), potassium carbonate (0.096 g, 0.693 mmol) and intermediate 6 (0.157 g, 0.519 mmol). MP: 251-153° C. Mass: 553.8 (M$^+$).

Example 4

2-(1-(4-amino-3-(3-fluoro-4-isopropoxyphenyl)-1H-pyrazolo[3,4-d]pyrimidin-1-yl)ethyl)-6-fluoro-3-phenylquinazolin-4(3H)-one 2-(1-(4-amino-3-(3-fluoro-4-isopropoxyphenyl)-1H-pyrazolo[3,4-d]pyrimidin-1-yl)ethyl)-6-fluoro-3-phenylquinazolin-4(3H)-one: The title compound was obtained as brown solid (0.080 g, 42%) by using a procedure that was similar to the one described for example 1 from 3-(3-fluoro-4-isopropoxyphenyl)-1H-pyrazolo[3,4-d]pyrimidin-4-amine[1] (0.099 g, 0.346 mmol), DMF (2.2 ml), potassium carbonate (0.096 g, 0.693 mmol) and intermediate 8 (0.210 g, 0.693 mmol). MP: 215-218° C. Mass: 553.9 (M$^+$).

Example 5

3-(1-(4-amino-3-(3-fluoro-4-isopropoxyphenyl)-1H-pyrazolo[3,4-d]pyrimidin-1-yl)ethyl)-2-phenylisoquinolin-1(2H)-one 3-(1-(4-amino-3-(3-fluoro-4-isopropoxyphenyl)-1H-pyrazolo[3,4-d]pyrimidin-1-yl)ethyl)-2-phenylisoquinolin-1(2H)-one: The title compound was obtained as off-white solid (0.109 g, 39%) by using a procedure that was similar to the one described for example 1 from 3-(3-fluoro-4-isopropoxyphenyl)-1H-pyrazolo[3,4-d]pyrimidin-4-amine[1] (0.150 g, 0.522 mmol), DMF (3.5 ml), potassium carbonate (0.144 g, 1.044 mmol) and intermediate 9 (0.296 g, 1.044 mmol). MP: 264-267° C. Mass: 555.0 (M$^+$).

Example 5a and 5b (+)-3-(1-(4-amino-3-(3-fluoro-4-isopropoxyphenyl)-1H-pyrazolo[3,4-d]pyrimidin-1-yl)ethyl)-2-phenylisoquinolin-1(2H)-one and (−)-3-(1-(4-amino-3-(3-fluoro-4-isopropoxyphenyl)-1H-pyrazolo[3,4-d]pyrimidin-1-yl)ethyl)-2-phenylisoquinolin-1(2H)-one The two enantiomerically pure isomers were separated by preparative SFC conditions from 3-(1-(4-amino-3-(3-fluoro-4-isopropoxyphenyl)-1H-pyrazolo[3,4-d]pyrimidin-1-yl)ethyl)-2-phenylisoquinolin-1(2H)-one (0.500 g) on a CHIRALPAK AS-H column (250×20 mm; 5 μm) using methanol:$CO_2$ (40:60) as the mobile phase at a flow rate of 80 g/min.

Example 5a

Brown solid (0.438 g). e.e. 100%. Rt: 2.29 min. Mass: 535.2 (M$^+$). MP: 231-233° C.

Example 5b

Brown solid (0.439 g). e.e. 100%. Rt: 3.99 min. Mass: 535.2 (M$^+$). MP: 232-235° C.

Example 6

2-(1-(4-amino-3-(3-fluoro-4-isopropoxyphenyl)-1H-pyrazolo[3,4-d]pyrimidin-1-yl)ethyl)-3-phenylquinazolin-4(3H)-one 2-(1-(4-amino-3-(3-fluoro-4-isopropoxyphenyl)-1H-pyrazolo[3,4-d]pyrimidin-1-yl)ethyl)-3-phenylquinazolin-4(3H)-one: The title compound was obtained as brown solid (0.200 g, 64%) by using a procedure that was similar to the one described for example 1 from 3-(3-fluoro-4-isopropoxyphenyl)-1H-pyrazolo[3,4-d]pyrimidin-4-amine[1] (0.168 g, 0.584 mmol), DMF (2.0 ml), potassium carbonate (0.121 g, 0.877 mmol) and intermediate 11 (0.248 g, 0.877 mmol). MP: 236-239° C. Mass: 536.1 (M$^+$).

Example 6a and 6b (+)-2-(1-(4-amino-3-(3-fluoro-4-isopropoxyphenyl)-1H-pyrazolo[3,4-d]pyrimidin-1-yl)ethyl)-3-phenylquinazolin-4(3H)-one and (−)-2-(1-(4-amino-3-(3-fluoro-4-isopropoxyphenyl)-1H-pyrazolo[3,4-d]pyrimidin-1-yl)ethyl)-3-phenylquinazolin-4(3H)-one The two enantiomerically pure isomers were separated by preparative SFC conditions from 2-(1-(4-amino-3-(3-fluoro-4-isopropoxyphenyl)-1H-pyrazolo[3,4-d]pyrimidin-1-yl)ethyl)-3-phenylquinazolin-4(3H)-one (0.500 g) on a CHIRALPAK AS-H column (250×20 mm; 5 μm) using methanol:$CO_2$ (55:45) as the mobile phase at a flow rate of 60 g/min.

Example 6a

Brown solid (0.519 g). e.e. 100%. Rt: 2.41 min. Mass: 536.2 (M$^+$). MP: 189-192° C.

Example 6b

Brown solid (0.490 g). e.e. 99.62%. Rt: 4.10 min. Mass: 536.2 (M$^+$). MP: 192-195° C.

Example 7

3-(1-(4-amino-3-(3-fluoro-4-hydroxyphenyl)-1H-pyrazolo[3,4-d]pyrimidin-1-yl)ethyl)-2-phenylisoquinolin-1(2H)-one 3-(1-(4-amino-3-(3-fluoro-4-hydroxyphenyl)-1H-pyrazolo[3,4-d]pyrimidin-1-yl)ethyl)-2-phenylisoquinolin-1(2H)-one: To Example 5 (0.060 g, 0.112 mmol) in dichloromethane (10 ml) cooled to 0° C., boron tribromide (1M in dichloromethane, 0.64 ml) was added drop wise and stirred for 1 h. The reaction mixture was quenched with 2N HCl solution, extracted with dichloromethane, dried over sodium sulphate and concentrated under reduced pressure. The crude product was purified by column chromatography with ethyl acetate:petroleum ether to afford the title compound as a off-white solid (0.025 g, 45%). MP: 237-2390C. Mass: 492.8 (M+).

Example 7a and 7b (+)-3-(1-(4-amino-3-(3-fluoro-4-hydroxyphenyl)-1H-pyrazolo[3,4-d]pyrimidin-1-yl)ethyl)-2-phenylisoquinolin-1(2H)-one and (−)-3-(1-(4-amino-3-(3-fluoro-4-hydroxyphenyl)-1H-pyrazolo[3,4-d]pyrimidin-1-yl)ethyl)-2-phenylisoquinolin-1(2H)-one The two enantiomerically pure isomers were separated by preparative SFC conditions from 3-(1-(4-amino-3-(3-fluoro- 4-hydroxyphenyl)-1H-pyrazolo[3,4-d]pyrimidin-1-yl) ethyl)-2-phenylisoquinolin-1(2H)-one (0.500 g) on a CHIRALPAK AS-H column (250×20 mm; 5 μm) using methanol:$CO_2$ (55:45) as the mobile phase at a flow rate of 60 g/min.

Example 7a

Brown solid (0.428 g). e.e. 100%. Rt: 2.25 min. Mass: 493.2 ($M^+$). MP: 229-231° C.

Example 7b

Brown solid (0.347 g). e.e. 99.48%. Rt: 4.11 min. Mass: 493.2 ($M^+$). MP: 230-232° C.

Example 8

2-(1-(4-amino-3-(3-fluoro-4-hydroxyphenyl)-1H-pyrazolo[3,4-d]pyrimidin-1-yl)ethyl)-3-phenylquinazolin-4(3H)-one 2-(1-(4-amino-3-(3-fluoro-4-hydroxyphenyl)-1H-pyrazolo[3,4-d]pyrimidin-1-yl)ethyl)-3-phenylquinazolin-4(3H)-one: The title compound was obtained as brown solid (0.035 g, 40%) by using a procedure that was similar to the one described for example 7 from example 6 (0.095 g, 0.177 mmol), dichloromethane (5.0 ml) and boron tribromide (1M in dichloromethane, 1.0 ml). MP: 230-233° C. Mass: 494.1 ($M^++1$).

Example 9

N-(5-(4-amino-1-(1-(1-oxo-2-phenyl-1,2-dihydroisoquinolin-3-yl)ethyl)-1H-pyrazolo[3,4-d]pyrimidin-3-yl)-2-methoxyphenyl)methanesulfonamide N-(5-(4-amino-1-(1-(1-oxo-2-phenyl-1,2-dihydroisoquinolin-3-yl)ethyl)-1H-pyrazolo[3,4-d]pyrimidin-3-yl)-2-methoxyphenyl)methanesulfonamide: To a solution of intermediate 12 (0.200 g, 0.393 mmol), in DME (2 mL), and water (0.7 mL), N-(2-methoxy-5-(4,4,5,5-tetramethyl-1,3,2-dioxaborolan-2-yl)phenyl)methane sulfonamide[2] (0.157 g, 0.590 mmol) and sodium carbonate (0.083 g, 0.786 mmol) were added and the system was degassed for 5 min. and bis(diphenylphosphino)ferrocene]dichloropalladium(II) (0.064 g, 0.078 mmol) was added under nitrogen atmosphere and the mixture was heated to 100° C. at a microwave reactor for 15 min. The reaction mixture was celite filtered, diluted with ethyl acetate, dried over $Na_2SO_4$ and concentrated. The crude product was column chromatographed with ethyl acetate:petroleum ether to afford the desired compound as brown solid (0.033 g, 15%). MP: 260-263° C. Mass: 582.1 ($M^++1$).

Example 9a and 9b (+)—N-(5-(4-amino-1-(1-(1-oxo-2-phenyl-1,2-dihydroisoquinolin-3-yl)ethyl)-1H-pyrazolo[3,4-d]pyrimidin-3-yl)-2-methoxyphenyl)methanesulfonamide and (−)—N-(5-(4-amino-1-(1-(1-oxo-2-phenyl-1,2-dihydroisoquinolin-3-yl)ethyl)-1H-pyrazolo[3,4-d]pyrimidin-3-yl)-2-methoxyphenyl)methanesulfonamide The two enantiomerically pure isomers were separated by preparative SFC conditions from N-(5-(4-amino-1-(1-(1-oxo-2-phenyl-1,2-dihydroisoquinolin-3-yl)ethyl)-1H-pyrazolo[3,4-d]pyrimidin-3-yl)-2-methoxyphenyl)methanesulfonamide (0.500 g) on a CHIRALPAK AS-H column (250×20 mm; 5 μm) using methanol:$CO_2$ (40:60) as the mobile phase at a flow rate of 60 g/min.

Example 9a

Brown solid (0.149 g). e.e. 99.55%. Rt: 2.06 min. Mass: 582.2 ($M^+$). MP: 165-168° C.

Example 9b

Brown solid (0.212 g). e.e. 99.79%. Rt: 3.67 min. Mass: 582.2 ($M^+$). MP: 158-162° C.

Example 10

2-(1-(4-amino-3-(4-methoxy-3-nitrophenyl)-1H-pyrazolo[3,4-d]pyrimidin-1-yl)ethyl)-3-phenylquinazolin-4(3H)-one 2-(1-(4-amino-3-(4-methoxy-3-nitrophenyl)-1H-pyrazolo[3,4-d]pyrimidin-1-yl)ethyl)-3-phenylquinazolin-4(3H)-one: The title compound was obtained as brown solid (1.05 g, 70%) by using a procedure that was similar to the one described for example 1 from 3-(4-methoxy-3-nitrophenyl)-1H-pyrazolo[3,4-d]pyrimidin-4-amine (0.610 g, 2.15 mmol), DMF (9.6 ml), potassium carbonate (0.594 g, 4.30 mmol) and intermediate 11 (0.800 g, 2.79 mmol) Which was used as such in next step.

Example 11

3-(1-(4-amino-3-(3-amino-4-methoxyphenyl)-1H-pyrazolo[3,4-d]pyrimidin-1-yl)ethyl)-2-phenylisoquinolin-1(2H)-one 3-(1-(4-amino-3-(3-amino-4-methoxyphenyl)-1H-pyrazolo[3,4-d]pyrimidin-1-yl)ethyl)-2-phenylisoquinolin-1(2H)-one: To a solution of example 10 (1.00 g, 1.98 mmol) in ethanol (20 ml), Raney Ni (0.50 g) was added and hydrogenated at 40 psi for 12 h. The reaction mixture was passed through celite pad and concentrated. The crude product was column chromatographed with ethyl acetate: petroleum ether to afford the final product as a yellow solid (0.54 g, 57%) which was used as such in next step.

Example 12

N-(5-(4-amino-1-(1-(4-oxo-3-phenyl-3,4-dihydroquinazolin-2-yl)ethyl)-1H-pyrazolo[3,4-d]pyrimidin-3-yl)-2-methoxyphenyl)methanesulfonamide N-(5-(4-amino-1-(1-(4-oxo-3-phenyl-3,4-dihydroquinazolin-2-yl)ethyl)-1H-pyrazolo[3,4-d]pyrimidin-3-yl)-2-methoxyphenyl)methanesulfonamide: To a solution of example 11 (0.260 g, 0.515 mmol) in dichloromethane cooled to 0° C., pyridine (0.08 ml, 1.03 mmol) was added and stirred for 10 min. Methanesulphonyl chloride (0.039 ml, 0.515 mmol) was added stirred for 30 min. The reaction mixture was quenched with water, extracted with dichloromethane and dried over sodium sulphate. The crude product was column chromatographed with methanol:dichlo-

Example 13

2-(1-(4-amino-3-(3-fluoro-4-hydroxyphenyl)-1H-pyrazolo[3,4-d]pyrimidin-1-yl)ethyl)-6-fluoro-3-phenylquinazolin-4(3H)-one 2-(1-(4-amino-3-(3-fluoro-4-hydroxyphenyl)-1H-pyrazolo[3,4-d]pyrimidin-1-yl)ethyl)-6-fluoro-3-phenylquinazolin-4(3H)-one: The title compound was obtained as yellow solid (0.026 g, 14%) by using a procedure that was similar to the one described for example 7 from example 4 (0.200 g, 0.360 mmol), dichloromethane (10.0 ml) and boron tribromide (1M in dichloromethane, 2.05 ml). MP: 231-232° C. Mass: 511.8 (M$^+$).

Example 14

3-(1-(4-amino-3-(3-fluoro-4-hydroxyphenyl)-1H-pyrazolo[3,4-d]pyrimidin-1-yl)ethyl)-8-chloro-2-phenylisoquinolin-1(2H)-one 3-(1-(4-amino-3-(3-fluoro-4-hydroxyphenyl)-1H-pyrazolo[3,4-d]pyrimidin-1-yl)ethyl)-8-chloro-2-phenylisoquinolin-1(2H)-one: The title compound was obtained as yellow solid (0.032 g, 29%) by using a procedure that was similar to the one described for example 7 from example 1 (0.120 g, 0.210 mmol), dichloromethane (6.0 ml) and boron tribromide (1M in dichloromethane, 1.18 ml). MP: 218-219° C. Mass: 526.6 (M$^+$).

Example 14a and 14b (+)-3-(1-(4-amino-3-(3-fluoro-4-hydroxyphenyl)-1H-pyrazolo[3,4-d]pyrimidin-1-yl)ethyl)-8-chloro-2-phenylisoquinolin-1(2H)-one and (−)-3-(1-(4-amino-3-(3-fluoro-4-hydroxyphenyl)-1H-pyrazolo[3,4-d]pyrimidin-1-yl)ethyl)-8-chloro-2-phenylisoquinolin-1(2H)-one The two enantiomerically pure isomers were separated by preparative SFC conditions from 3-(1-(4-amino-3-(3-fluoro-4-hydroxyphenyl)-1H-pyrazolo[3,4-d]pyrimidin-1-yl)ethyl)-8-chloro-2-phenylisoquinolin-1(2H)-one (0.500 g) on a CHIRALPAK AS-H column (250×20 mm; 5 μm) using methanol:$CO_2$ (45:55) as the mobile phase at a flow rate of 80 g/min.

Example 14a

Brown solid (0.349 g). e.e. 97.07%. Rt: 2.51 min. Mass: 527.1 (M$^+$). MP: 215-219° C.

Example 14b

Brown solid (0.026 g). e.e. 95.21%. Rt: 3.82 min. Mass: 527.1 (M$^+$). MP: 215-219° C.

Example 15

3-(1-(4-amino-3-(3-fluoro-4-hydroxyphenyl)-1H-pyrazolo[3,4-d]pyrimidin-1-yl)ethyl)-8-fluoro-2-phenylisoquinolin-1(2H)-one 3-(1-(4-amino-3-(3-fluoro-4-hydroxyphenyl)-1H-pyrazolo[3,4-d]pyrimidin-1-yl)ethyl)-8-fluoro-2-phenylisoquinolin-1(2H)-one: The title compound was obtained as yellow solid (0.066 g, 47%) by using a procedure that was similar to the one described for example 7 from example 2 (0.150 g, 0.271 mmol), dichloromethane (7.5 ml) and boron tribromide (1M in dichloromethane, 1.55 ml). MP: 228-229° C. Mass: 511.0 (M$^+$).

Example 15a and 15b (+)-3-(1-(4-amino-3-(3-fluoro-4-hydroxyphenyl)-1H-pyrazolo[3,4-d]pyrimidin-1-yl)ethyl)-8-fluoro-2-phenylisoquinolin-1(2H)-one and (−)-3-(1-(4-amino-3-(3-fluoro-4-hydroxyphenyl)-1H-pyrazolo[3,4-d]pyrimidin-1-yl)ethyl)-8-fluoro-2-phenylisoquinolin-1(2H)-one The two enantiomerically pure isomers were separated by preparative SFC conditions from 3-(1-(4-amino-3-(3-fluoro-4-hydroxyphenyl)-1H-pyrazolo[3,4-d]pyrimidin-1-yl)ethyl)-8-fluoro-2-phenylisoquinolin-1(2H)-one (0.500 g) on a CHIRALPAK AS-H column (250×20 mm; 5 μm) using methanol:$CO_2$ (45:55) as the mobile phase at a flow rate of 80 g/min.

Example 15a

Off-white solid (0.480 g). e.e. 100%. Rt: 2.91 min. Mass: 511.1 (M$^+$). MP: 268-270° C.

Example 15b

Off-white solid (0.453 g). e.e. 99.9%. Rt: 5.12 min. Mass: 511.1 (M$^+$). MP: 258-260° C.

Example 16

2-(1-(4-amino-3-(3-fluoro-4-hydroxyphenyl)-1H-pyrazolo[3,4-d]pyrimidin-1-yl)ethyl)-5-fluoro-3-phenylquinazolin-4(3H)-one 2-(1-(4-amino-3-(3-fluoro-4-hydroxyphenyl)-1H-pyrazolo[3,4-d]pyrimidin-1-yl)ethyl)-5-fluoro-3-phenylquinazolin-4(3H)-one The title compound was obtained as brown solid (0.050 g, 27%) by using a procedure that was similar to the one described for example 7 from example 3 (0.200 g, 0.360 mmol), dichloromethane (10.0 ml) and boron tribromide (1M in dichloromethane, 2.05 ml). MP: 212-214° C. Mass: 512.0 (M$^+$).

Example 16a and 16b (+)-2-(1-(4-amino-3-(3-fluoro-4-hydroxyphenyl)-1H-pyrazolo[3,4-d]pyrimidin-1-yl)ethyl)-5-fluoro-3-phenylquinazolin-4(3H)-one and (−)-2-(1-(4-amino-3-(3-fluoro-4-hydroxyphenyl)-1H-pyrazolo[3,4-d]pyrimidin-1-yl)ethyl)-5-fluoro-3-phenylquinazolin-4(3H)-one The two enantiomerically pure isomers were separated by preparative SFC conditions from 2-(1-(4-amino-3-(3-fluoro-4-hydroxyphenyl)-1H-pyrazolo[3,4-d]pyrimidin-1-yl)ethyl)-5-fluoro-3-phenylquinazolin-4(3H)-one (0.500 g) on a CHIRALPAK AS-H column (250×20 mm; 5 μm) using methanol:$CO_2$ (45:55) as the mobile phase at a flow rate of 80 g/min.

Example 16a

Off-white solid (0.458 g). e.e. 99.88%. Rt: 2.34 min. Mass: 512.2 (M+) MP: 268-270° C.

Example 16b

Off-white solid (0.469 g). e.e. 99.05%. Rt: 3.92 min. Mass: 512.2 (M+). MP: 269-271° C.

Example 17

3-(1-(4-amino-3-(4-(difluoromethoxy)-3-fluorophenyl)-1H-pyrazolo[3,4-d]pyrimidin-1-yl)ethyl)-8-chloro-2-phenylisoquinolin-1(2H)-one 3-(1-(4-amino-3-(4-(difluoromethoxy)-3-fluorophenyl)-1H-pyrazolo[3,4-d]pyrimidin-1-yl)ethyl)-8-chloro-2-phenylisoquinolin-1(2H)-one: The title compound was obtained as off-white solid (0.020 g, 7%) by using a procedure that was similar to the one described for example 1 from 3-(4-(difluoromethoxy)-3-fluorophenyl)-1H-pyrazolo[3,4-d]pyrimidin-4-amine[1] (0.150 g, 0.507 mmol), DMF (1.5 ml), potassium carbonate (0.140 g, 1.015 mmol) and intermediate 2 (0.323 g, 1.015 mmol). MP: 160-162° C. Mass: 576.7 (M+).

Example 17a and 17b (+)-3-(1-(4-amino-3-(4-(difluoromethoxy)-3-fluorophenyl)-1H-pyrazolo[3,4-d]pyrimidin-1-yl)ethyl)-8-chloro-2-phenylisoquinolin-1(2H)-one and (−)-3-(1-(4-amino-3-(4-(difluoromethoxy)-3-fluorophenyl)-1H-pyrazolo[3,4-d]pyrimidin-1-yl)ethyl)-8-chloro-2-phenylisoquinolin-1(2H)-one The two enantiomerically pure isomers were separated by preparative SFC conditions from 3-(1-(4-amino-3-(4-(difluoromethoxy)-3-fluorophenyl)-1H-pyrazolo[3,4-d]pyrimidin-1-yl)ethyl)-8-chloro-2-phenylisoquinolin-1(2H)-one (0.500 g) on a CHIRALPAK AS-H column (250×20 mm; 5 μm) using methanol:$CO_2$ (50:50) as the mobile phase at a flow rate of 70 g/min.

Example 17a

Browne solid (0.500 g). e.e. 99.25%. Rt: 2.35 min. Mass: 577.2 (M+) MP: 180-184° C.

Example 17b

Brown solid (0.422 g). e.e. 100%. Rt: 3.87 min. Mass: 577.2 (M+). MP: 181-185° C.

Example 18

3-(1-(4-amino-3-(4-methoxy-3-nitrophenyl)-1H-pyrazolo[3,4-d]pyrimidin-1-yl)ethyl)-8-chloro-2-phenylisoquinolin-1(2H)-one 3-(1-(4-amino-3-(4-methoxy-3-nitrophenyl)-1H-pyrazolo[3,4-d]pyrimidin-1-yl)ethyl)-8-chloro-2-phenylisoquinolin-1(2H)-one: The title compound was obtained as brown solid (0.270 g, 54%) by using a procedure that was similar to the one described for example 1 from 3-(4-methoxy-3-nitrophenyl)-1H-pyrazolo[3,4-d]pyrimidin-4-amine (0.250 g, 0.876 mmol), DMF (2.5 ml), potassium carbonate (0.241 g, 1.75 mmol) and intermediate 2 (0.557 g, 1.75 mmol) Which was used as such in next step.

Example 19

3-(1-(4-amino-3-(3-amino-4-methoxyphenyl)-1H-pyrazolo[3,4-d]pyrimidin-1-yl)ethyl)-8-chloro-2-phenylisoquinolin-1(2H)-one 3-(1-(4-amino-3-(3-amino-4-methoxyphenyl)-1H-pyrazolo[3,4-d]pyrimidin-1-yl)ethyl)-8-chloro-2-phenylisoquinolin-1(2H)-one: The title compound was obtained as brown solid (0.150 g, 58%) by using a procedure that was similar to the one described for example 11 from example 18 (0.270 g, 0.476 mmol), ethanol (5 ml), Raney Ni (0.135 g) which was used as such in next step.

Example 20

N-(5-(4-amino-1-(1-(8-chloro-1-oxo-2-phenyl-1,2-dihydroisoquinolin-3-yl)ethyl)-1H-pyrazolo[3,4-d]pyrimidin-3-yl)-2-methoxyphenyl)methanesulfonamide N-(5-(4-amino-1-(1-(8-chloro-1-oxo-2-phenyl-1,2-dihydroisoquinolin-3-yl)ethyl)-1H-pyrazolo[3,4-d]pyrimidin-3-yl)-2-methoxyphenyl)methanesulfonamide: The title compound was obtained as off-white solid (0.020 g, 13%) by using a procedure that was similar to the one described for example 12 from example 19 (0.135 g, 0.251 mmol), pyridine (0.10 ml, 0.484 mmol), dichloromethane (2 ml) and methanesulphonyl chloride (0.10 ml, 0.252 mmol). Mass: 616.0 (M+).

Example 20a and 20b (+)—N-(5-(4-amino-1-(1-(8-chloro-1-oxo-2-phenyl-1,2-dihydroisoquinolin-3-yl)ethyl)-1H-pyrazolo[3,4-d]pyrimidin-3-yl)-2-methoxyphenyl)methanesulfonamide and (+N-(5-(4-amino-1-(1-(8-chloro-1-oxo-2-phenyl-1,2-dihydroisoquinolin-3-yl)ethyl)-1H-pyrazolo[3,4-d]pyrimidin-3-yl)-2-methoxyphenyl)methanesulfonamide The two enantiomerically pure isomers were separated by preparative SFC conditions from N-(5-(4-amino-1-(1-(8-chloro-1-oxo-2-phenyl-1,2-dihydroisoquinolin-3-yl)ethyl)-1H-pyrazolo[3,4-d]pyrimidin-3-yl)-2-methoxyphenyl)methanesulfonamide (0.500 g) on a CHIRALPAK AS-H column (250×20 mm; 5 μm) using methanol:$CO_2$ (45:55) as the mobile phase at a flow rate of 80 g/min.

Example 20a

Brown solid (0.397 g). e.e. 98.54%. Rt: 2.26 min. Mass: 616.2 (M+). MP: 178-181° C.

Example 20b

Brown solid (0.252 g). e.e. 98.77%. Rt: 3.18 min. Mass: 616.2 (M+). MP: 180-183° C.

Example 21

3-(1-(4-amino-3-(3-methyl-1H-indazol-6-yl)-1H-pyrazolo[3,4-d]pyrimidin-1-yl)ethyl)-8-chloro-2-phenylisoquinolin-1(2H)-one 3-(1-(4-amino-3-(3-methyl-1H-indazol-6-yl)-1H-pyrazolo[3,4-d]pyrimidin-1-yl)ethyl)-8-chloro-2-phenylisoquinolin-1(2H)-one: The title compound was obtained as brown solid (0.020 g, 10%) by using a procedure that was similar to the one described for example 9 from intermediate 13 (0.200 g, 0.368 mmol), DME (2.5 ml), water (1.0 ml), tert-butyl 3-methyl-6-(4,4,5,5-tetramethyl-1,3,2-dioxaborolan-2-yl)-1H-indazole-1-carboxylate (0.198 g, 0.552 mmol), sodium carbonate (0.078 g, 0.736 mmol) and bis(diphenylphosphino)ferrocene]dichloropalladium(II) (0.060 g, 0.073 mmol) under microwave irradiation (microwave power=100 W, temperature=100° C.) for 45 min. MP: 289-291° C. Mass: 546.9 ($M^+$).

Example 21a and 21b (+)-3-(1-(4-amino-3-(3-methyl-1H-indazol-6-yl)-1H-pyrazolo[3,4-d]pyrimidin-1-yl)ethyl)-8-chloro-2-phenylisoquinolin-1(2H)-one and (−)-3-(1-(4-amino-3-(3-methyl-1H-indazol-6-yl)-1H-pyrazolo[3,4-d]pyrimidin-1-yl)ethyl)-8-chloro-2-phenylisoquinolin-1(2H)-one The two enantiomerically pure isomers were separated by preparative SFC conditions from 3-(1-(4-amino-3-(3-methyl-1H-indazol-6-yl)-1H-pyrazolo[3,4-d]pyrimidin-1-yl)ethyl)-8-chloro-2-phenylisoquinolin-1(2H)-one (0.500 g) on a CHIRALPAK AS-H column (250×20 mm; 5 μm) using methanol:$CO_2$ (35:65) as the mobile phase at a flow rate of 80 g/min.

Example 21a

Brown solid (0.327 g). e.e. 98.29%. Rt: 4.26 min. Mass: 547.2 ($M^+$). MP: 230-233° C.

Example 21b

Brown solid (0.599 g). e.e. 95.03%. Rt: 5.44 min. Mass: 547.2 ($M^+$). MP: 225-227° C.

Example 22

2-{1-[4-Amino-3-(3-fluoro-4-isopropoxy-phenyl)-pyrazolo[3,4-d]pyrimidin-1-yl]-propyl}-3-phenyl-3H-quinazolin-4-one 2-(1-(4-amino-3-(3-fluoro-4-isopropoxyphenyl)-1H-pyrazolo[3,4-d]pyrimidin-1-yl)propyl)-3-phenylquinazolin-4(3H)-one: To a solution of 3-(3-fluoro-4-isopropoxyphenyl)-1H-pyrazolo[3,4-d]pyrimidin-4-amine[1] (0.115 g, 0.402 mmol) in DMF (2 ml), potassium carbonate (0.084 g, 0.604 mmol) was added and stirred at room temperature for 30 min. The intermediate 15 (0.180 g, 0.604 mmol) was added and stirred at 90° C. for 12 h. The reaction mixture was quenched with water and the precipitate formed was filtered and dried under vacuum. The crude product was purified by column chromatography with methanol:dichloromethane ether to afford the title compound as brown solid (0.070 g, 17%). MP: 261-263° C. Mass: 550.6 ($M^+1$).

Biological Assay

The pharmacological properties of the compounds of this invention may be confirmed by a number of pharmacological assays. The pharmacological assays which can be been carried out with the compounds according to the invention and/or their pharmaceutically acceptable salts is exemplified below.

Assay 1

Fluorescent Determination of PI3Kinase Enzyme Activity

Phosphoinositide 3 kinases (PI3K) belong to a class of Lipid kinases that play a critical role in the regulation of several key cellular processes. The PI3K are capable of phosphorylating the 3-hydroxy position of phosphoinositols thereby generating second messengers involved in downstream signalling events. The homogenous time resolved fluorescence (HTRF) assay allows detection of 3,4,5-triphosphate (PIP3) formed as a result of phosphorylation of phosphotidylinositol 4,5-biphosphate (PIP2) by PI3K isoforms such as α, μ, γ or δ.

PI3K isoform activity for α, β, γ or δ is to be determined using a PI3K human HTRF™ Assay Kit (Millipore, Billerica, Mass.) with modifications. All incubations were carried out at room temperature. Briefly, 0.5 μl of 40× inhibitor (in 100% DMSO) or 100% DMSO were added to each well of a 384-well black plate (Greiner Bio-One, Monroe, N.C.) containing 14.5 μl 1× reaction buffer/PIP2 (10 mM $MgCl_2$, 5 mM DTT, 1.38 μM PIP2) mix with or without enzyme and incubated for 10 min. After the initial incubation, 5 μl/well of 400 μM ATP was added and incubated for an additional 30 minutes. Reaction was terminated by adding 5 μl/well stop solution (Millipore, Billerica, Mass.). Five microliters of detection mix (Millipore, Billerica, Mass.) were then added to each well and was incubated for 6-18 h in the dark. HRTF ratio was measured on a microplate reader (BMG Labtech, Germany) at an excitation wavelength of 337 nm and emission wavelengths of 665 and 620 nm with an integration time of 400 μsec. Data was analyzed using Graphpad Prism (Graphpad software; San Diego Calif.) for $IC_{50}$ determination). The % inhibition for PI3K isoforms as α, β, γ or δ for the compounds of the invention are as provided below.

| Example | % Inhibition @ PI3kδ 100/300 nM | IC50 | PI3kγ 100/300 nM | IC50 | PI3kα 1 um | PI3kβ 1 uM |
|---|---|---|---|---|---|---|
| 1 | D | — | E | — | E1 | E1 |
| 2 | E | — | E | — | E1 | E2 |
| 3 | E | — | E | — | E1 | E2 |
| 4 | E | — | C | — | E1 | E2 |
| 5 | A | — | B | — | E1 | E2 |
| 5a | A | 3.05 | B | 22.18 | E1 | D |
| 5b | C | — | E | — | E1 | B |
| 6 | A | — | C | — | E1 | E1 |
| 6a | A | 2.74 | C | 15.01 | E1 | D |
| 6b | D | — | E | — | E1 | D |
| 7 | C | — | D | — | E2 | D |
| 7a | B | 13.33 | B | 57.73 | E1 | D |
| 7b | C | — | D | — | E1 | D |
| 8 | D | — | E | — | E1 | D |
| 9 | C | — | D | — | D | C |
| 9a | A | 16.22 | C | 203.3 | E1 | D |
| 9b | C | — | E | — | E1 | E2 |
| 12 | E | — | D | — | E1 | D |
| 13 | D | — | D | — | E1 | E2 |
| 14 | B | — | A | — | D | B |
| 14a | A | 4.2 | A | 19.54 | E1 | E2 |
| 14b | B | — | D | — | E1 | D |
| 15 | C | — | C | — | E1 | D |
| 15a | A | 9.99 | C | 52.04 | E1 | E2 |
| 15b | D | — | E | — | E1 | E1 |
| 16 | C | — | C | — | E1 | B |
| 16a | A | 33.26 | D | 121.6 | E1 | E2 |

-continued

| Example | % Inhibition @ | | | | | |
|---|---|---|---|---|---|---|
| | PI3kδ | | PI3kγ | | PI3kα | PI3kβ |
| | 100/300 nM | IC50 | 100/300 nM | IC50 | 1 um | 1 uM |
| 16b | D | — | E | — | E1 | E1 |
| 17 | A | — | A | — | D | C |
| 17a | D | — | E | — | E1 | E1 |
| 17b | A | 45.61 | A | 47.26 | E1 | D |
| 20 | A | — | B | — | C | D |
| 20a | B | 76.41 | D | 141.6 | E1 | E2 |
| 20b | D | — | E | — | E1 | D |
| 21 | A | — | B | — | D | B |
| 21a | A | — | B | — | E1 | E1 |
| 21b | A | — | C | — | E1 | E2 | underlined values are for compounds tested at 300 nM.; % inhibition: A represents >80-≤100%; B represents >60-≤80%; C represents >40-≤60%; D is represents >20-≤40%, E is represents 0-≤20%, E2 is represents >10-≤20%. and E1 is represents 0-≤10%.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above. It is intended that the appended claims define the scope of the invention and that methods and structures within the scope of these claims and their equivalents be covered thereby.

All publications and patent and/or patent applications cited in this application are herein incorporated by reference to the same extent as if each individual publication or patent application was specifically and individually indicated to be incorporated herein by reference.

What is claimed is:

1. A compound selected from:
   3-(1-(4-amino-3-(3-fluoro-4-isopropoxyphenyl)-1H-pyrazolo[3,4-d]pyrimidin-1-yl)ethyl)-8-fluoro-2-phenylisoquinolin-1(2H)-one;
   2-(1-(4-amino-3-(3-fluoro-4-isopropoxyphenyl)-1H-pyrazolo[3,4-d]pyrimidin-1-yl)ethyl)-5-fluoro-3-phenylquinazolin-4(3H)-one;
   2-(1-(4-amino-3-(3-fluoro-4-isopropoxyphenyl)-1H-pyrazolo[3,4-d]pyrimidin-1-yl)ethyl)-6-fluoro-3-phenylquinazolin-4(3H)-one;
   2-(1-(4-amino-3-(3-fluoro-4-hydroxyphenyl)-1H-pyrazolo[3,4-d]pyrimidin-1-yl)ethyl)-6-fluoro-3-phenylquinazolin-4(3H)-one;
   3-(1-(4-amino-3-(3-fluoro-4-hydroxyphenyl)-1H-pyrazolo[3,4-d]pyrimidin-1-yl)ethyl)-8-fluoro-2-phenylisoquinolin-1(2H)-one;
   (+)-3-(1-(4-amino-3-(3-fluoro-4-hydroxyphenyl)-1H-pyrazolo[3,4-d]pyrimidin-1-yl)ethyl)-8-fluoro-2-phenylisoquinolin-1(2H)-one;
   (+3-(1-(4-amino-3-(3-fluoro-4-hydroxyphenyl)-1H-pyrazolo[3,4-d]pyrimidin-1-yl)ethyl)-8-fluoro-2-phenylisoquinolin-1(2H)-one;
   2-(1-(4-amino-3-(3-fluoro-4-hydroxyphenyl)-1H-pyrazolo[3,4-d]pyrimidin-1-yl)ethyl)-5-fluoro-3-phenylquinazolin-4(3H)-one;
   (+)-2-(1-(4-amino-3-(3-fluoro-4-hydroxyphenyl)-1H-pyrazolo[3,4-d]pyrimidin-1-yl)ethyl)-5-fluoro-3-phenylquinazolin-4(3H)-one;
   (−)-2-(1-(4-amino-3-(3-fluoro-4-hydroxyphenyl)-1H-pyrazolo[3,4-d]pyrimidin-1-yl)ethyl)-5-fluoro-3-phenylquinazolin-4(3H)-one;
   and pharmaceutically acceptable salts thereof.

2. A pharmaceutical composition comprising a compound of claim 1 and a pharmaceutically acceptable carrier.

3. The pharmaceutical composition of claim 2, further comprising one or more additional therapeutic agents selected from anti-cancer agents, anti-inflammatory agents, immunosuppressive agents, steroids, non-steroidal anti-inflammatory agents, antihistamines, analgesics, and mixtures thereof.

4. A method of inhibiting a catalytic activity of a PI3 kinase present in a cell, comprising contacting the cell with an effective amount of a compound of claim 1.

5. The method of claim 4, wherein the inhibition takes place in a subject suffering from a disease or disorder which is cancer, bone disorder, inflammatory disease, immune disease, nervous system disease, metabolic disease, respiratory disease, thrombosis, or cardiac disease.

6. A compound selected from:
   3-(1-(4-amino-3-(3-fluoro-4-isopropoxyphenyl)-1H-pyrazolo[3,4-d]pyrimidin-1-yl)ethyl)-8-chloro-2-phenylisoquinolin-1(2H)-one;
   3-(1-(4-amino-3-(3-fluoro-4-isopropoxyphenyl)-1H-pyrazolo[3,4-d]pyrimidin-1-yl)ethyl)-2-phenylisoquinolin-1(2H)-one;
   (+)-3-(1-(4-amino-3-(3-fluoro-4-isopropoxyphenyl)-1H-pyrazolo[3,4-d]pyrimidin-1-yl)ethyl)-2-phenylisoquinolin-1(2H)-one;
   (+3-(1-(4-amino-3-(3-fluoro-4-isopropoxyphenyl)-1H-pyrazolo[3,4-d]pyrimidin-1-yl)ethyl)-2-phenylisoquinolin-1(2H)-one;
   2-(1-(4-amino-3-(3-fluoro-4-isopropoxyphenyl)-1H-pyrazolo[3,4-d]pyrimidin-1-yl)ethyl)-3-phenylquinazolin-4(3H)-one;
   (+)-2-(1-(4-amino-3-(3-fluoro-4-isopropoxyphenyl)-1H-pyrazolo[3,4-d]pyrimidin-1-yl)ethyl)-3-phenylquinazolin-4(3H)-one;
   (−)-2-(1-(4-amino-3-(3-fluoro-4-isopropoxyphenyl)-1H-pyrazolo[3,4-d]pyrimidin-1-yl)ethyl)-3-phenylquinazolin-4(3H)-one;
   3-(1-(4-amino-3-(3-fluoro-4-hydroxyphenyl)-1H-pyrazolo[3,4-d]pyrimidin-1-yl)ethyl)-2-phenylisoquinolin-1(2H)-one;
   (+)-3-(1-(4-amino-3-(3-fluoro-4-hydroxyphenyl)-1H-pyrazolo[3,4-d]pyrimidin-1-yl)ethyl)-2-phenylisoquinolin-1(2H)-one;
   (+3-(1-(4-amino-3-(3-fluoro-4-hydroxyphenyl)-1H-pyrazolo[3,4-d]pyrimidin-1-yl)ethyl)-2-phenylisoquinolin-1(2H)-one;
   N-(5-(4-amino-1-(1-(1-oxo-2-phenyl-1,2-dihydroisoquinolin-3-yl)ethyl)-1H-pyrazolo[3,4-d]pyrimidin-3-yl)-2-methoxyphenyl)methanesulfonamide;
   (+)-N-(5-(4-amino-1-(1-(1-oxo-2-phenyl-1,2-dihydroisoquinolin-3-yl)ethyl)-1H-pyrazolo[3,4-d]pyrimidin-3-yl)-2-methoxyphenyl)methanesulfonamide;
   (−)-N-(5-(4-amino-1-(1-(1-oxo-2-phenyl-1,2-dihydroisoquinolin-3-yl)ethyl)-1H-pyrazolo[3,4-d]pyrimidin-3-yl)-2-methoxyphenyl)methanesulfonamide;
   2-(1-(4-amino-3-(4-methoxy-3-nitrophenyl)-1H-pyrazolo[3,4-d]pyrimidin-1-yl)ethyl)-3-phenylquinazolin-4(3H)-one;
   3-(1-(4-amino-3-(3-amino-4-methoxyphenyl)-1H-pyrazolo[3,4-d]pyrimidin-1-yl)ethyl)-2-phenylisoquinolin-1(2H)-one;

N-(5-(4-amino-1-(1-(4-oxo-3-phenyl-3,4-dihydroquinazolin-2-yl)ethyl)-1H-pyrazolo[3,4-d]pyrimidin-3-yl)-2-methoxyphenyl)methanesulfonamide;

3-(1-(4-amino-3-(3-fluoro-4-hydroxyphenyl)-1H-pyrazolo[3,4-d]pyrimidin-1-yl)ethyl)-8-chloro-2-phenylisoquinolin-1(2H)-one;

(+)-3-(1-(4-amino-3-(3-fluoro-4-hydroxyphenyl)-1H-pyrazolo[3,4-d]pyrimidin-1-yl)ethyl)-8-chloro-2-phenylisoquinolin-1(2H)-one;

(+3-(1-(4-amino-3-(3-fluoro-4-hydroxyphenyl)-1H-pyrazolo[3,4-d]pyrimidin-1-yl)ethyl)-8-chloro-2-phenylisoquinolin-1(2H)-one;

3-(1-(4-amino-3-(4-(difluoromethoxy)-3-fluorophenyl)-1H-pyrazolo[3,4-d]pyrimidin-1-yl)ethyl)-8-chloro-2-phenylisoquinolin-1(2H)-one;

(+)-3-(1-(4-amino-3-(4-(difluoromethoxy)-3-fluorophenyl)-1H-pyrazolo[3,4-d]pyrimidin-1-yl)ethyl)-8-chloro-2-phenylisoquinolin-1(2H)-one;

(+3-(1-(4-amino-3-(4-(difluoromethoxy)-3-fluorophenyl)-1H-pyrazolo[3,4-d]pyrimidin-1-yl)ethyl)-8-chloro-2-phenylisoquinolin-1(2H)-one;

3-(1-(4-amino-3-(4-methoxy-3-nitrophenyl)-1H-pyrazolo[3,4-d]pyrimidin-1-yl)ethyl)-8-chloro-2-phenylisoquinolin-1(2H)-one;

3-(1-(4-amino-3-(3-amino-4-methoxyphenyl)-1H-pyrazolo[3,4-d]pyrimidin-1-yl)ethyl)-8-chloro-2-phenylisoquinolin-1(2H)-one;

N-(5-(4-amino-1-(1-(8-chloro-1-oxo-2-phenyl-1,2-dihydroisoquinolin-3-yl)ethyl)-1H-pyrazolo[3,4-d]pyrimidin-3-yl)-2-methoxyphenyl)methanesulfonamide;

(+)-N-(5-(4-amino-1-(1-(8-chloro-1-oxo-2-phenyl-1,2-dihydroisoquinolin-3-yl)ethyl)-1H-pyrazolo[3,4-d]pyrimidin-3-yl)-2-methoxyphenyl)methanesulfonamide;

(−)-N-(5-(4-amino-1-(1-(8-chloro-1-oxo-2-phenyl-1,2-dihydroisoquinolin-3-yl)ethyl)-1H-pyrazolo[3,4-d]pyrimidin-3-yl)-2-methoxyphenyl)methanesulfonamide;

3-(1-(4-amino-3-(3-methyl-1H-indazol-6-yl)-1H-pyrazolo[3,4-d]pyrimidin-1-yl)ethyl)-8-chloro-2-phenylisoquinolin-1(2H)-one;

(+)-3-(1-(4-amino-3-(3-methyl-1H-indazol-6-yl)-1H-pyrazolo[3,4-d]pyrimidin-1-yl)ethyl)-8-chloro-2-phenylisoquinolin-1(2H)-one;

(+3-(1-(4-amino-3-(3-methyl-1H-indazol-6-yl)-1H-pyrazolo[3,4-d]pyrimidin-1-yl)ethyl)-8-chloro-2-phenylisoquinolin-1(2H)-one;

and pharmaceutically acceptable salts thereof.

7. A pharmaceutical composition comprising a compound of claim 6 and a pharmaceutically acceptable carrier.

8. The pharmaceutical composition of claim 7, further comprising one or more additional therapeutic agents selected from anti-cancer agents, anti-inflammatory agents, immunosuppressive agents, steroids, non-steroidal anti-inflammatory agents, antihistamines, analgesics, and mixtures thereof.

9. A method of inhibiting a catalytic activity of a PI3 kinase present in a cell, comprising contacting the cell with an effective amount of a compound of claim 6.

10. The method of claim 9, wherein the inhibition takes place in a subject suffering from a disease or disorder which is cancer, bone disorder, inflammatory disease, immune disease, nervous system disease, metabolic disease, respiratory disease, thrombosis, or cardiac disease.

11. A compound selected from:
2-{1-[4-Amino-3-(3-fluoro-4-isopropoxy-phenyl)-pyrazolo[3,4-d]pyrimidin-1-yl]-propyl}-3-phenyl-3H-quinazolin-4-one;

and pharmaceutically acceptable salts thereof.

12. A pharmaceutical composition comprising a compound of claim 11 and a pharmaceutically acceptable carrier.

13. The pharmaceutical composition of claim 12, further comprising one or more additional therapeutic agents selected from anti-cancer agents, anti-inflammatory agents, immunosuppressive agents, steroids, non-steroidal anti-inflammatory agents, antihistamines, analgesics, and mixtures thereof.

14. A method of inhibiting a catalytic activity of a PI3 kinase present in a cell, comprising contacting the cell with an effective amount of a compound of claim 11.

15. The method of claim 14, wherein the inhibition takes place in a subject suffering from a disease or disorder which is cancer, bone disorder, inflammatory disease, immune disease, nervous system disease, metabolic disease, respiratory disease, thrombosis, or cardiac disease.

\* \* \* \* \*